(12) United States Patent
Lavigne et al.

(10) Patent No.: US 12,383,321 B2
(45) Date of Patent: Aug. 12, 2025

(54) BONE IMPLANTS

(71) Applicant: LDR MEDICAL, Rosieres Pres Troyes (FR)

(72) Inventors: Christophe Lavigne, Austin, TX (US); Patrick Richard, Austin, TX (US); Alexis Mercier, Verrieres (FR); Samuel Lequette, Pessac (FR)

(73) Assignee: LDR Medical (FR)

( * ) Notice: Subject to any disclaimer, the term of this patent is extended or adjusted under 35 U.S.C. 154(b) by 0 days.

(21) Appl. No.: 18/338,634

(22) Filed: Jun. 21, 2023

(65) Prior Publication Data

US 2023/0329765 A1 Oct. 19, 2023

Related U.S. Application Data

(60) Division of application No. 16/881,831, filed on May 22, 2020, now Pat. No. 11,717,333, which is a (Continued)

(30) Foreign Application Priority Data

Aug. 1, 2014 (FR) ..................................... 1457539

(51) Int. Cl.
*A61B 17/70* (2006.01)
*A61B 17/064* (2006.01)
*A61B 17/86* (2006.01)

(52) U.S. Cl.
CPC ........ *A61B 17/864* (2013.01); *A61B 17/0642* (2013.01); *A61B 17/7064* (2013.01); (Continued)

(58) Field of Classification Search
CPC .... A61B 17/86; A61B 17/8635; A61B 17/864
See application file for complete search history.

(56) References Cited

U.S. PATENT DOCUMENTS 3,298,372 A 1/1967 Feinberg
4,860,513 A 8/1989 Whitman
(Continued)

FOREIGN PATENT DOCUMENTS

AU 2015295222 3/2017
CA 2955131 2/2016
(Continued)

OTHER PUBLICATIONS

International Application Serial No. PCT/EP2015/067861, International Search Report mailed Nov. 12, 2015, w/ English Translation, 7 pgs.

(Continued)

*Primary Examiner* — Nicholas W Woodall
(74) *Attorney, Agent, or Firm* — Sheridan Ross P.C.

(57) ABSTRACT

The present invention relates to an implant, an instrument for implanting the implant, and a method for manufacturing the implant which includes an elongated body between a free end and a head along a longitudinal axis on the one hand and turns of at least one threading on at least one portion of said body in proximity to the free end, along the longitudinal axis on the other hand, characterized in that the body includes a longitudinal internal conduit in at least one portion to along the longitudinal axis, obtained by at least one first central machining operation parallel to the longitudinal axis and at least one second machining operation in a so-called transverse plane, not parallel to the longitudinal axis and crossing the wall of the body as far as the longitudinal internal conduit by making windows communicating between said longitudinal internal conduit and the outside of the body.

20 Claims, 36 Drawing Sheets

Figure 1A:
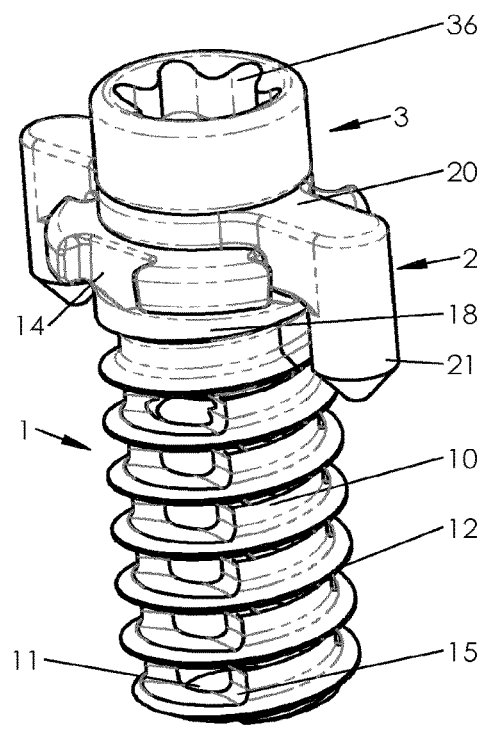

Related U.S. Application Data continuation of application No. 15/501,166, filed as application No. PCT/EP2015/067861 on Aug. 3, 2015, now Pat. No. 10,687,877.

(52) U.S. Cl.
CPC ...... *A61B 17/7098* (2013.01); *A61B 17/8605* (2013.01); *A61B 17/8625* (2013.01)

(56) References Cited

U.S. PATENT DOCUMENTS

| | | | |
|---|---|---|---|
| 5,129,904 A * | 7/1992 | Illi | A61B 17/864 606/907 |
| 5,534,031 A | 7/1996 | Matsuzaki et al. | |
| 5,658,285 A | 8/1997 | Marnay et al. | |
| 5,840,078 A | 11/1998 | Yerys | |
| 5,871,356 A * | 2/1999 | Guedj | A61C 8/0039 433/165 |
| 5,906,616 A * | 5/1999 | Pavlov | A61B 17/8883 606/279 |
| 6,120,503 A | 9/2000 | Michelson | |
| 6,447,545 B1 | 9/2002 | Bagby | |
| 6,824,564 B2 | 11/2004 | Crozet | |
| 6,863,671 B1 * | 3/2005 | Strobel | A61F 2/0811 606/77 |
| 7,083,647 B1 | 8/2006 | Sklar et al. | |
| 7,717,947 B1 | 5/2010 | Wilberg et al. | |
| 8,574,273 B2 | 11/2013 | Russell et al. | |
| 9,173,692 B1 * | 11/2015 | Kaloostian | A61B 17/7037 |
| 10,179,015 B2 | 1/2019 | Lavigne et al. | |
| 10,687,877 B2 | 6/2020 | Lavigne et al. | |
| 11,717,333 B2 | 8/2023 | Lavigne et al. | |
| 2004/0147929 A1 | 7/2004 | Biedermann et al. | |
| 2006/0242642 A1 | 10/2006 | Yamamura et al. | |
| 2006/0247642 A1 * | 11/2006 | Stone | A61B 17/8605 623/13.14 |
| 2007/0233123 A1 | 10/2007 | Ahmad et al. | |
| 2010/0280555 A1 | 11/2010 | Aflatoon et al. | |
| 2011/0190830 A1 * | 8/2011 | Biedermann | A61B 17/864 606/305 |
| 2012/0010662 A1 | 1/2012 | O'Neil et al. | |
| 2013/0253595 A1 * | 9/2013 | Zucherman | A61B 17/8635 606/305 |
| 2014/0046379 A1 * | 2/2014 | Sweeney | A61B 17/863 606/304 |
| 2016/0100870 A1 | 4/2016 | Lavigne et al. | |
| 2017/0224393 A1 | 8/2017 | Lavigne et al. | |

FOREIGN PATENT DOCUMENTS

| | | |
|---|---|---|
| EP | 2589351 | 5/2013 |
| EP | 3185791 | 7/2017 |
| FR | 2954692 | 7/2011 |
| WO | WO 2016016474 | 2/2016 |

OTHER PUBLICATIONS

International Application Serial No. PCT/EP2015/067861, Written Opinion mailed Nov. 12, 2015, w/ English Translation, 13 pgs.
International Application Serial No. PCT/EP2015/067861, International Preliminary Report on Patentability mailed Feb. 16, 2017, 9 pgs.
Chinese Application Serial No. 20158005-1053.9, Office Action mailed Sep. 29, 2018, (w/ English Translation), 21 pgs.
U.S. Appl. No. 14/815,900, Non Final Office Action mailed May 10, 2018, 6 pgs.
U.S. Appl. No. 14/815,900, Notice of Allowance mailed Sep. 19, 2018, 8 pgs.
U.S. Appl. No. 14/815,900, Restriction Requirement mailed Nov. 30, 2017, 7 pgs.
U.S. Appl. No. 15/501,166, Non Final Office Action mailed Sep. 19, 2019, 8 pgs.
U.S. Appl. No. 15/501,166, Notice of Allowance mailed Feb. 26, 2020, 7 pgs.
U.S. Appl. No. 15/501,166, Preliminary Amendment filed Feb. 1, 2017, 13 pgs.
U.S. Appl. No. 15/501,166, Restriction Requirement mailed Apr. 18, 2019, 7 pgs.
Official Action for U.S. Appl. No. 16/881,831, dated Mar. 22, 2022 6 pgs, Restriction Requirement.
Official Action for U.S. Appl. No. 16/881,831, dated Aug. 1, 2022 9 pgs.
Final Action for U.S. Appl. No. 16/881,831, dated Jan. 10, 2023 10 pgs.
Notice of Allowance for U.S. Appl. No. 16/881,831, dated Mar. 13, 2023 8 pgs.
Corrected Notice of Allowance for U.S. Appl. No. 16/881,831, dated Mar. 30, 2023 3 pgs.

* cited by examiner

Figure 4A
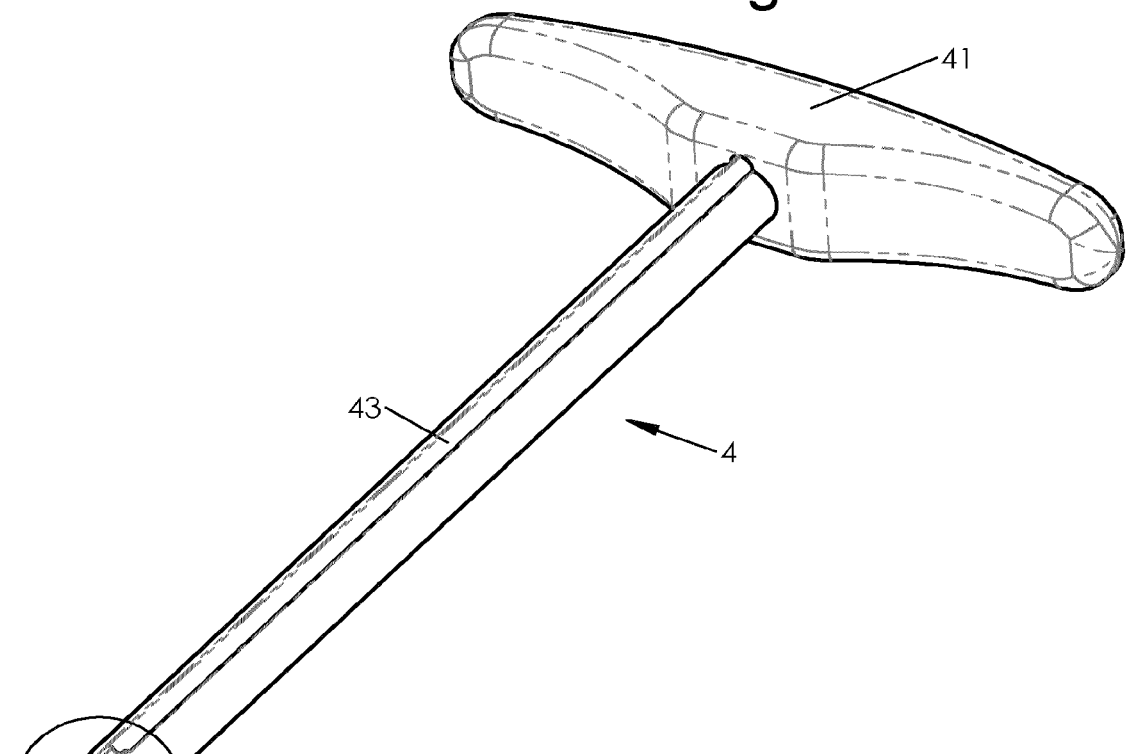
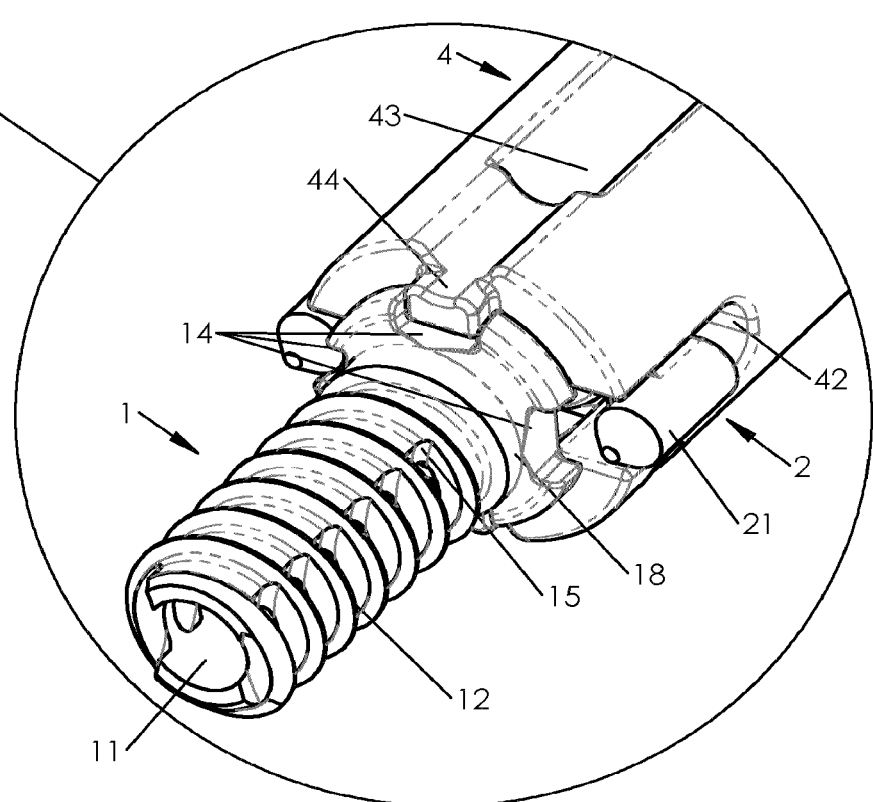
Figure 4B

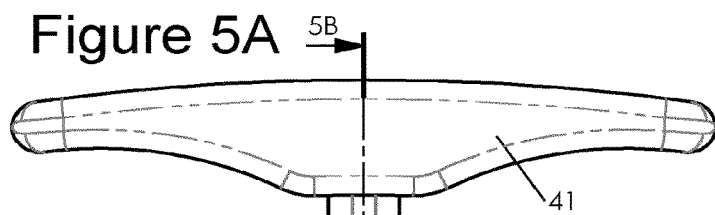
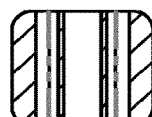
Figure 5A
Figure 5B
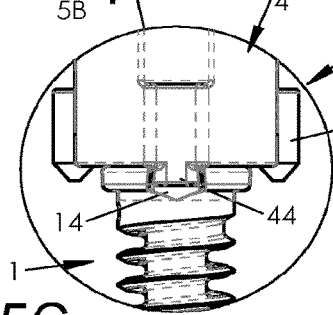
Figure 5C
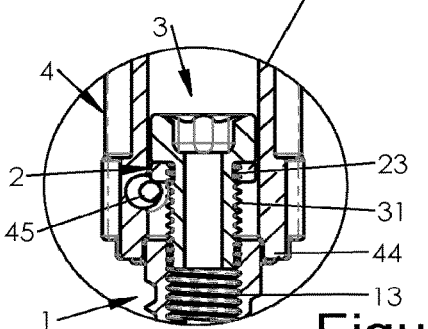
Figure 5D Figure 8A
Figure 8B
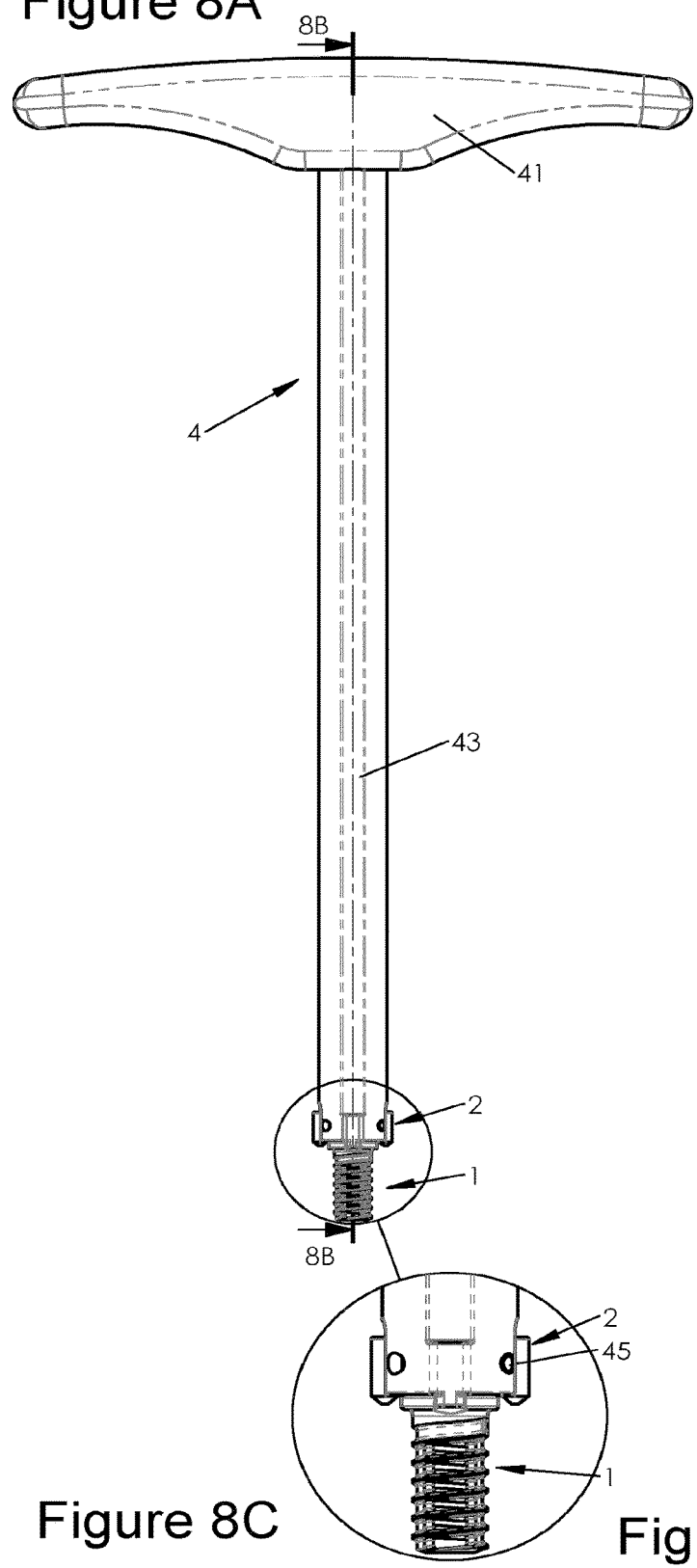
Figure 8C
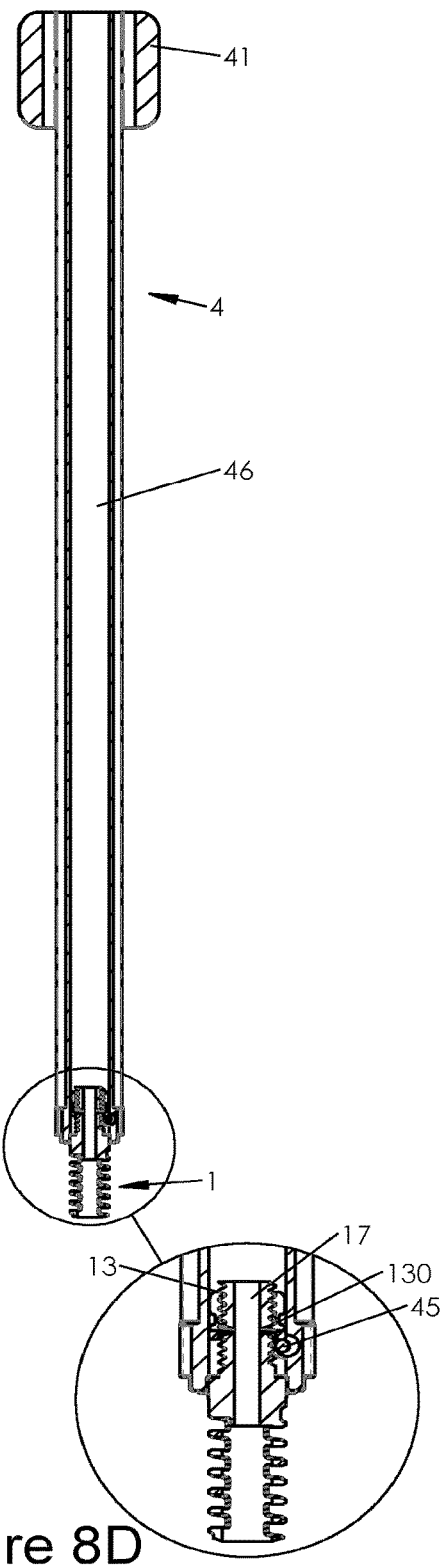
Figure 8D

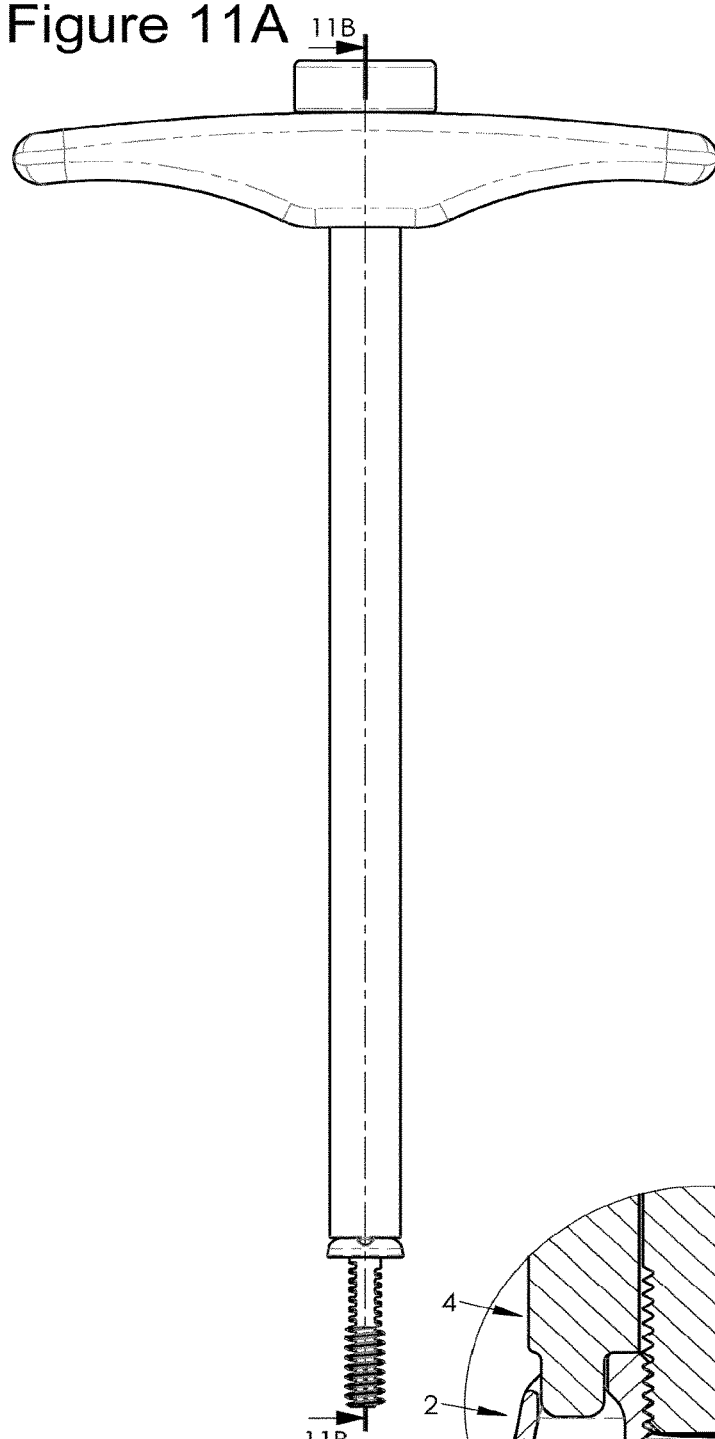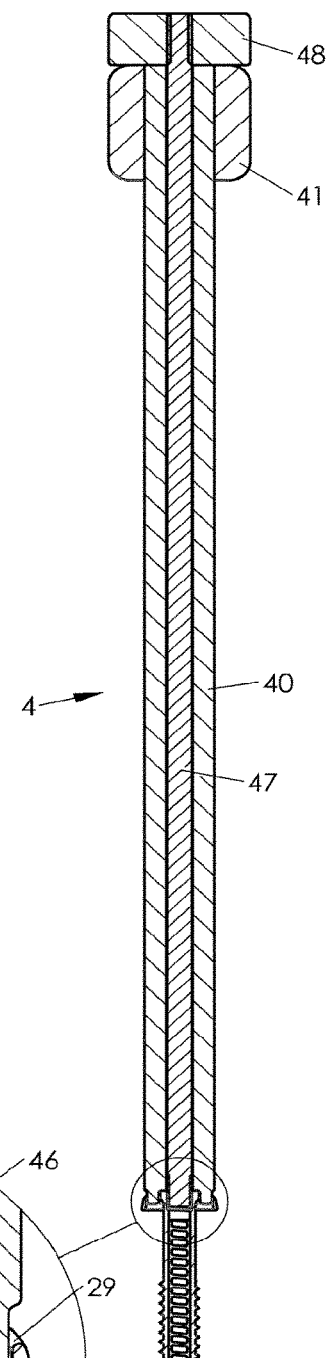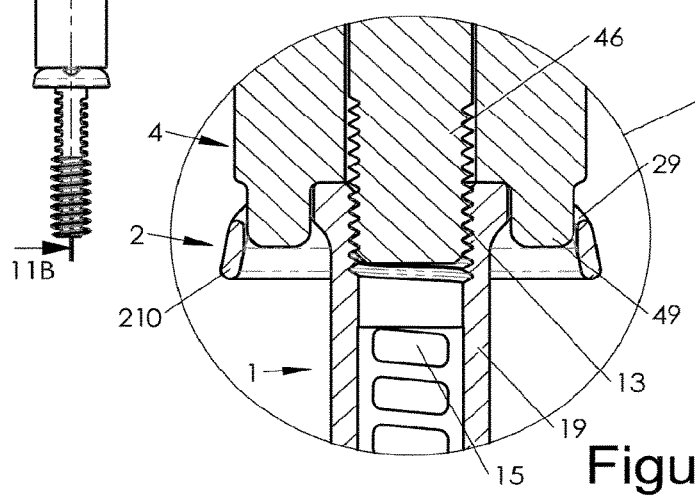

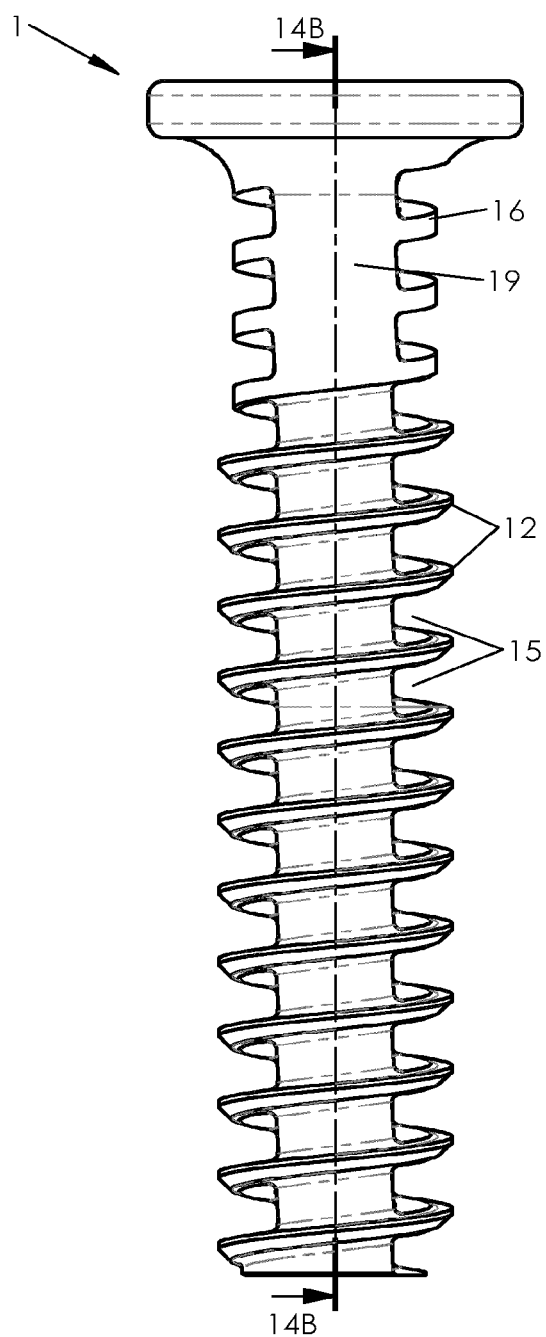
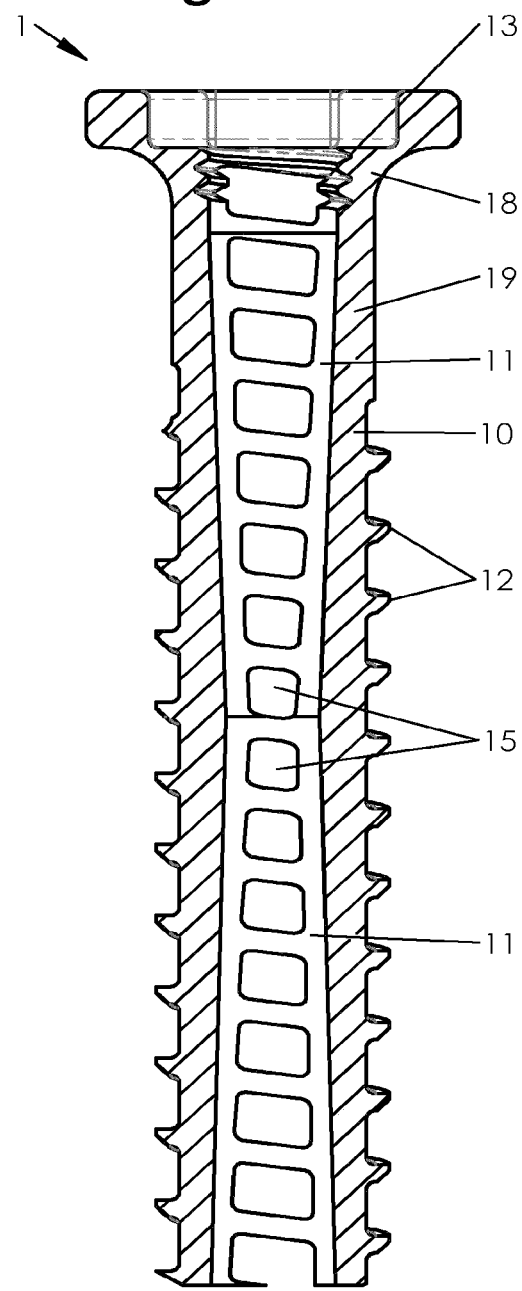

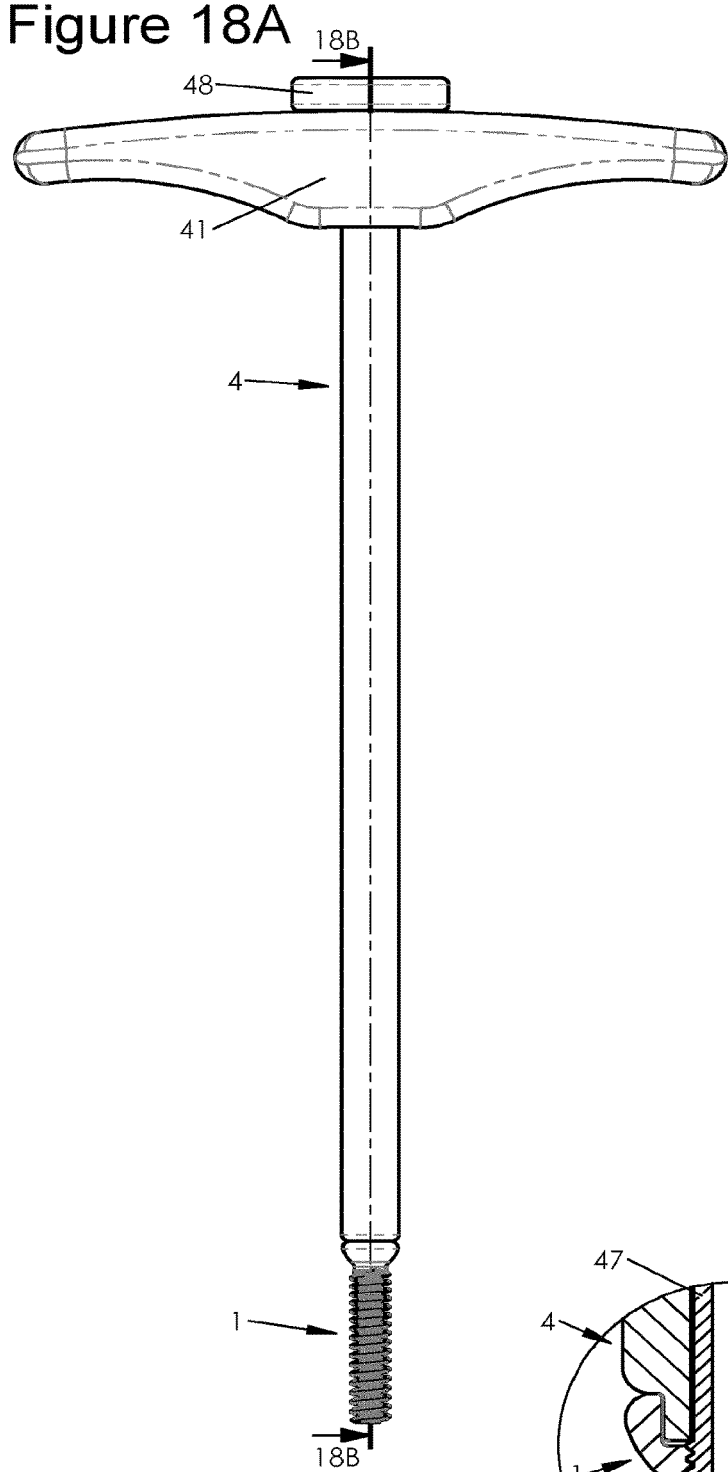
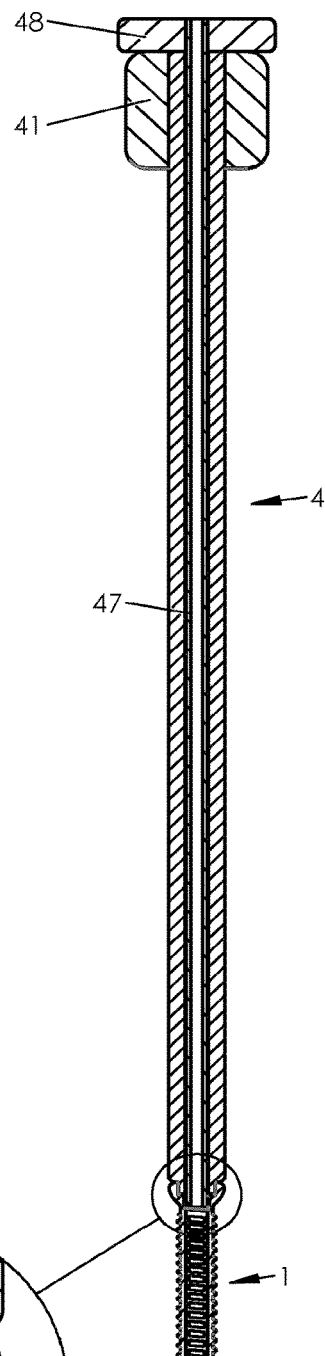
Figure 18A
Figure 18B
Figure 18C

Figure 20A
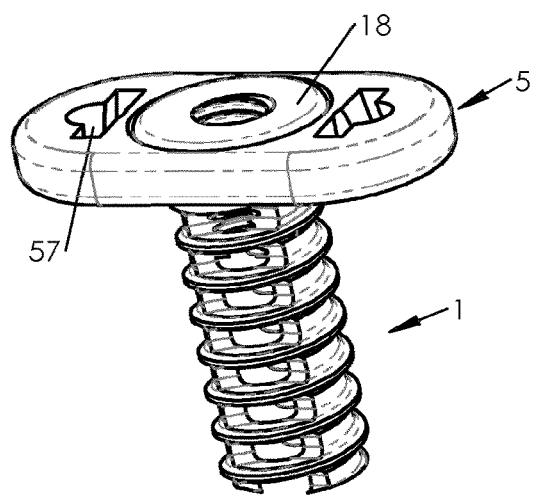
Figure 20B
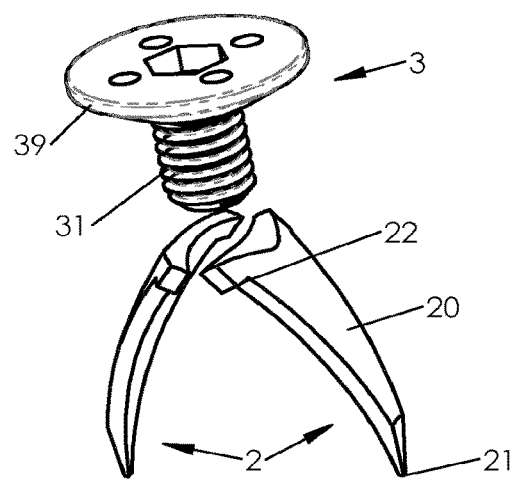
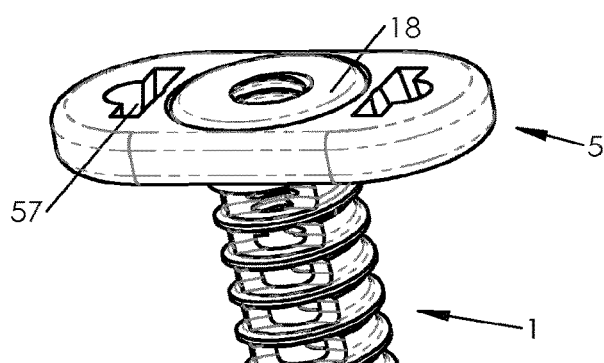
Figure 20C
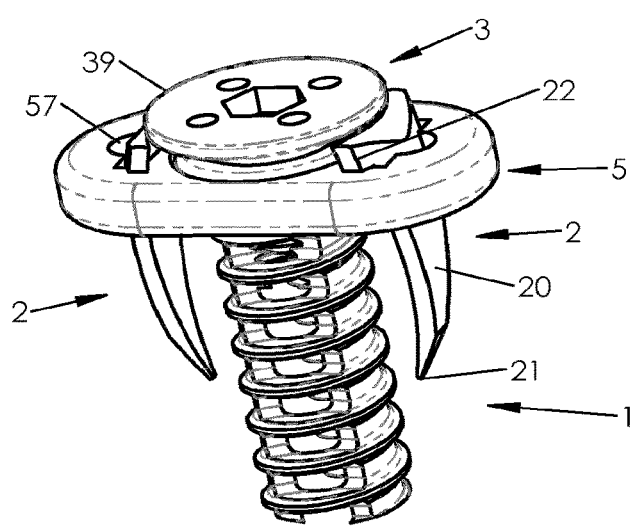

Figure 21A
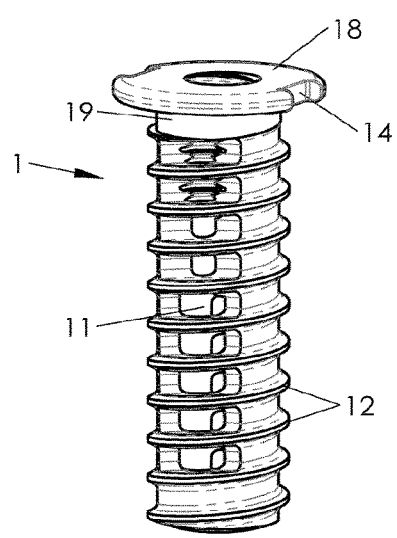
Figure 21B
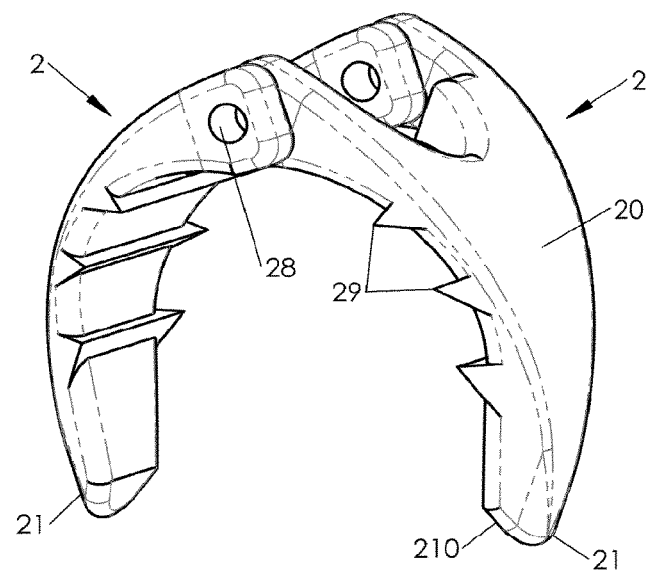
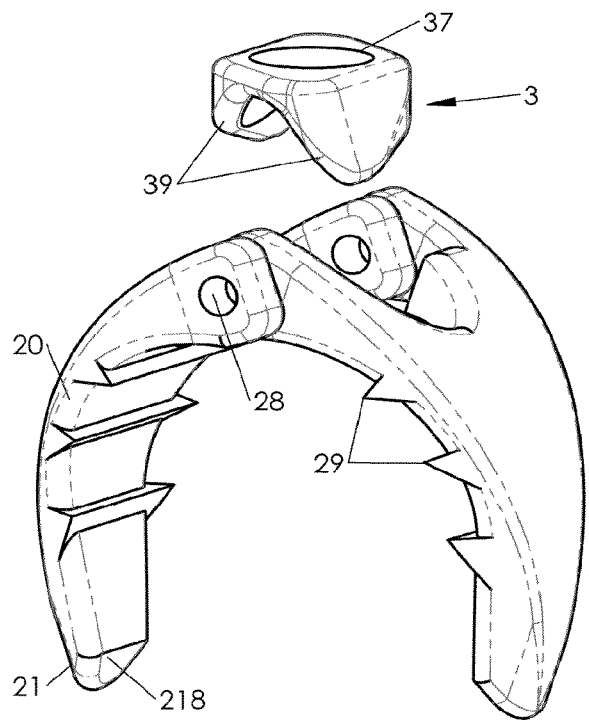
Figure 21C
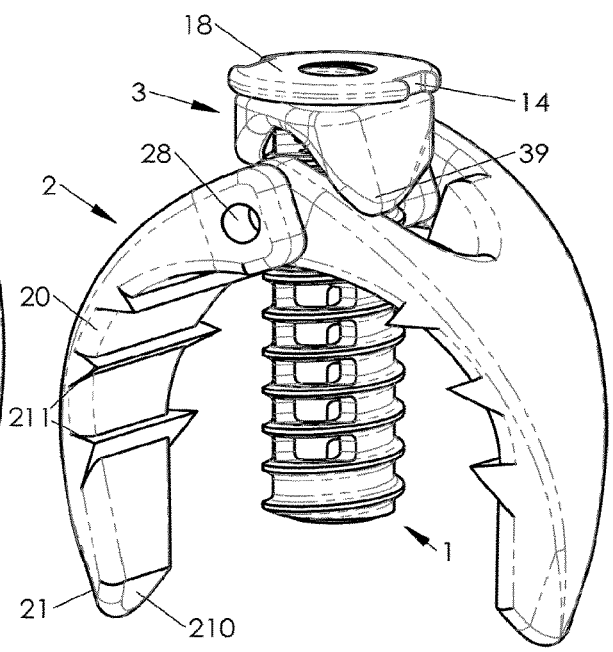

Figure 25A
Figure 25B
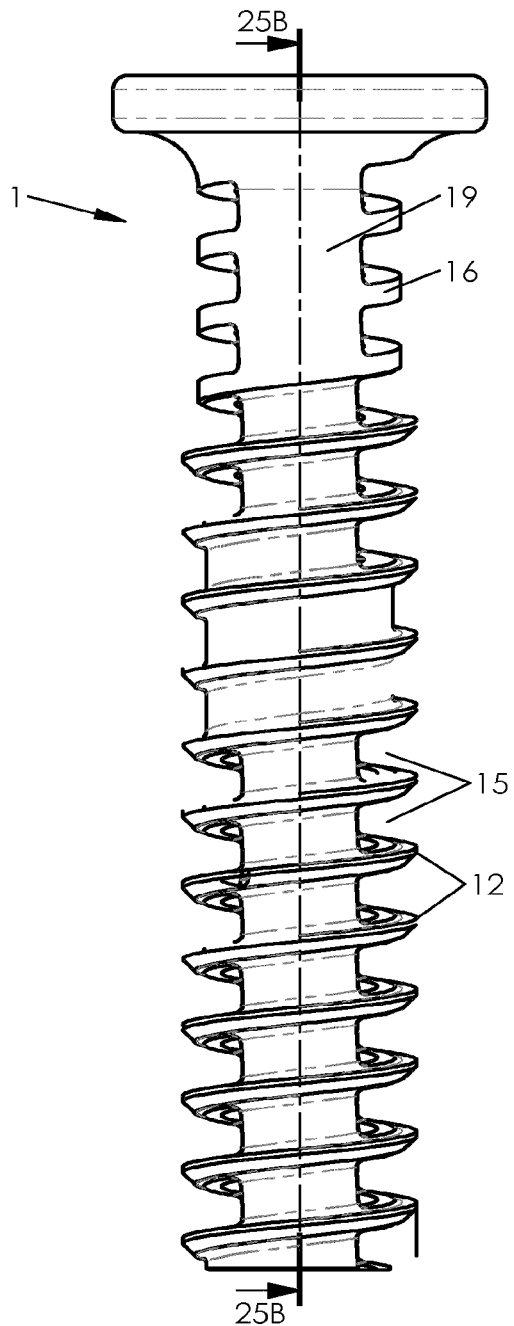
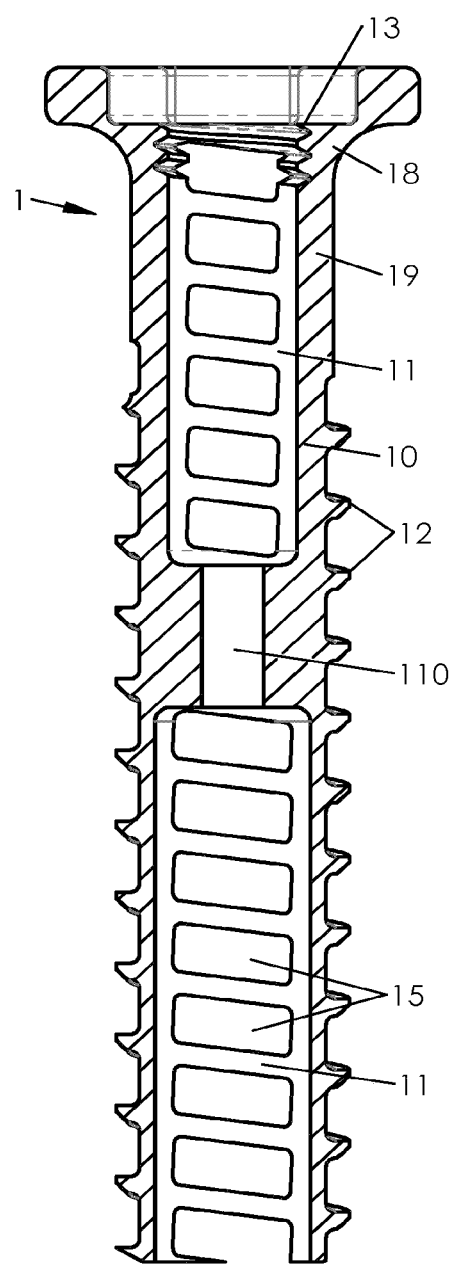

Figure 28A
Figure 28B
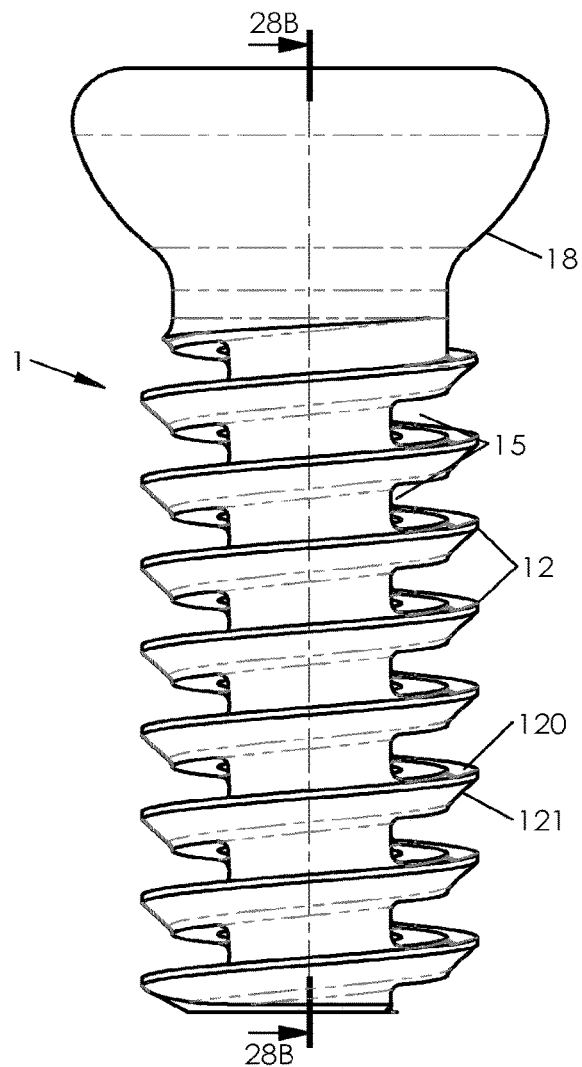
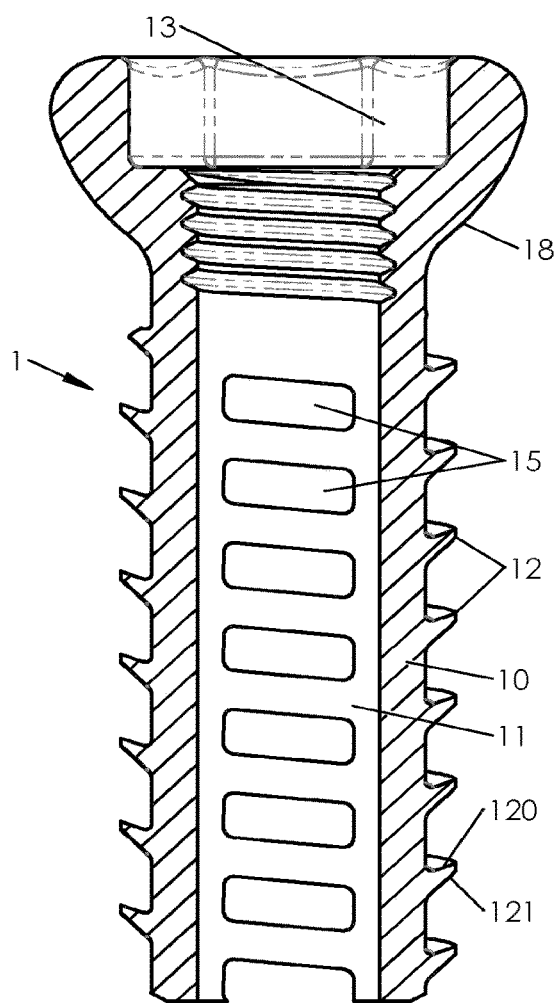

Figure 32A
Figure 32B
Figure 32C
Figure 32D
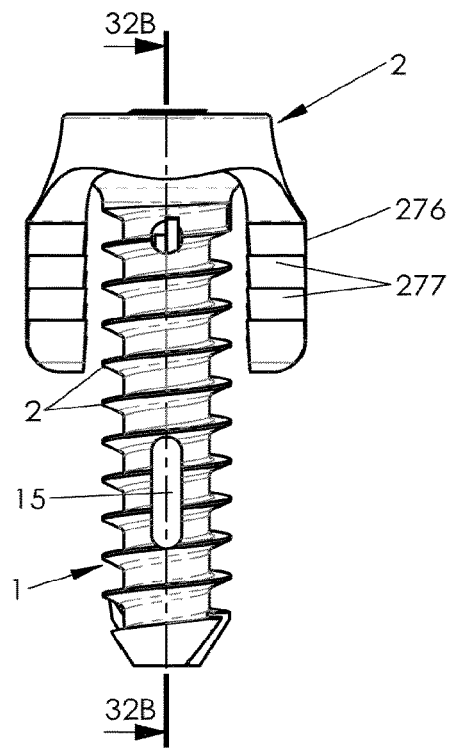
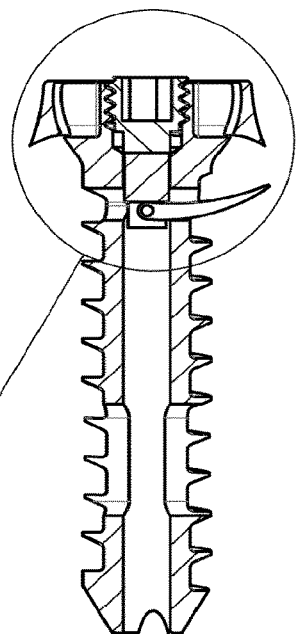
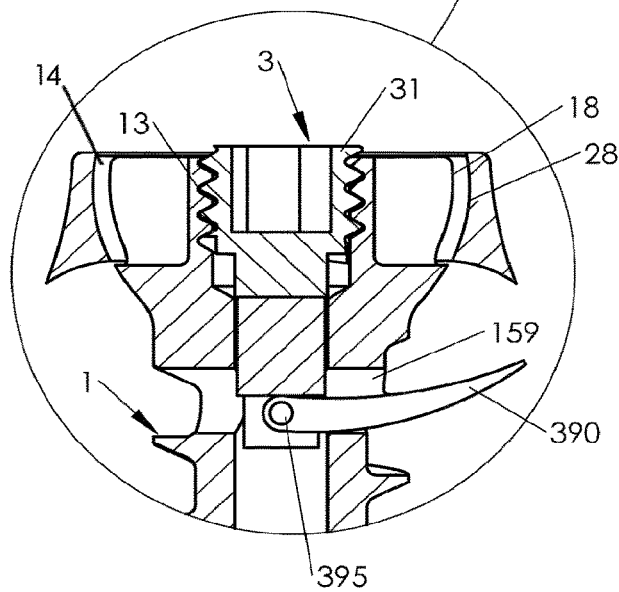
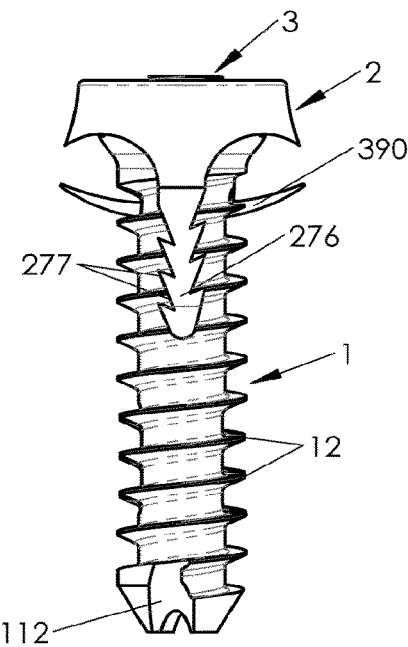

BONE IMPLANTS

CROSS-REFERENCE TO RELATED APPLICATION

This application is a divisional of U.S. patent application Ser. No. 16/881,831, filed May 22, 2020; which is a continuation of U.S. patent application Ser. No. 15/501,166, filed Feb. 1, 2017, now U.S. Pat. No. 10,687,877; which is a national stage application under 35 U.S.C § 371 and claims the benefit of International PCT Patent Application No. PCT/EP2015/067861, filed Aug. 3, 2015, which claims priority to France Patent Application No. 1457539, filed Aug. 1, 2014; the entire disclosures of each of which are hereby incorporated by reference.

TECHNICAL FIELD OF THE INVENTION

The present invention relates to the field of bone implants, in particular spinal implants, for example for arthrodesis of the two vertebral structures. The present invention more particularly relates to spinal implants, notably so called "facet" implants intended to be implanted between the articular facets of the vertebrae (so-called "intra-facet" implants) and/or implanted through these articular facets of the vertebrae (so-called "trans-facet" implants). Various embodiments of the present application are also adapted to implantation in vertebral pedicles (so-called "pedicular" implants) or at the sacro-iliac joint or in various types of bone structures, either spinal or not, although the characteristics of the implants described in the present application make them particularly useful for their use in the rachis.

TECHNOLOGICAL BACKGROUND OF THE INVENTION

A problem in the field of implants relates to bone growth and notably arthrodesis, i.e., the bone merging of two structures, such as for example vertebrae. Indeed, it is sometimes sought to obtain merging of at least two vertebrae for example when at least one of their adjacent intervertebral discs is lesioned. Various arthrodesis techniques are known from the prior art, based on various types of implants such as for example intersomatic cages (or arthrodesis cages) inserted in the place of a disc in order to promote bone growth, or arthrodesis plates attached on both vertebrae in order to immobilize them and allow arthrodesis, or further osteosynthesis or arthrodesis rods, used for immobilizing the vertebrae, to which they are generally connected through pedicular screws or hooks, or finally inter-spinal implants inserted between the spines of the vertebrae (or "spineous apophyses") for immobilizing them and thereby facilitating merging. These types of implants aim at finding an answer to a problem known in the field which is to stabilize the vertebral level to be treated. Solutions are also known, notably at the lumbar and sacral level, using facet implants allowing such stabilization, by attaching the articular facets with the purpose of obtaining merging. For example, implants are known from the prior art, such as for example from patent FR2726171B1, in the form of a hollow cylinder provided with threading for screwing bones, forming a screw in which a conduit and grooves are made in order to provide a grafting space allowing the insertion of tissue or bone substitute or cement for facilitating the merging of the structures in which the screw is implanted.

It will be noted that vertebral articular apophyses (or articular processes or pedicular facets) are designated here by the term of "articular facet", since each vertebra is jointed with the one above and below through articular facets which are posterior and the invention is useful for treating these articular facets, but it is possible to optionally use various embodiments on other structures, notably vertebral structures, such as for example costal or sacro-iliac facets if need be. Articular apophyses protrude above and below the base of transverse apophyses of the vertebrae, behind the pedicles. At the lumbar level for example, the upper articular apophyses are separated from each other by a more considerable distance than that which separates the lower two. The articular facets which they support have the shape of a vertical gutter, the concavity of which faces rearwards and inwards, a gutter in which will be placed the lower articular apophyses, which have a convex articular surface in the opposite direction, i.e., forwards and outwards. The lower articular apophyses provide a convex articular surface in the form of a cylinder segment, which faces outwards and slightly forwards. This surface slides in the concavity of the upper articular apophysis of the vertebra located below. These structures are therefore important for the stability of the vertebrae one on the other and it will moreover be noted that the bone deficit (or "lysis") of the isthmuses (or "pars interarticularis") located at their base is often responsible for spondilolysthesis (the sliding of a vertebra relatively to the other adjacent ones) which generally lead to degeneration of intervertebral discs. When it is sought to achieve vertebral arthrodesis, it is therefore sometimes desirable to use a facet implant for attaching the lower articular apophyses of a vertebra to the upper articular apophyses of the adjacent vertebra. These facet implants may either be "inter-facet" implants, i.e., they are inserted between the articular surfaces, or "trans-facet" implants, i.e. they are inserted through the articular apophyses for attaching the articular surfaces together. Inter-facet implants are generally set into place in the articular joint by identifying the approach axis and for example by positioning a broach used as a guide for the implant, which is often cannulated (i.e. hollow). A problem in the field relates to the solidity since it is desirable to guarantee the integrity of the implant in spite of its small size and its often recessed layout.

A problem relating to implants in general, in particular spinal implants and notably facet implants, relates to the stability of the implant. It is required that an implant be stable in its implantation site, in particular when arthrodesis is desired since the latter should take place in a relative position of the elements of the rachis, which is optimum. Stabilization and/or locking of the implant is(are) therefore often preferable. Another general problem relates to the ease and/or the rapidity of the implantation. Further, it is generally desired that the implants may be implanted with minimum invasiveness, i.e. it is sought to limit the size of the incisions and of the damages on the surrounding tissues. Percutaneous solutions or only requiring a few millimeters of incision (for example 2 to 40 mm) are often sought. Further, it is generally desirable to limit resorting to imaging in order to avoid exposing the patients to rays.

Intra-facet implants, often accompanied by other problems such that, for example, the requirement of providing the graft or bone substitute or cement for facilitating the merging, for example by means of the presence of a grafting chamber in the implant, in spite of its small size, and by maintaining sufficient rigidity of the implant in order to support the forces between both fixed facets. Further, it is generally desirable to tap, clean out or sharpen the articular surfaces, for example in order to remove cartilage and/or promote bone growth. Transfacet implants, which often provide the advantages of being simple, being able to be used percutaneously and allowing compression of articular facets against each other, are often accompanied by other problems such as for example, the lack of sharpening, cleaning or tapping of the articular joints, which limits the bone growth rate. These implants generally include at least one implanted screw with an aim through articular surfaces (transfacet). They are generally also guided by a broach but they generally require that the bone be perforated beforehand, often percutaneously by means of a bit. It is possible to tap the bone around the broach in order to screw in the implant (often "cannulated", i.e. hollow and slipped around the broach) which generally includes a bone thread (e.g., a threading adapted for screwing into bone tissue), for example for not risking any fracturing of the facets during the setting into place. Finally, it is generally desirable that these implants include a stabilization means (of either one of the facet or both facets) and/or a compression and/or locking means and/or bone supporting means which will spread the loads over at least one of the facets (notably the posterior facet) at the end of the screwing.

The diversity of the problems, notably of those discussed above, is generally accompanied by the problem that a same implant cannot be equally used as a transfacet implant and as an interfacet implant, which forces the provision of various types of implants and instruments.

In this context, it is interesting to propose a solution with which it is possible to efficiently provide an answer to said at least one portion of these problems.

GENERAL DESCRIPTION OF THE INVENTION

The object of the present invention is to overcome certain drawbacks of the prior art by proposing a bone implant, in particular intended for implantation at articular facets, further allowing stable, easy and rapid implantation.

This aim is achieved by a bone implant including, on the one hand, an elongated body between a free end and a head, along a longitudinal axis and, on the other hand, turns of at least one threading, on at least one portion of said body in proximity to the free end along the longitudinal axis, characterized in that the body includes a longitudinal internal conduit, on at least one portion along the longitudinal axis, obtained by at least one first central machining parallel to the longitudinal axis, and at least one second machining in a plane, a so called transverse plane, not parallel to the longitudinal axis, and crossing the walls of the body as far as the longitudinal internal conduit by making windows communicating between said longitudinal internal conduit and the outside of the body.

Advantageously, these windows can be made so that the size of the implant transversely to the longitudinal axis is locally reduced.

In addition, these windows can advantageously be made so as to preserve at least one portion of said turns and the wall of the body behind the turns, and by preserving a non-machined portion on the perimeter of said body.

This aim is also achieved by a bone implant including, on the one hand, an elongated body between a free end and a head, along a longitudinal axis and, on the other hand, turns of at least one threading, on at least one portion of said body in proximity to the free end along the longitudinal axis, characterized in that, on the one hand, the body includes a longitudinal internal conduit on at least one portion along the longitudinal axis and windows communicating between said longitudinal internal conduit and the outside of the body and, on the other hand, said windows have at least one sharpened outer edge.

This aim is also achieved by a bone implant including, on the one hand, an elongated body between a free end and a head, along a longitudinal axis and, on the other hand, turns of at least one threading, on at least one portion of said body in proximity to the free end along the longitudinal axis, characterized in that, on the one hand, the body includes a longitudinal internal conduit on at least one portion along the longitudinal axis and windows communicating between said longitudinal internal conduit and the outside of the body and, on the other hand, the head of the implant is provided with stabilization means of the implant, intended to bear upon the bone tissue around said head.

This type of solutions have the advantage to allow a use as either a transfacet implant or as an interfacet implant, for example thanks to the fact that the implant offers a large bony graft space in its internal conduit and/or that the bone will be of the for example by the fact that the implants provides a wide space for bone grafting in its internal conduit and/or that the bone will be sharpened or edged by the passage of the implant and/or that the stability of the implant is improved relatively to the known solutions.

According to another feature, said free end of the body is self-drilling.

According to another feature, said body is substantially cylindrical.

According to another feature, said body is substantially conical of frusto-conical.

According to another feature, the perimeter of said threading is substantially cylindrical in spite of the conical or frusto-conical shape of the body.

According to another feature, said windows are aligned with each other along a longitudinal axis.

According to another feature, said windows are shifted relatively to each other along the longitudinal axis.

According to another feature, said windows are flared so that they have at least one sharpened outer edge.

According to another feature, said head of the implants closes the longitudinal internal conduit or includes means for closing the longitudinal internal conduit.

According to another feature, said thread has a variable pitch becoming shorter in the direction of the head.

According to another feature, said body is provided with several threads with different pitches, the pitch of a thread located on the side of the free end being of a larger size than the adjacent thread located on the side of the head.

According to another feature, said head of the implant is provided with stabilization means of the implant, intended to bear upon the bone tissue around said head.

According to another feature, said stabilization means include at least one stabilization element forming a kind of staple comprising at least two rods substantially parallel to the longitudinal axis and able to penetrate the tissue around the head and optionally a portion of said body in proximity to said head.

According to another feature, said rods of the stabilization element have a pointed free end.

According to another feature, said rods are connected together through a ring making the stabilization element able to be mounted on said head.

According to another feature, said head includes at least two notches able to receive said rods or shoulders positioned along said rods in order to maintain them at a distance from the body.

According to another feature, said stabilization means include at least one bell-shaped stabilization element mounted on the head and the perimeter of which is intended to bear upon the bone tissues surrounding the head.

According to another feature, said bell includes at least one tip or tooth on its perimeter for facilitating bone anchoring.

According to another feature, said bell is mounted secured to the head.

According to another feature, said bell is movably mounted on said head.

According to another feature, said head has a peripheral lower surface with the shape of a spherical portion and mating an internal upper surface of said bell thereby jointed on the head of the implant.

According to another feature, said stabilization means include at least one plate mounted around the head and provided at least with one passage able to receive a stabilization element, a so-called anchor, with a shape of the plate able be anchored in the bone tissue around the head.

According to another feature, said anchor includes a pointed end and/or sharpened end intended to penetrate the bone tissue.

According to another feature, said anchor includes an end provided with at least one abutment intended to come into contact with said plate and limit the penetration of the anchor onto the bone tissue.

According to another feature, said anchor is formed with a substantially planar plate.

According to another feature, said anchor is formed with a substantially curved plate.

According to another feature, said anchor and said passage are laid out for inserting the anchor along an oblique axis relatively to the longitudinal axis, so that the anchor is oriented from the center towards the periphery of the implant upon insertion.

According to another feature, the stabilization means include at least one stabilization element in the form of a jaw comprising two curved bits each comprising a free end and jointed together by two joints separated from each other by a space substantially equal to the size of the head so that the jaw may be mounted around the head and the bits may come into contact with the bone tissues around the body of the implant.

According to another feature, the bits of said jaw include on their concave face, at least one catch for stabilizing them against the bone tissue.

According to another feature, the free end of the bits includes at least one chamfer facilitating the opening of the jaw upon inserting the implant into the bone tissue.

According to another feature, stabilization means include locking means bearing upon the stabilization element for maintaining it pressed against the bone tissue.

According to another feature, at least one portion of said widows are separated by at least two turns without any windows.

According to another feature, at least one portion of said windows are made on several turns.

According to another feature, at least one portion of said windows are made between said turns.

DESCRIPTION OF THE ILLUSTRATIVE FIGURES

Figure 1B:
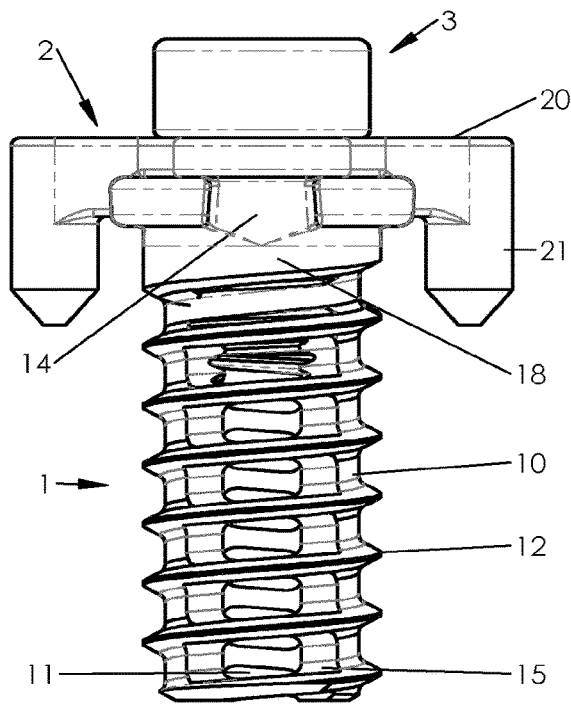
Figure 1C:
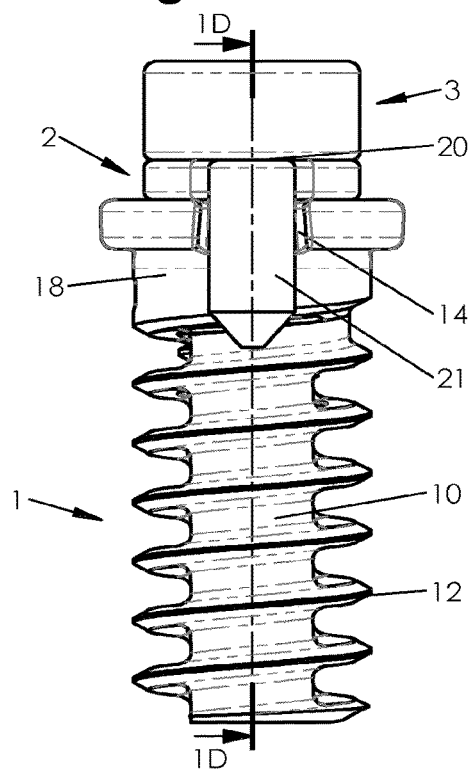
Figure 1D:
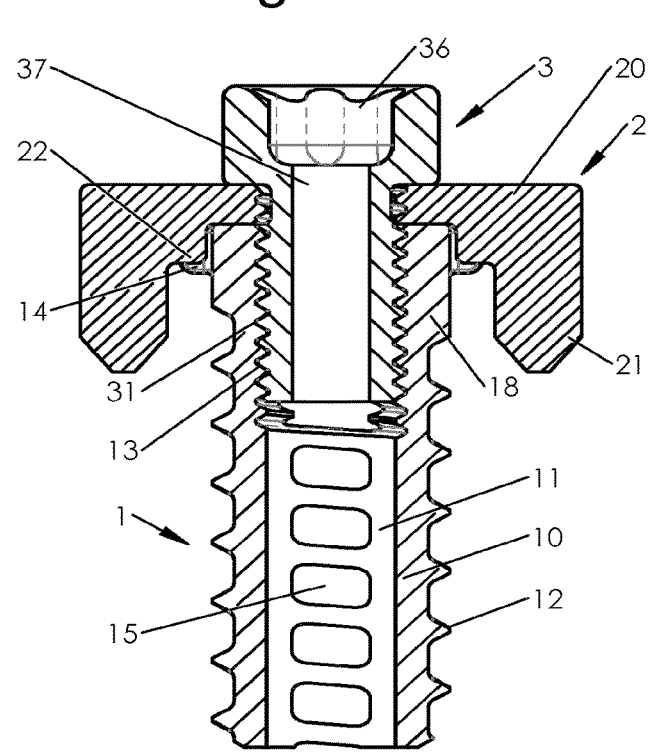
Figure 2A:
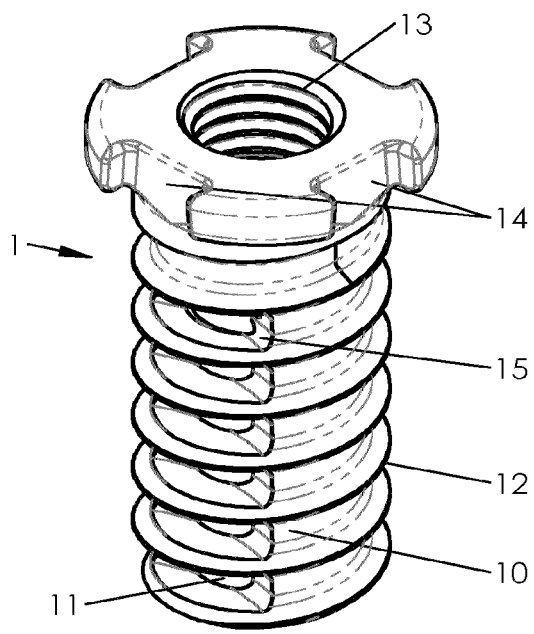
Figure 2B:
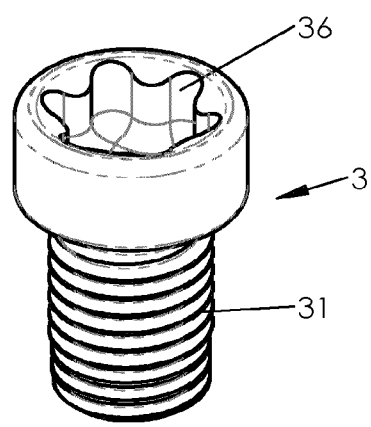
Figure 2C:
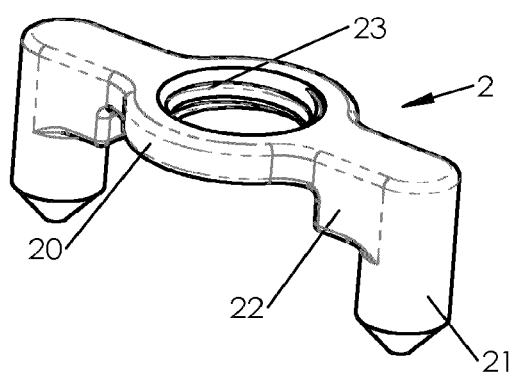
Figure 2D:
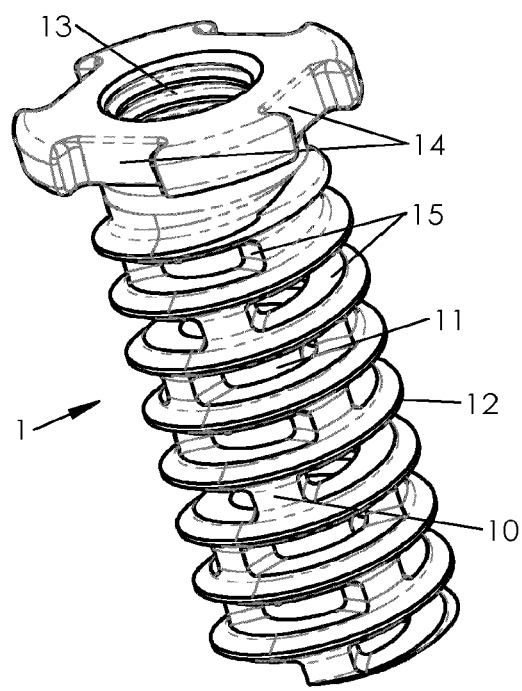
Figure 3A:
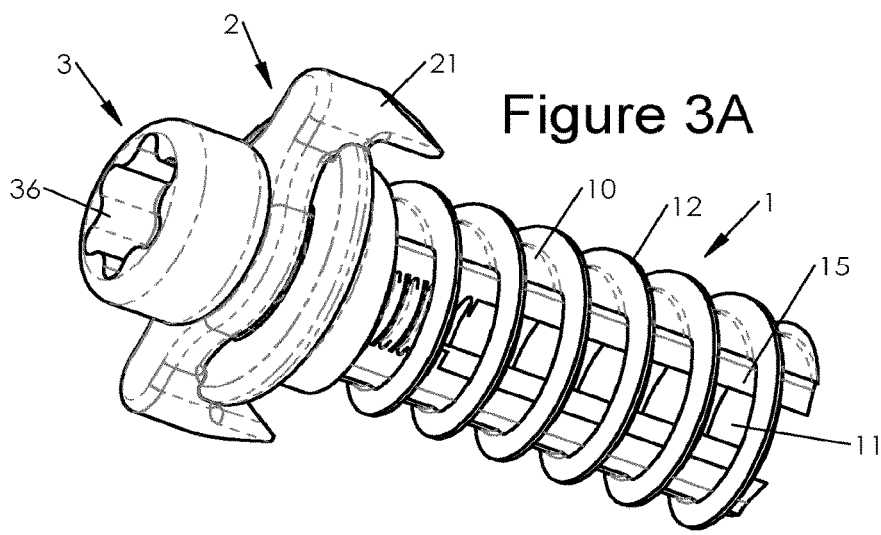
Figure 3B:
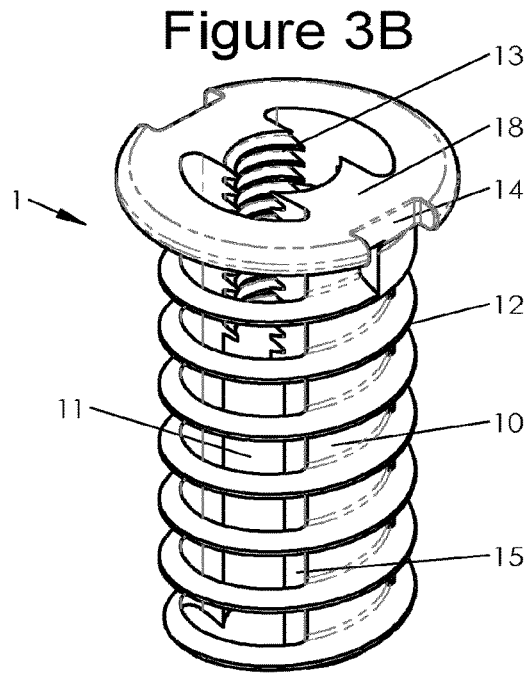
Figure 3C:
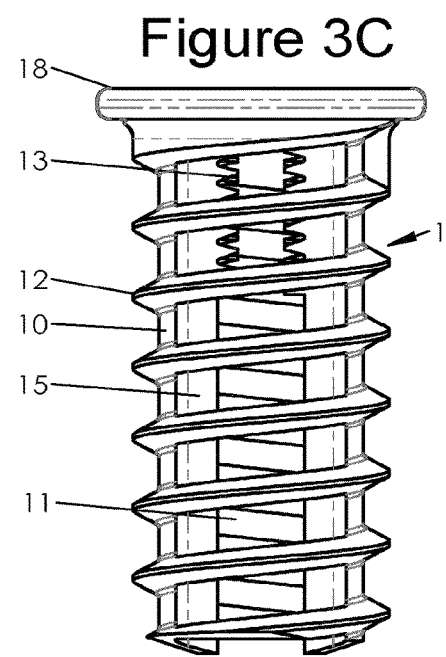
Figure 3D:
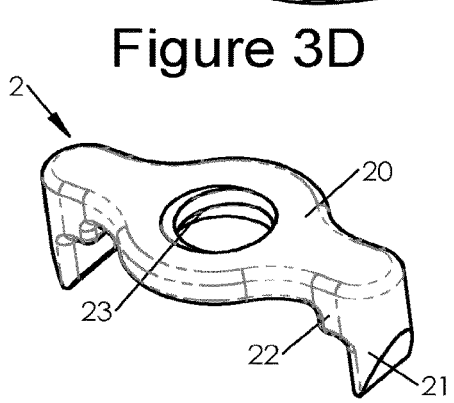
Figure 3E:
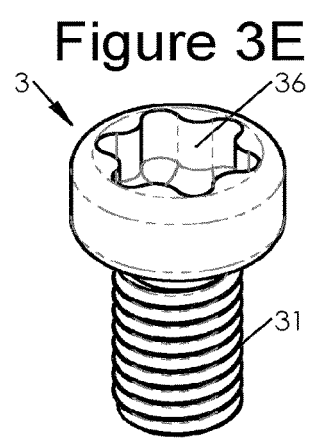
Figure 3F:
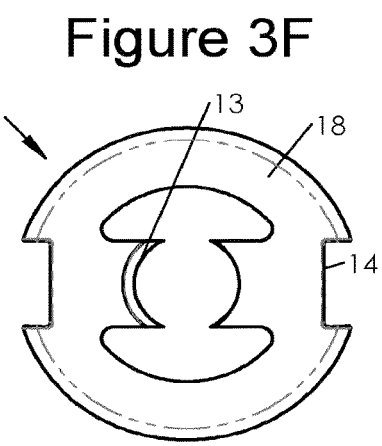

Other particularities and advantages of the present invention will become more clearly apparent upon reading the description hereafter, made with reference to the appended drawings, wherein:

FIGS. 1A, 1B and 1C represent respective, front and profile views, respectively of an implant according to various embodiments, FIG. 1D illustrates a sectional view along the sectional plane 1D-1D of FIG. 1C, FIGS. 2A and 2D illustrate perspective views of an implant according to various embodiments and FIGS. 2B and 2C illustrate perspective views, of a locking means and of a stabilization element, respectively, according to various embodiments, FIG. 3A illustrates a perspective view of an implant provided with stabilizing and locking means according to various embodiments, FIGS. 3B, 3C and 3F illustrate perspective, profile and top views, respectively of an implant body according to various embodiments and FIGS. 3D and 3E illustrate perspective views of a stabilization element and of a locking means, respectively, according to various embodiments, FIG. 4A represents a perspective view of an implant-holder retaining an implant according to various embodiments and FIG. 4B illustrates an enlargement of this implant-holder at its portion retaining the implant, FIGS. 5A and 5B illustrate profile and sectional views respectively along the sectional plane 5B-5B of FIG. 5A, of an implant-holder retaining an implant according to various embodiments and FIGS. 5C and 5D illustrate enlargements of the figures, notably of FIGS. 5A and 5B.

Figure 6A:
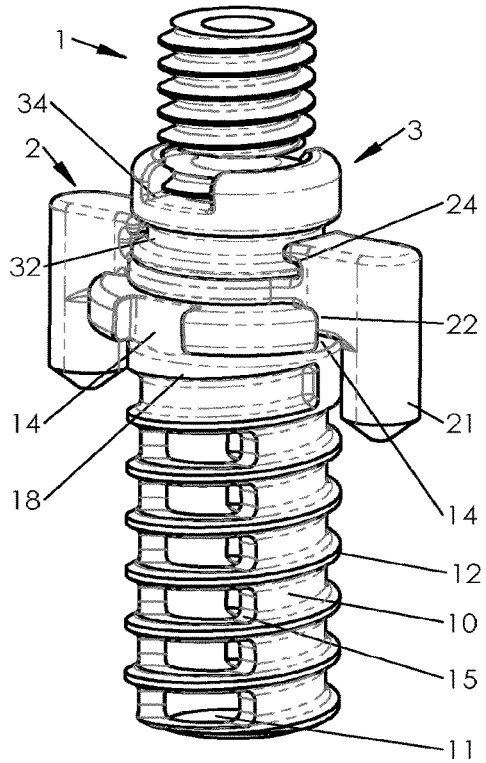
Figure 6B:
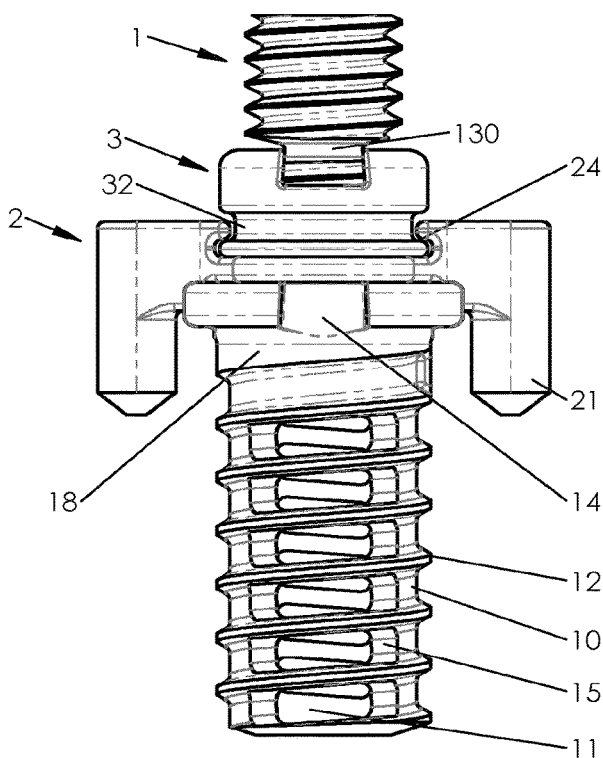
Figure 6C:
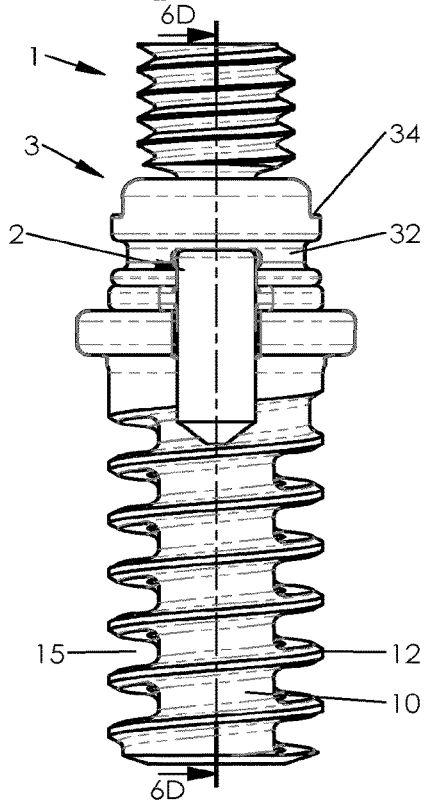
Figure 6D:
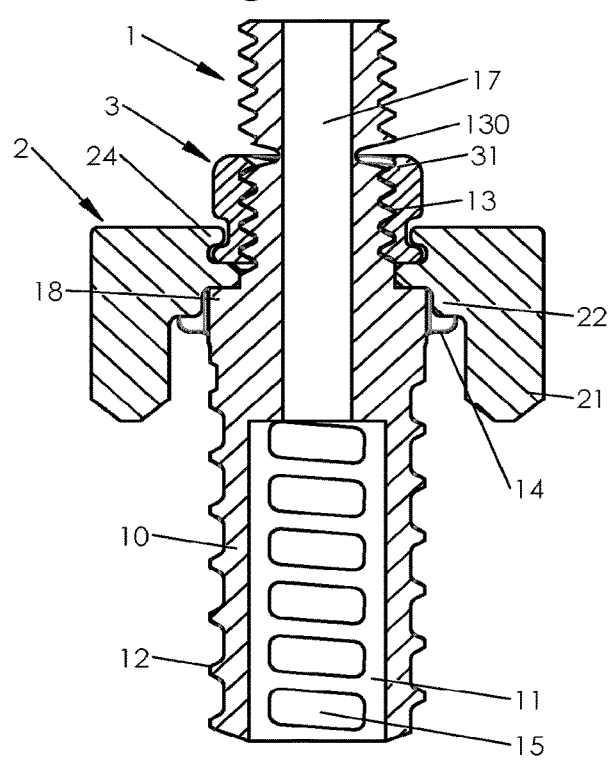
Figure 9A:
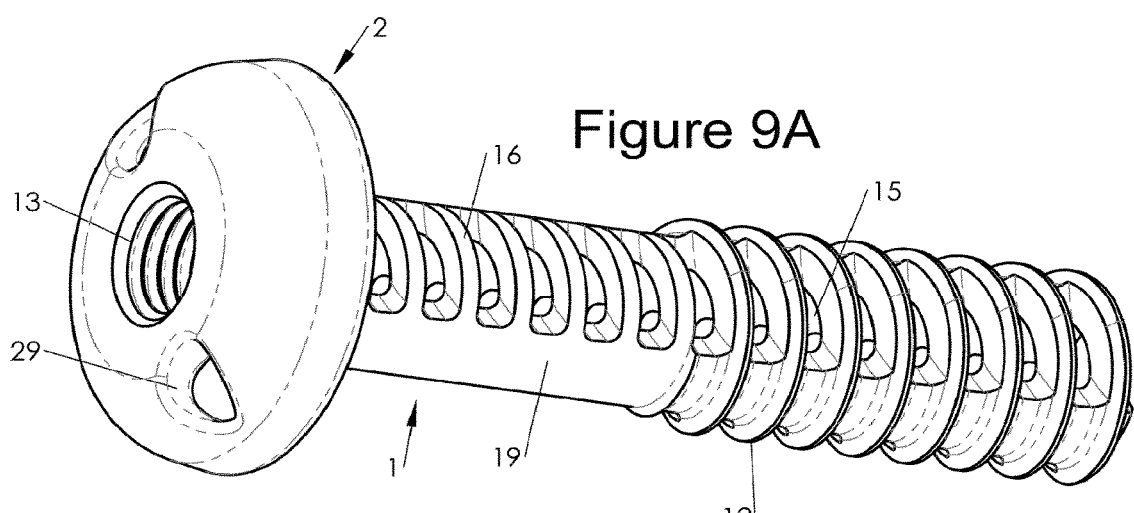
Figure 9B:
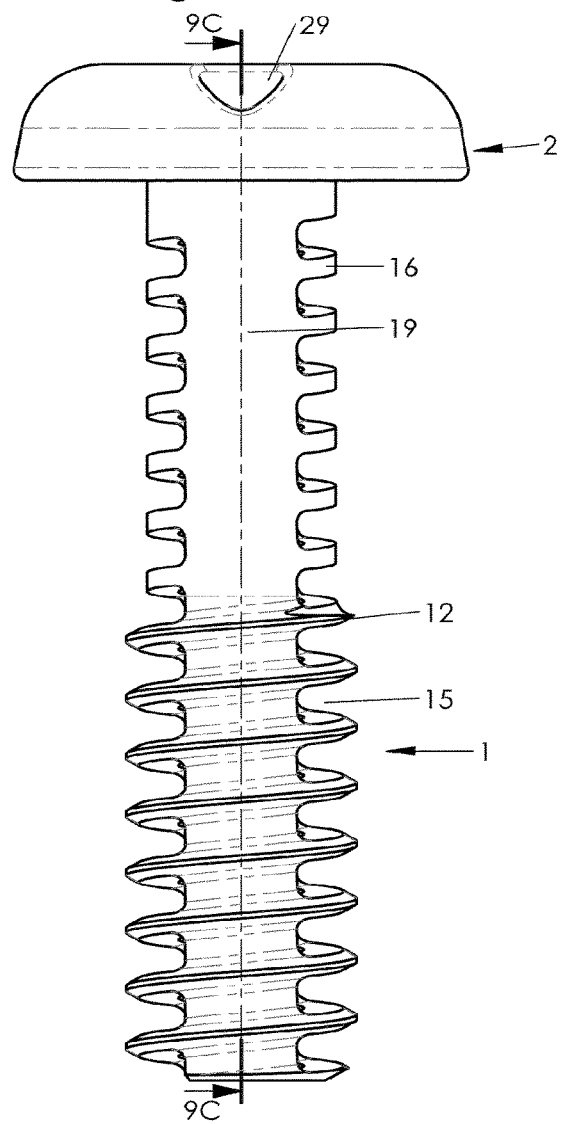
Figure 9C:
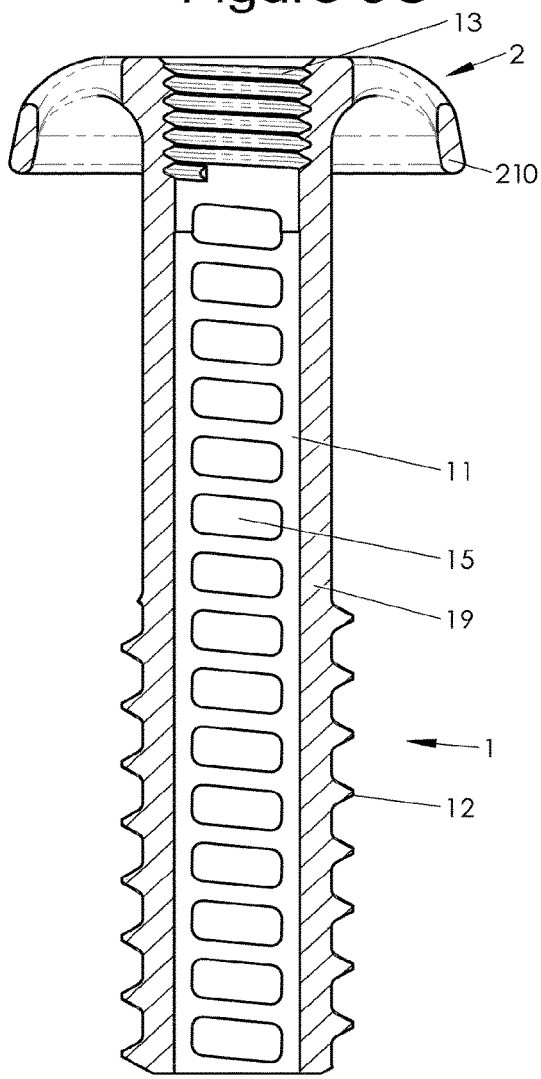
Figure 10A:
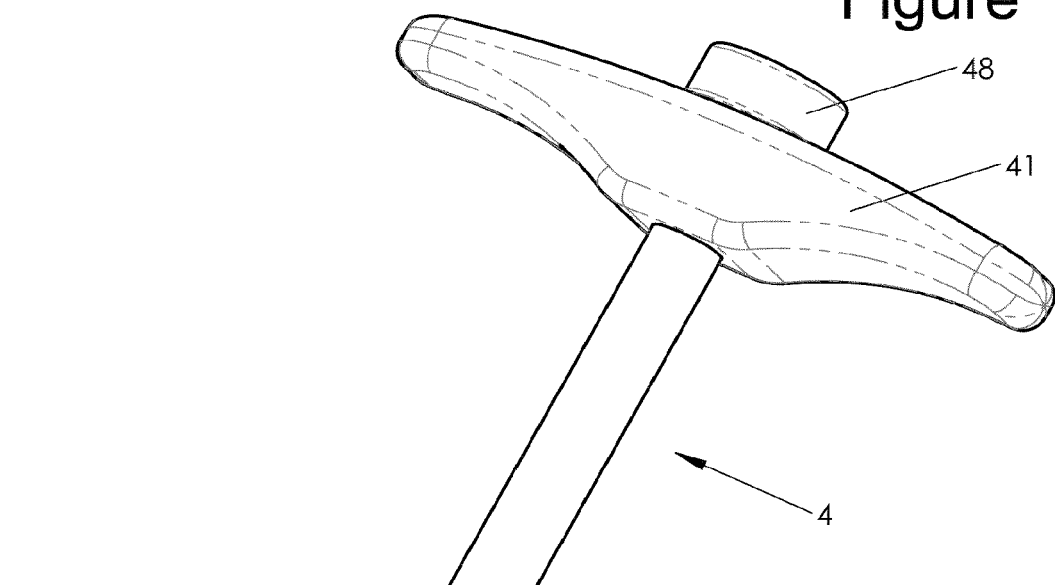
Figure 10B:
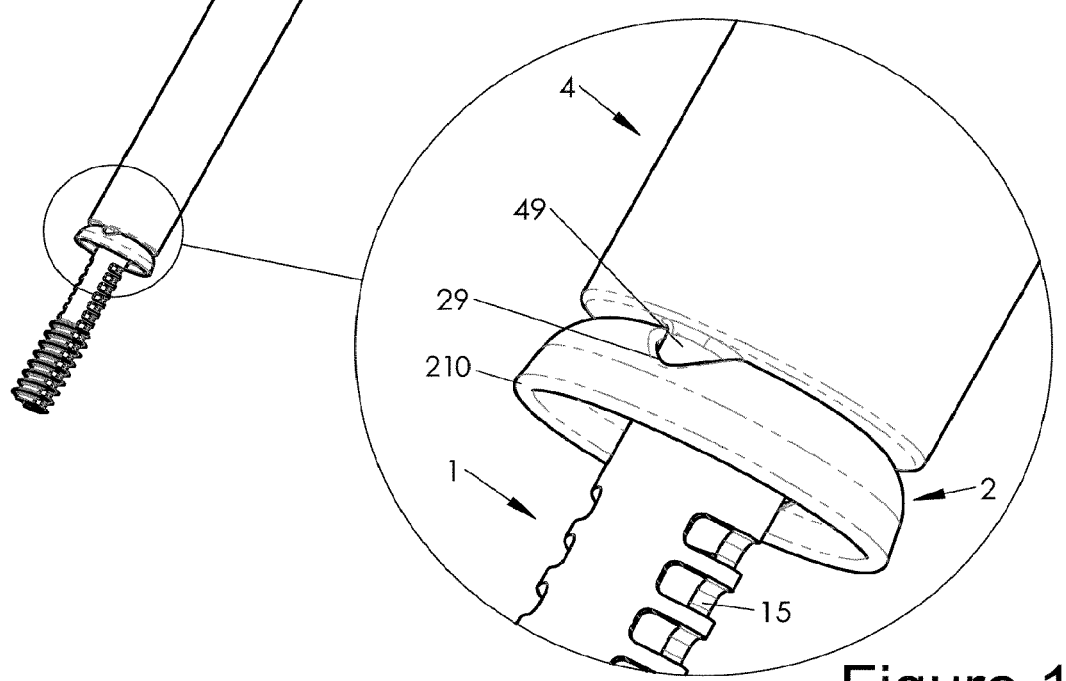
Figure 12A:
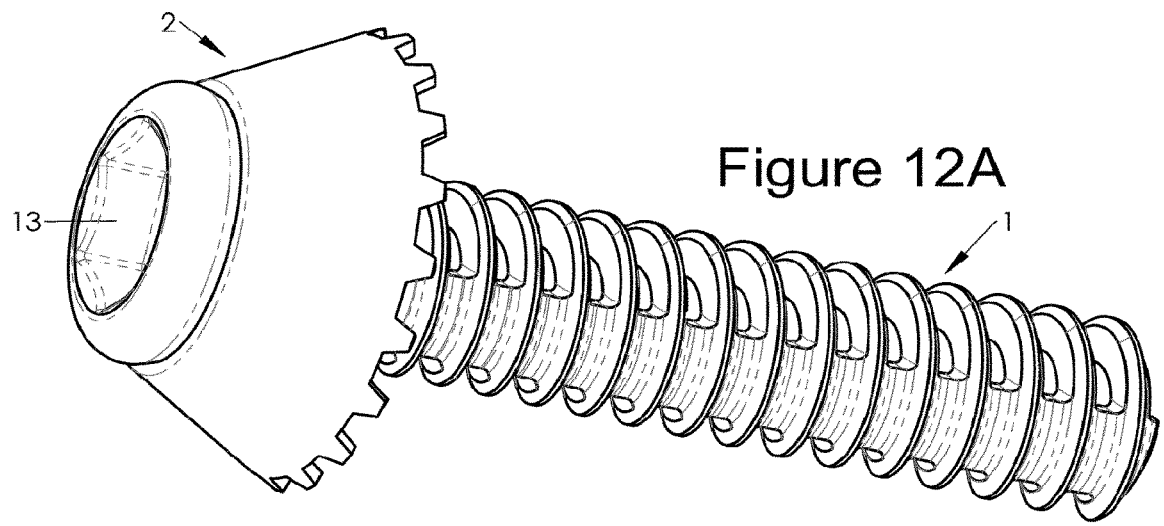
Figure 12B:
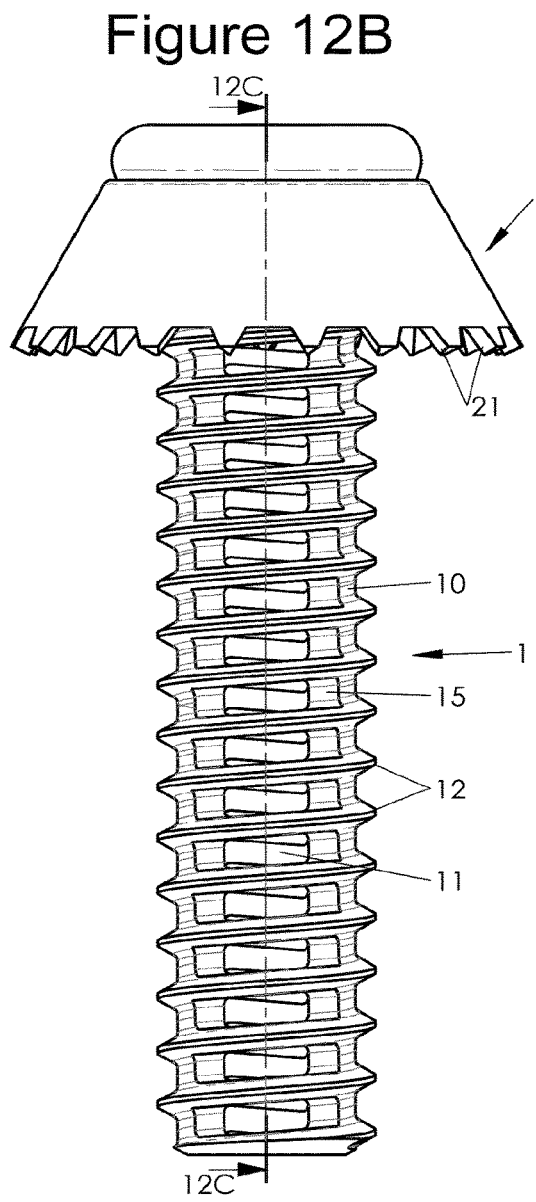
Figure 12C:
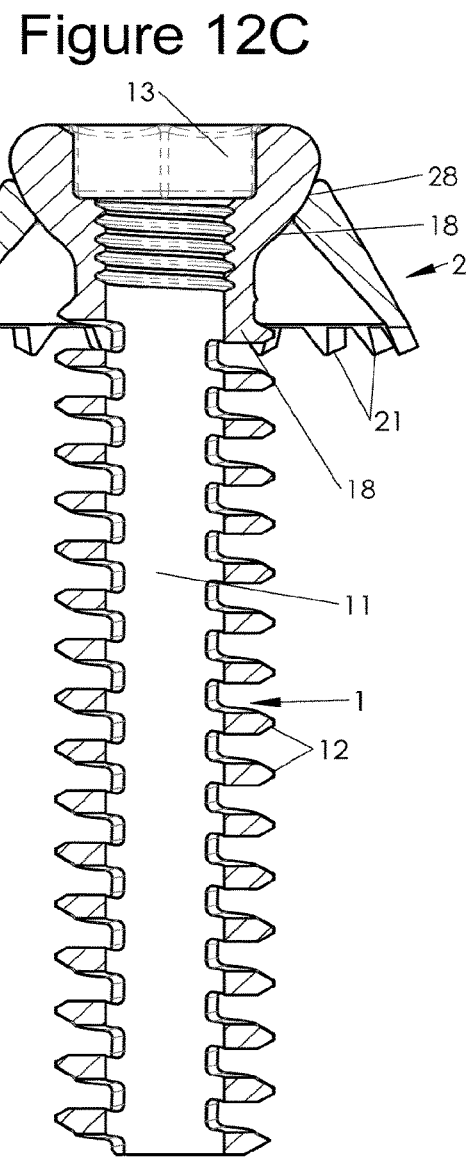
Figure 13A:
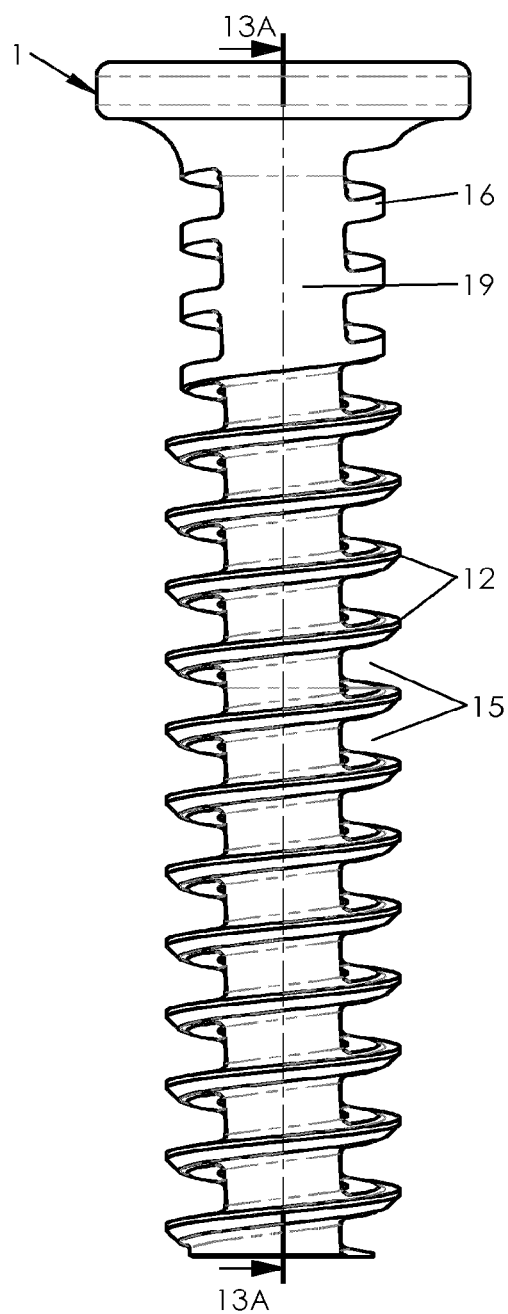
Figure 13B:
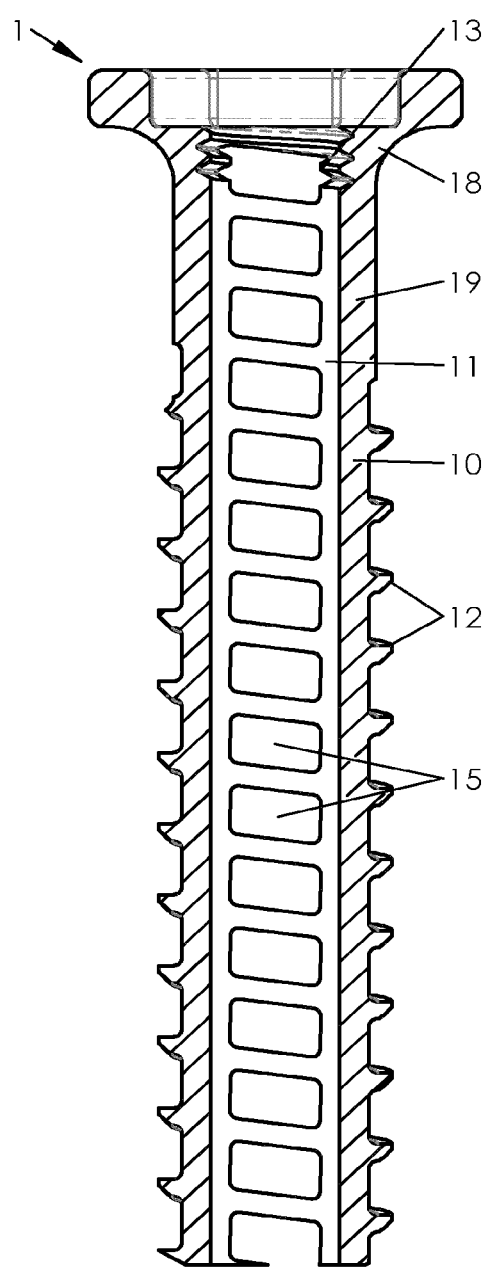
Figure 15A:
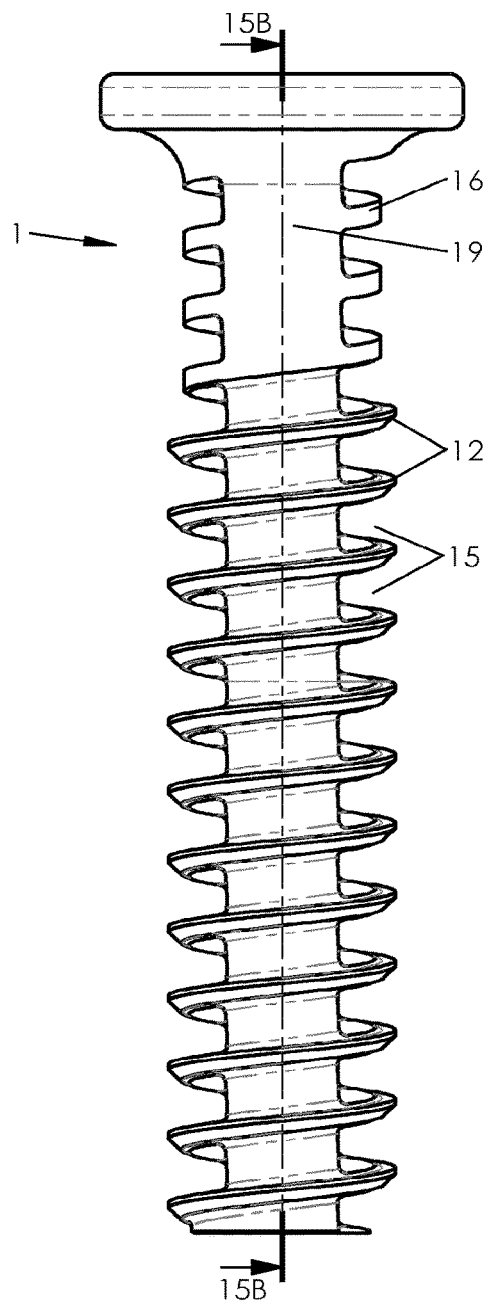
Figure 15B:
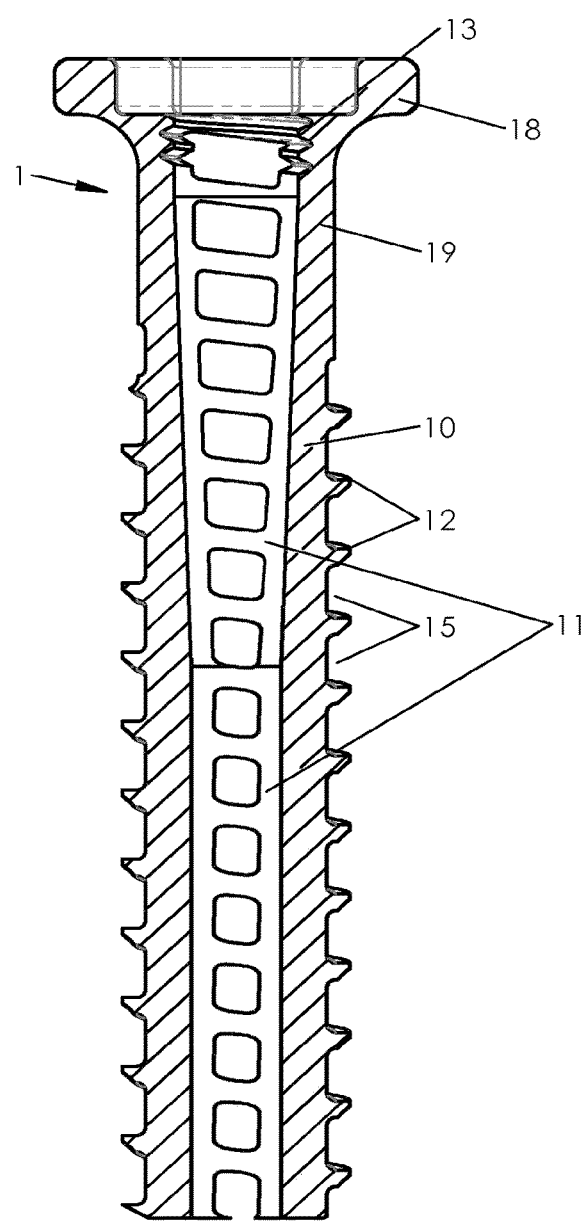
Figure 16A:
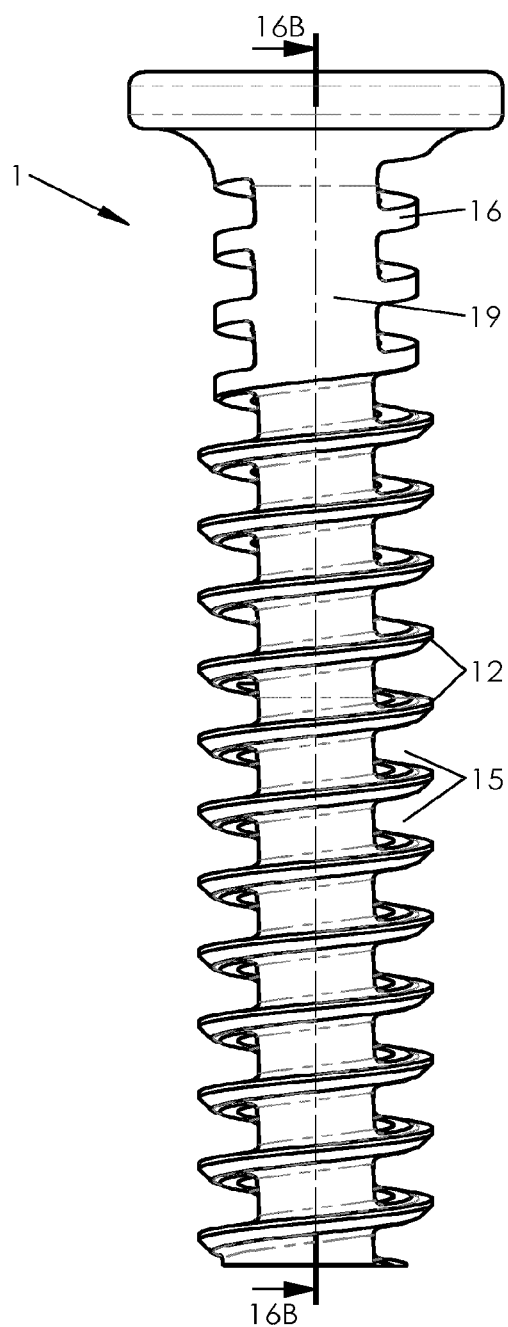
Figure 16B:
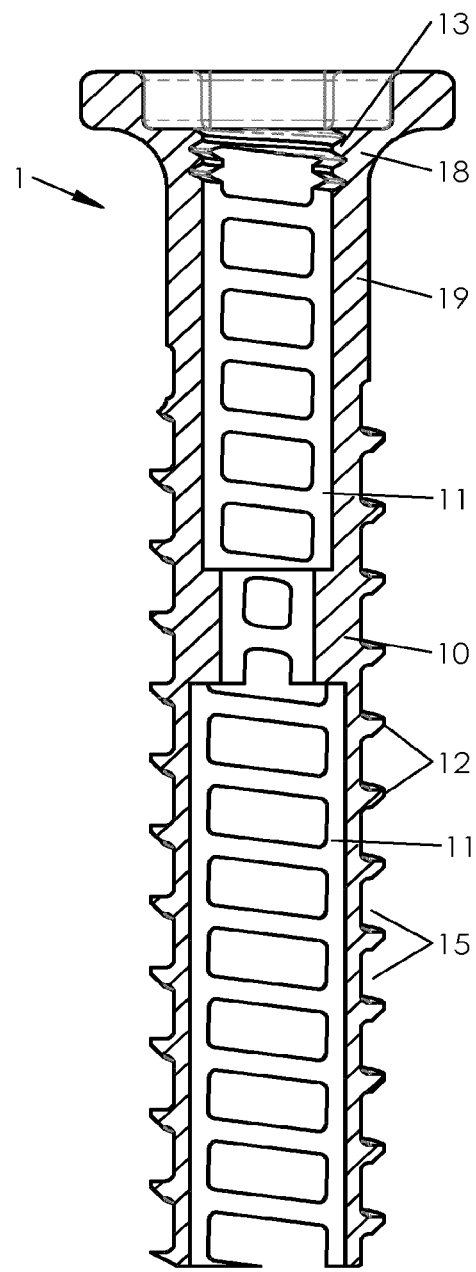
Figures 17A, 17B:
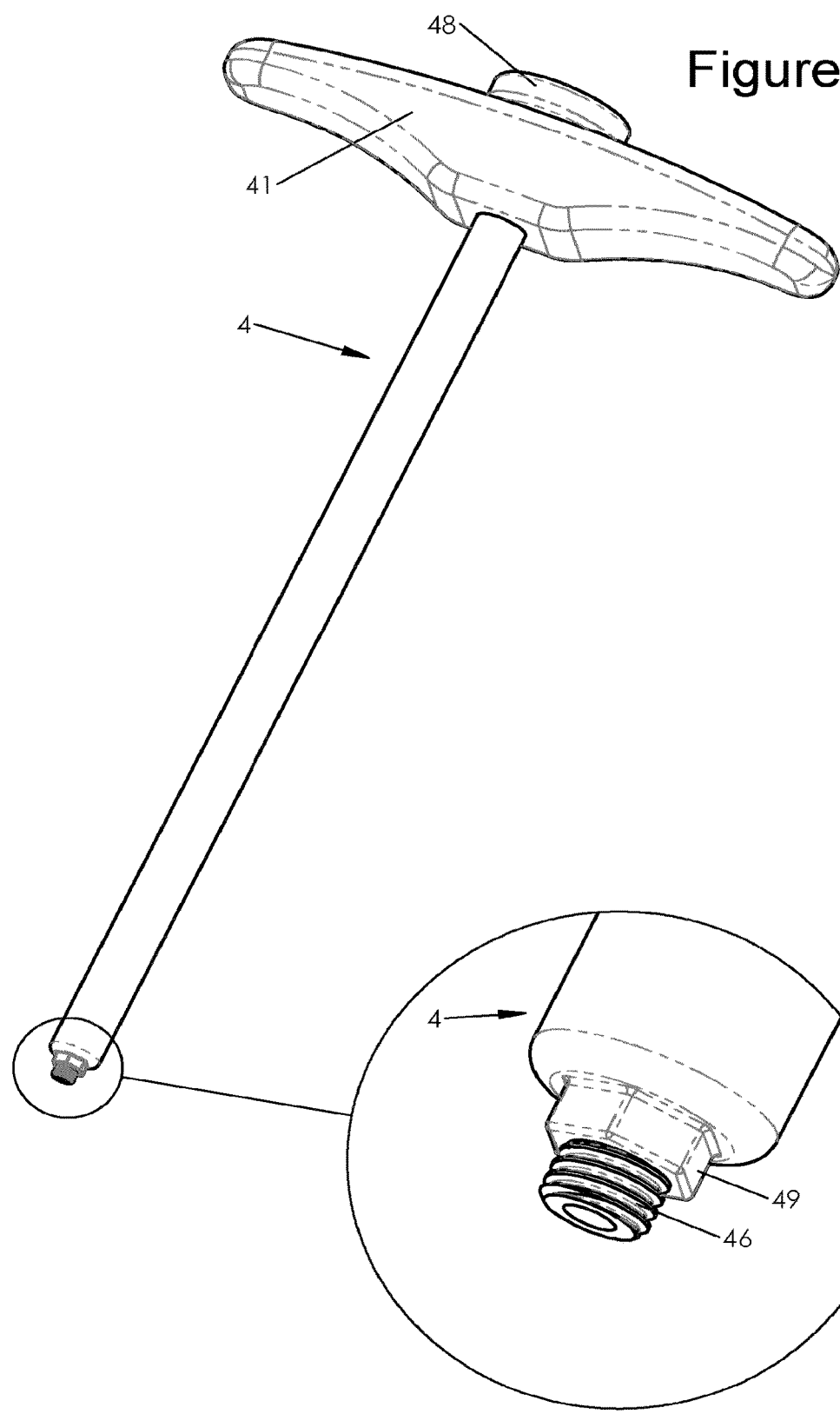
Figure 19A:
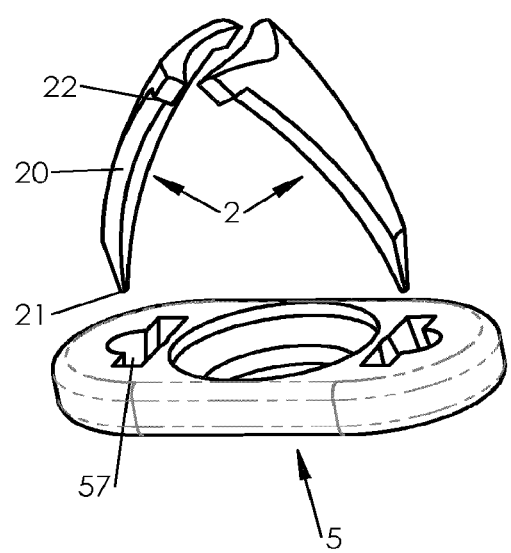
Figure 19B:
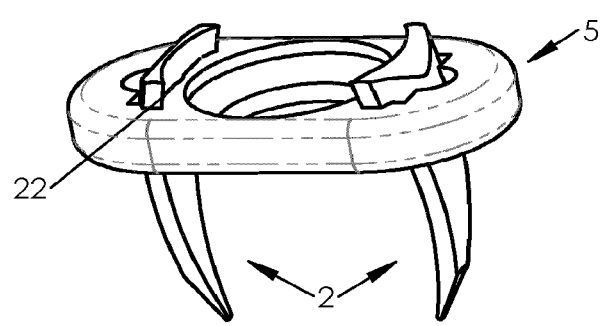
Figure 19C:
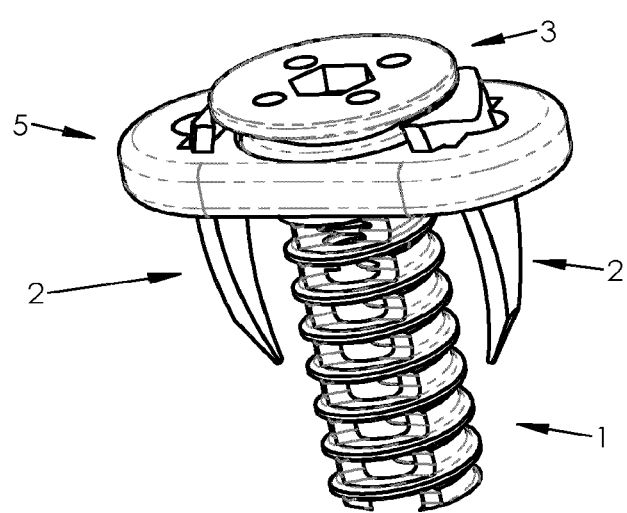
Figure 22A:
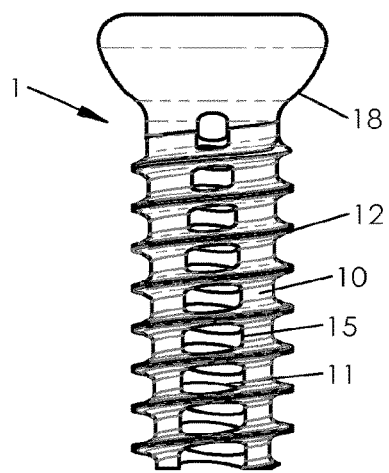
Figure 22B:
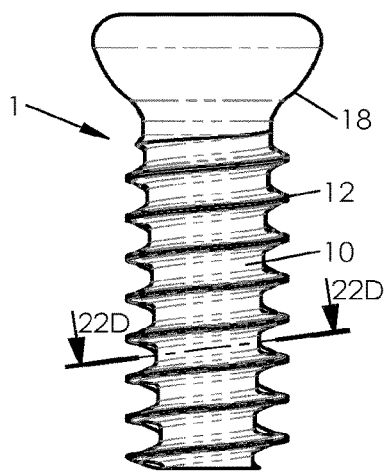
Figure 22C:
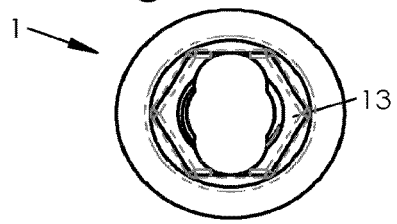
Figure 22D:
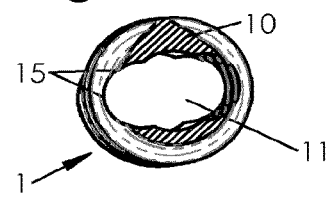
Figure 22E:
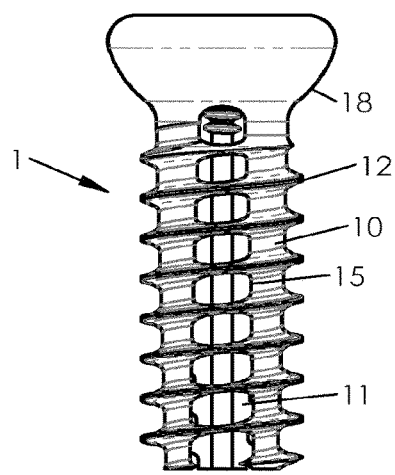
Figure 22F:
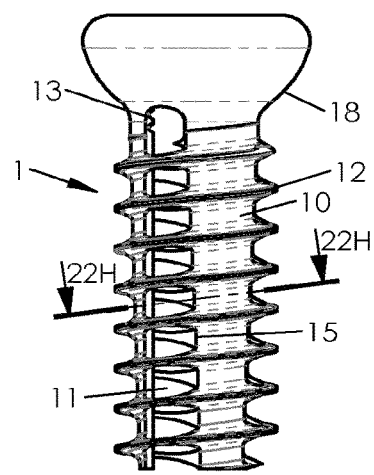
Figure 22G:
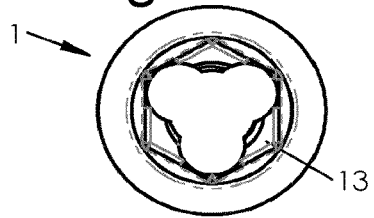
Figure 22H:
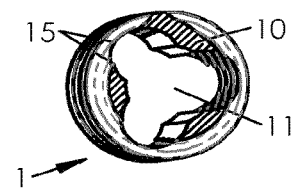
Figure 23A:
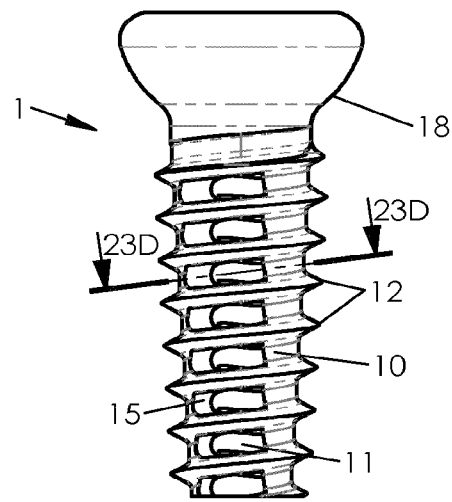
Figure 23B:
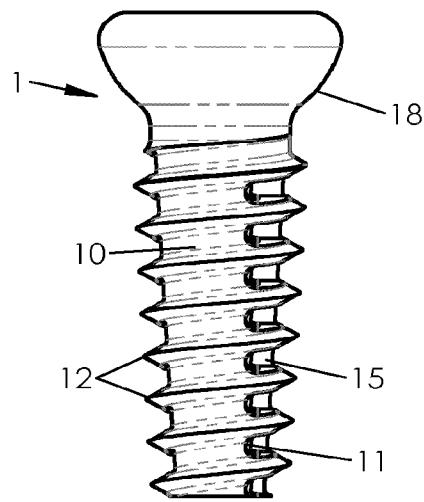
Figure 23C:
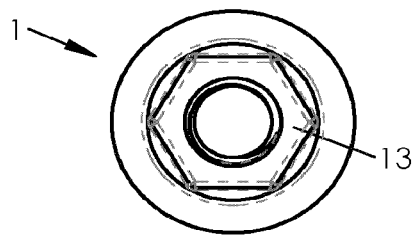
Figure 23D:
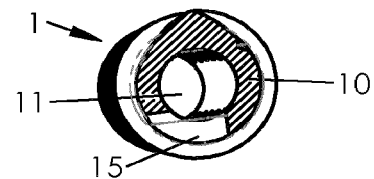
Figure 23E:
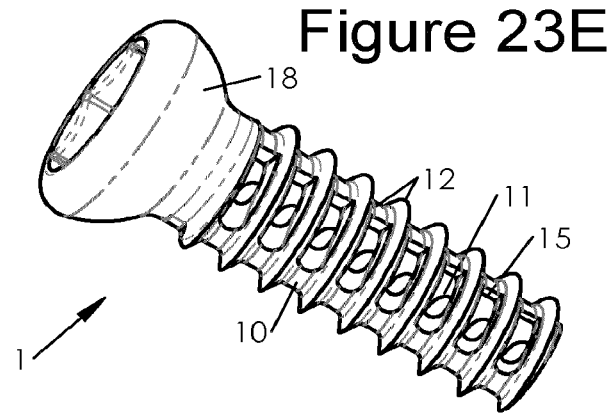
Figure 24A:
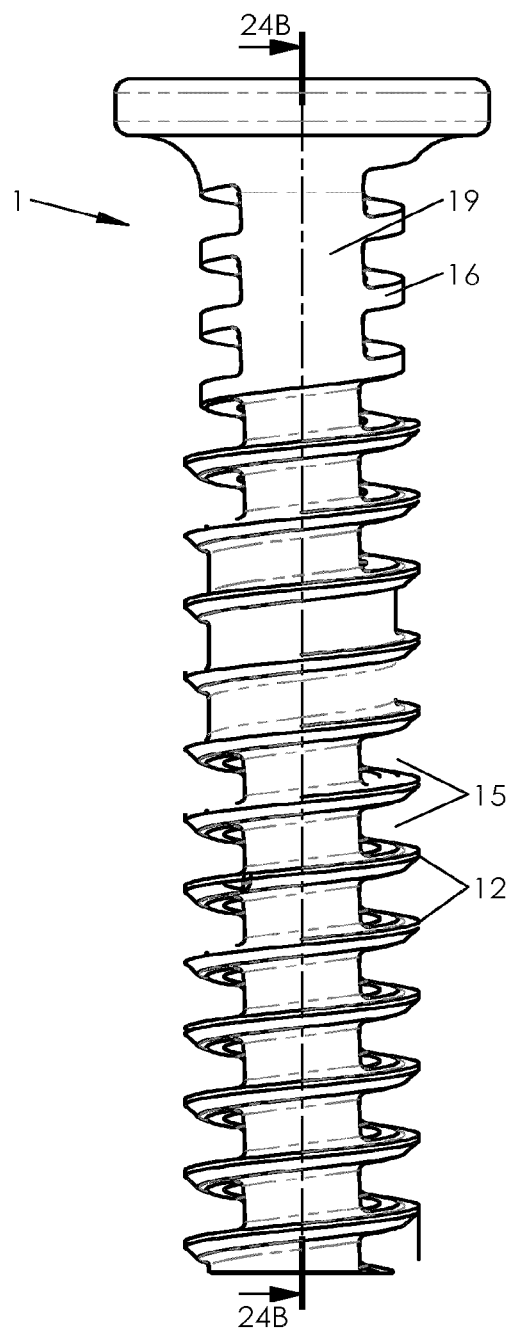
Figure 24B:
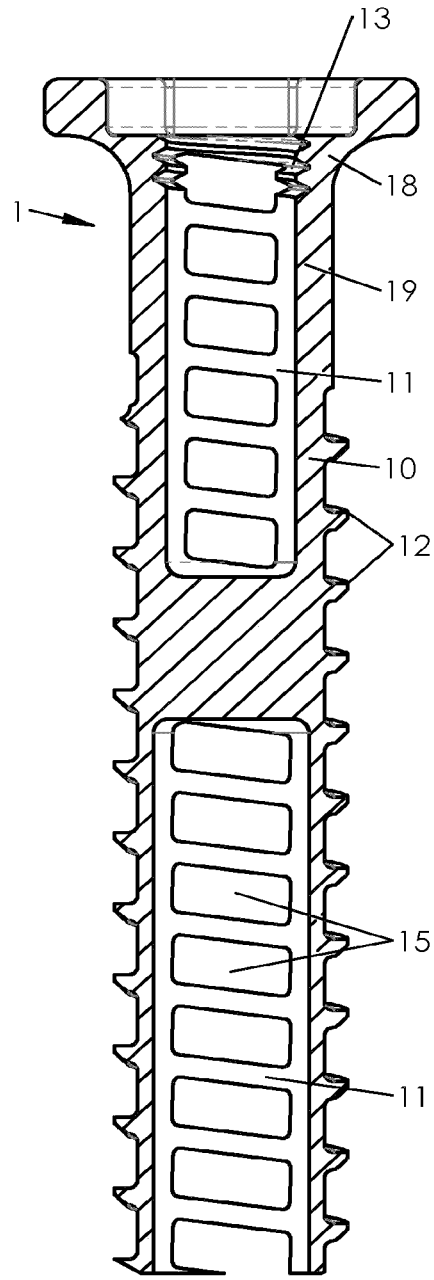
Figure 26A:
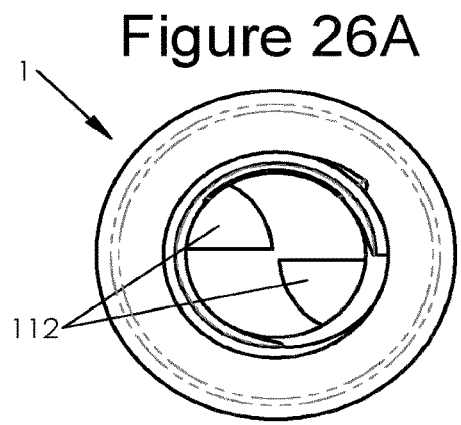
Figure 26B:
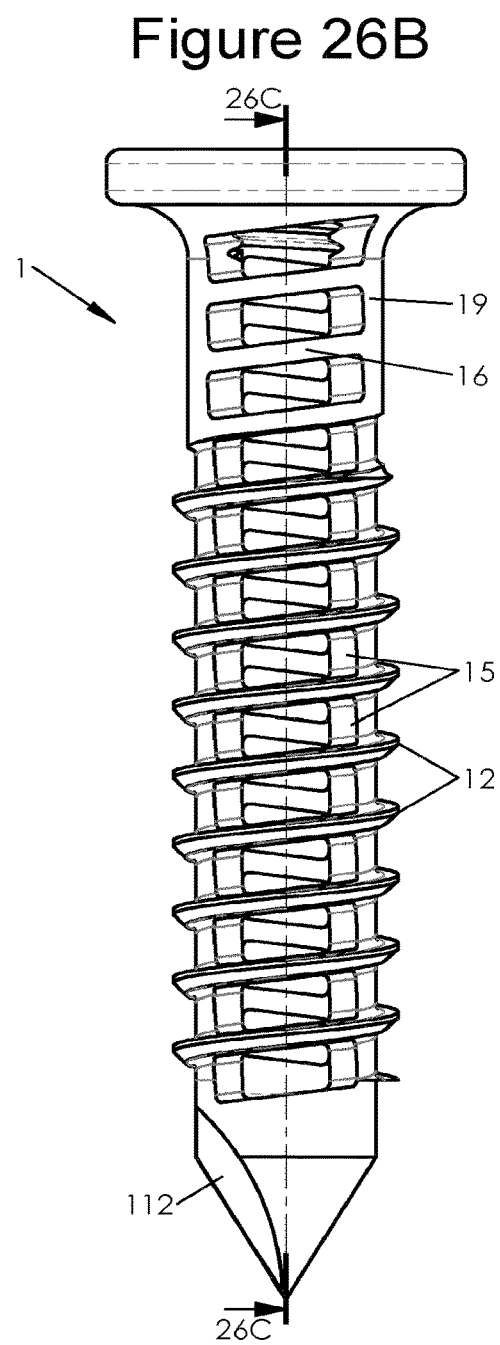
Figure 26C:
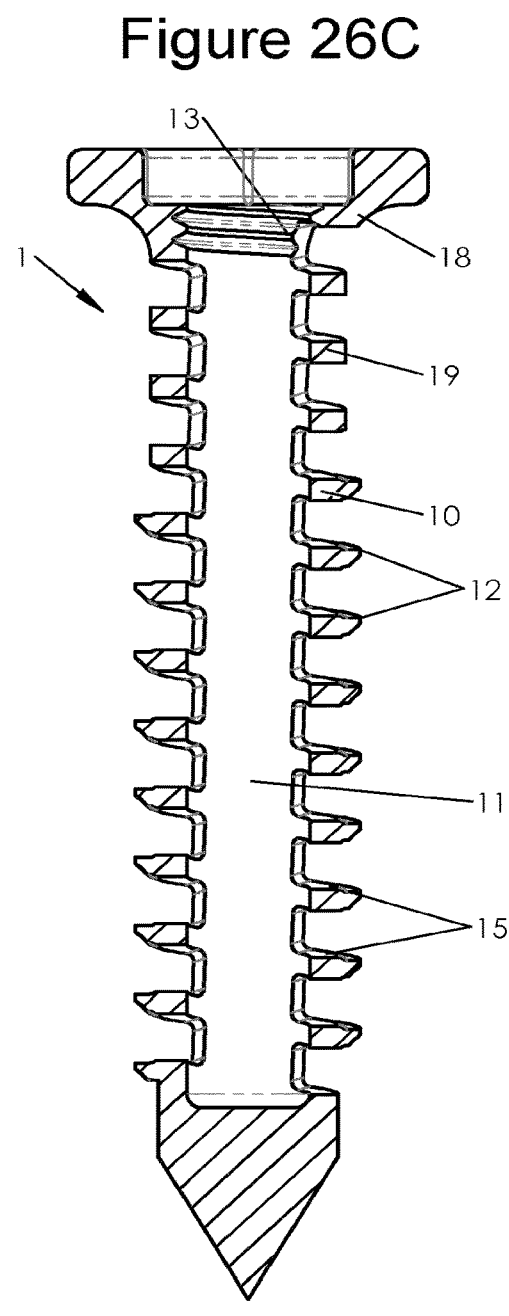
Figure 27A:
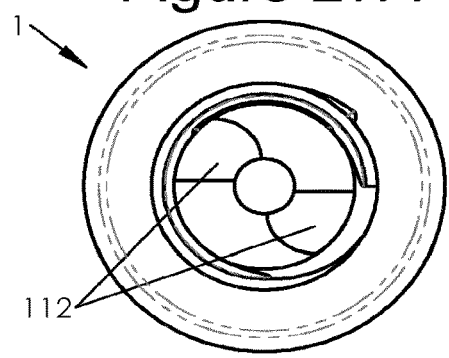
Figure 27B:
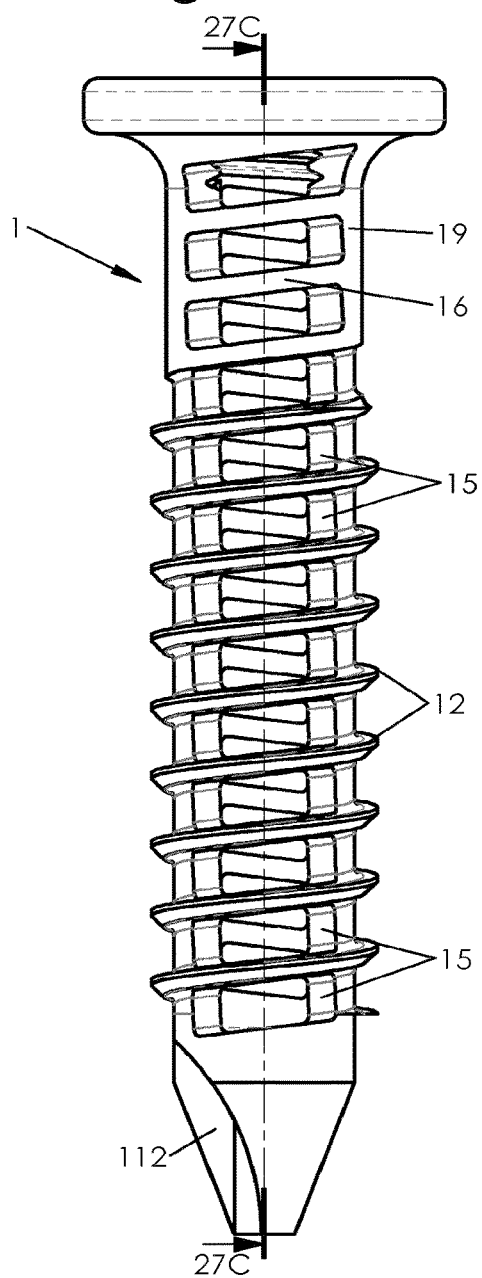
Figure 27C:
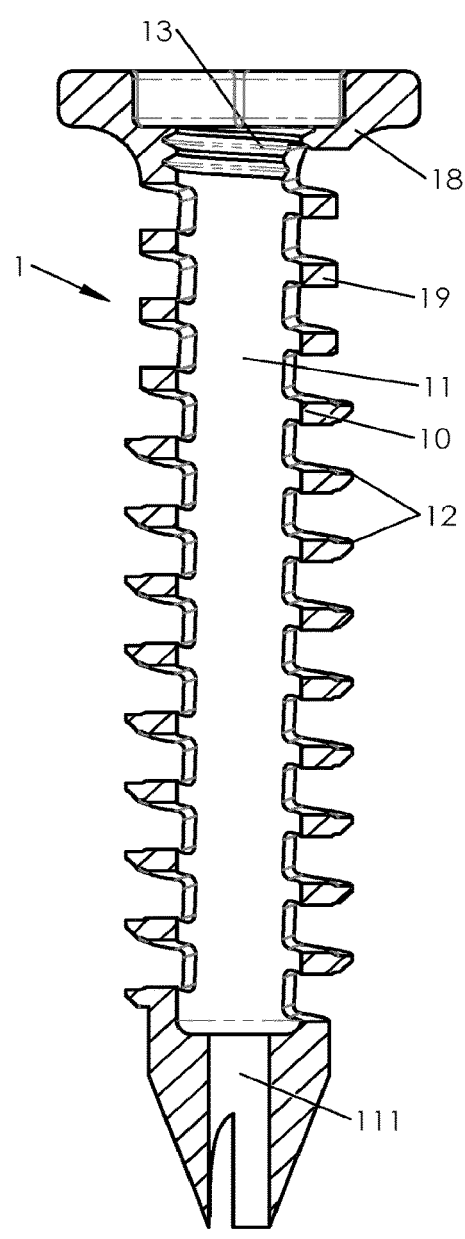
Figure 29A:
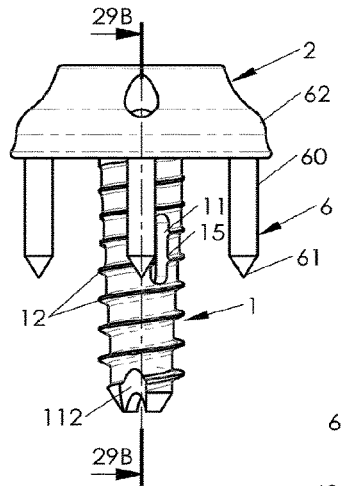
Figure 29B:
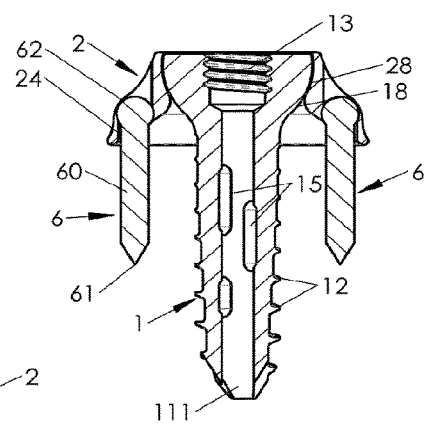
Figure 29E:
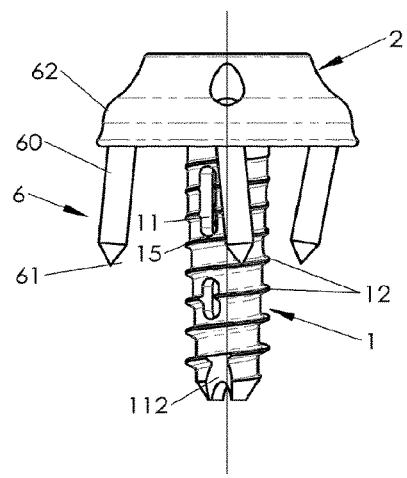
Figure 29C:
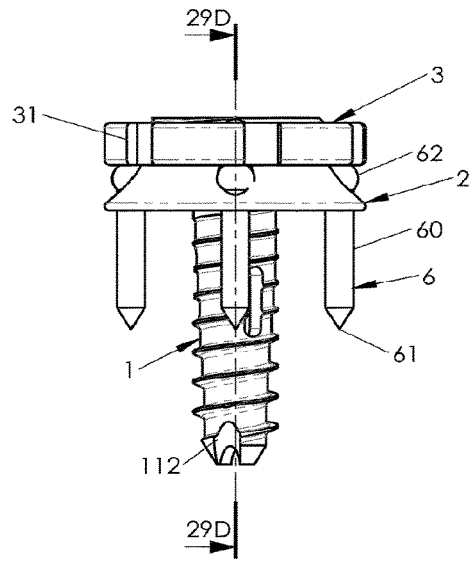
Figure 29D:
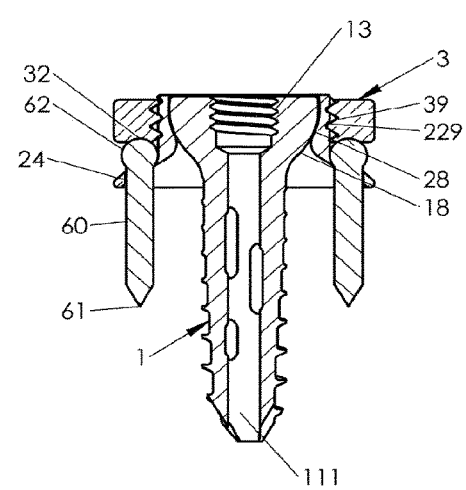
Figure 30A:
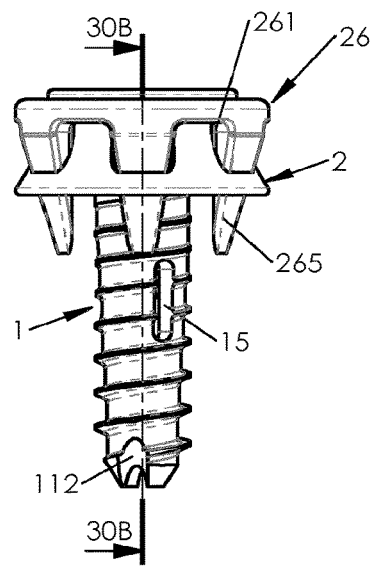
Figure 30B:
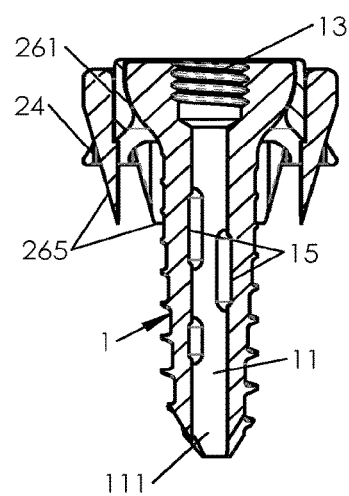
Figure 30C:
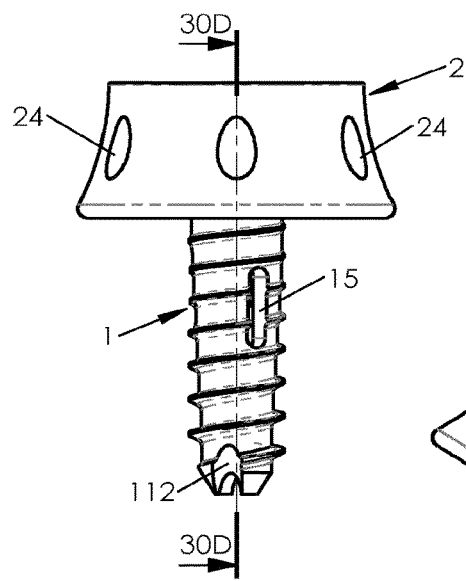
Figure 30E:
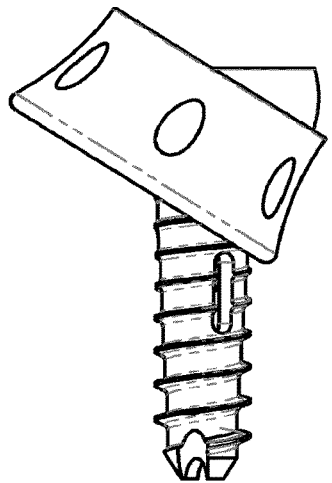
Figure 30D:
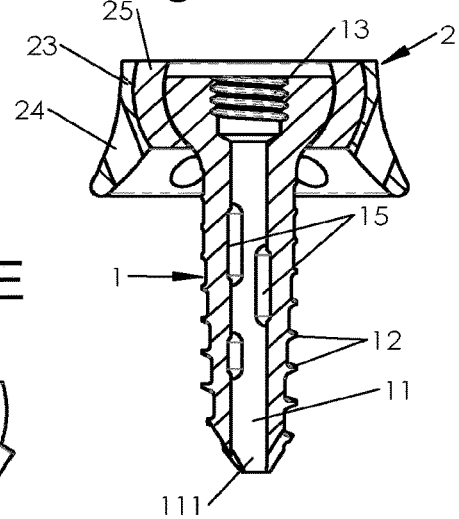
Figure 31A:
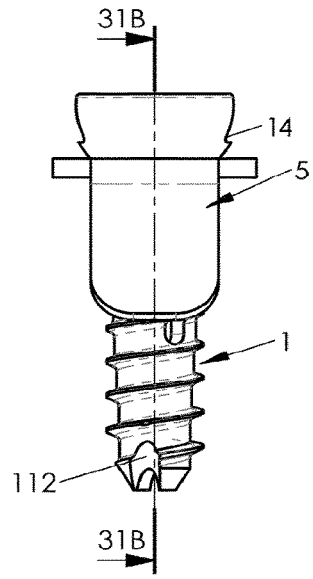
Figure 31B:
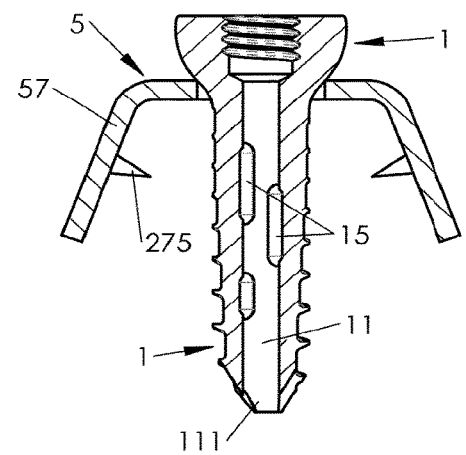
Figure 31C:
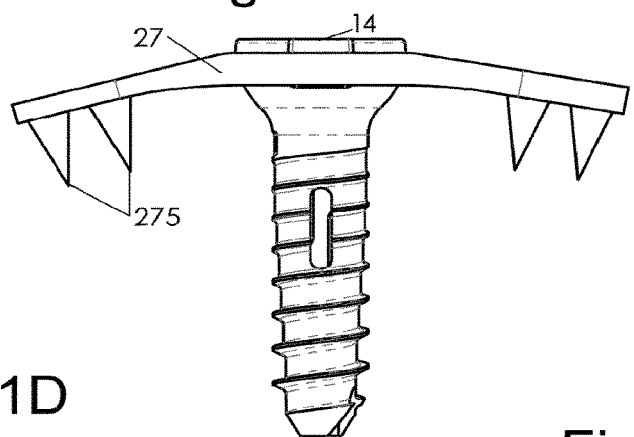
Figure 31D:
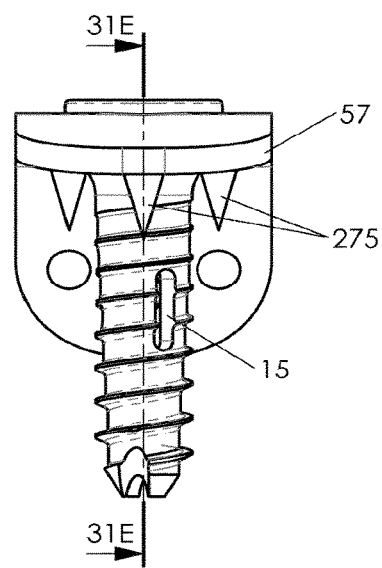
Figure 31E:
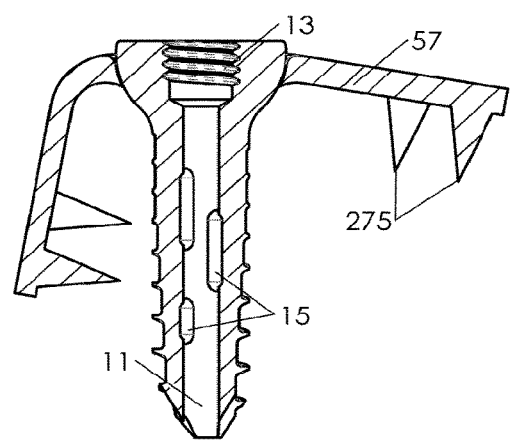
Figure 33A:
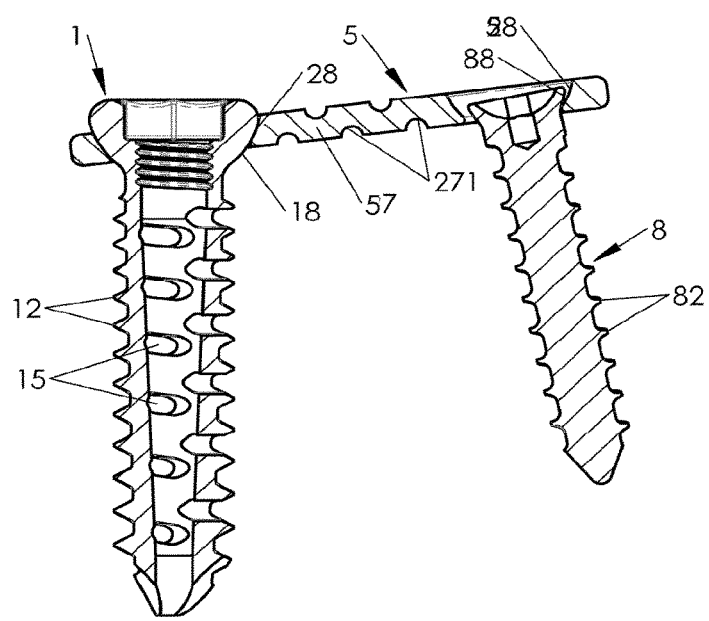
Figure 33B:
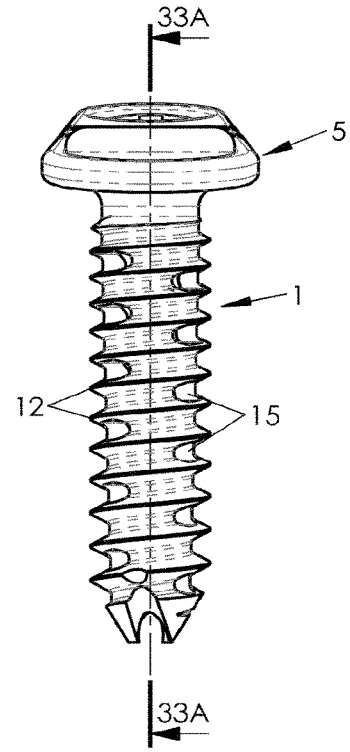
Figure 33C:
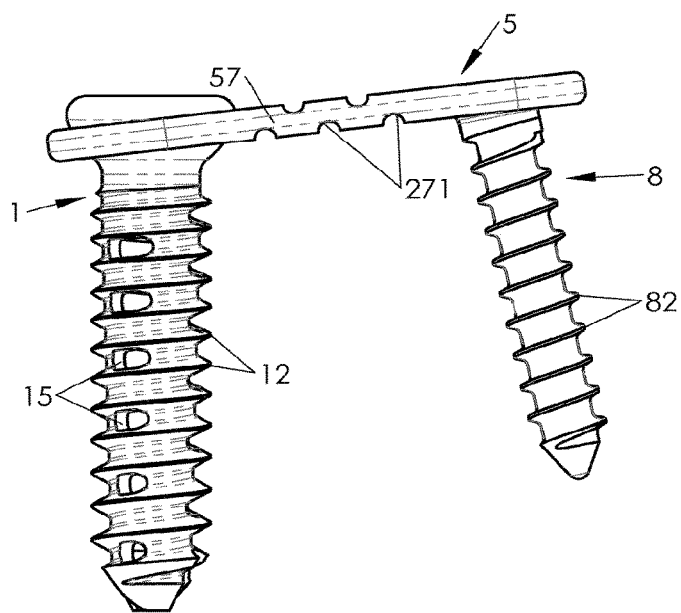
Figure 34A:
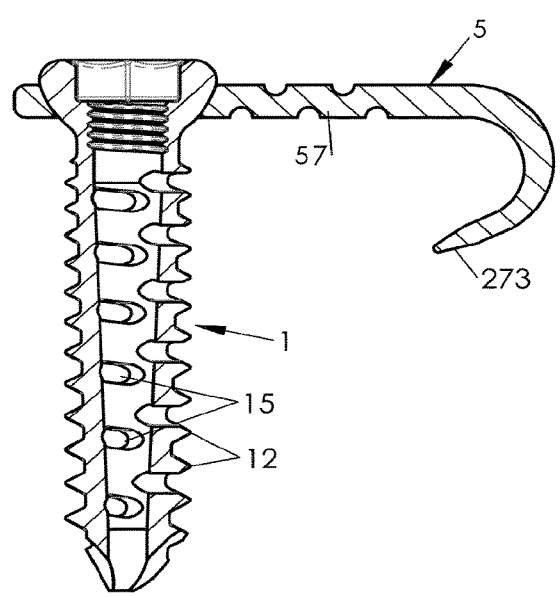
Figure 34B:
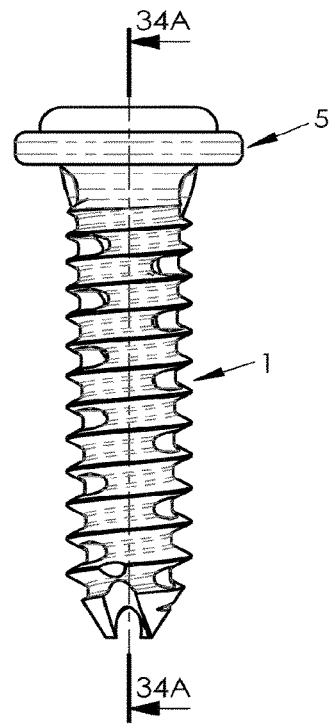
Figure 34C:
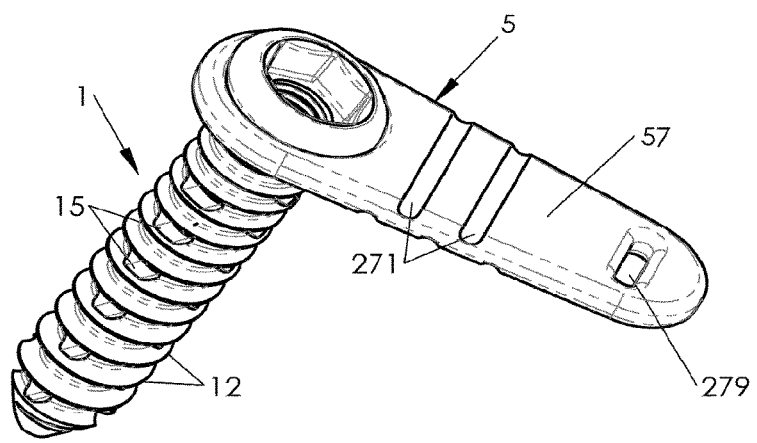
Figure 35A:
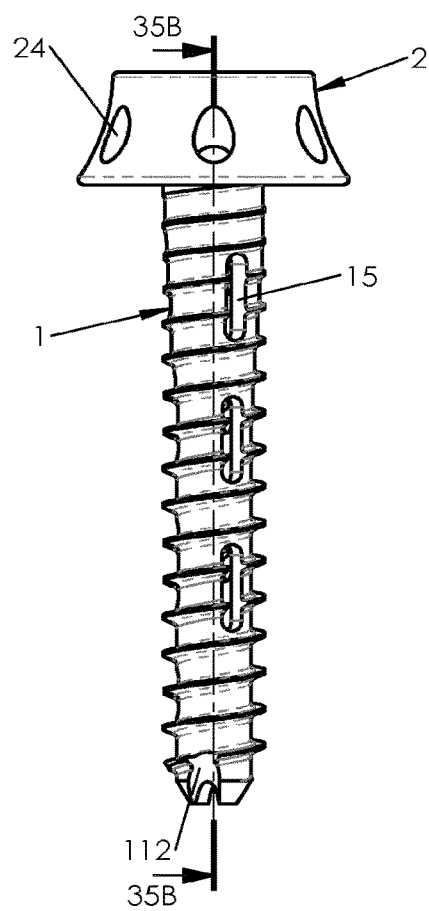
Figure 35B:
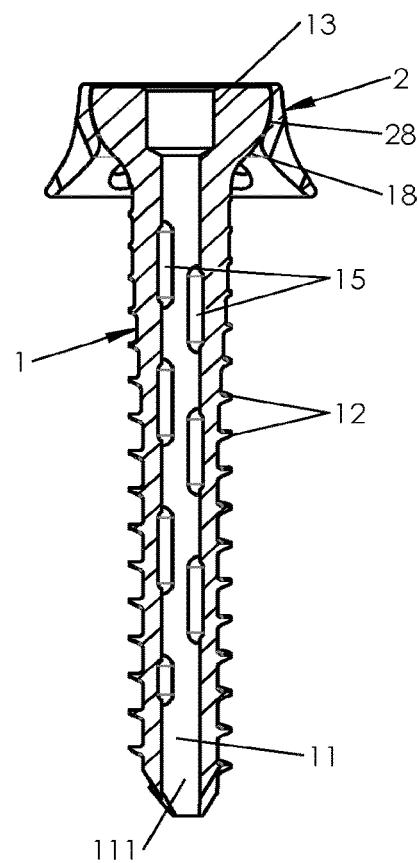
Figure 36A:
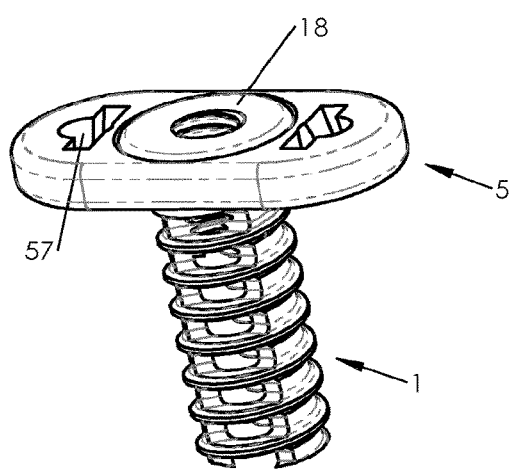
Figure 36B:
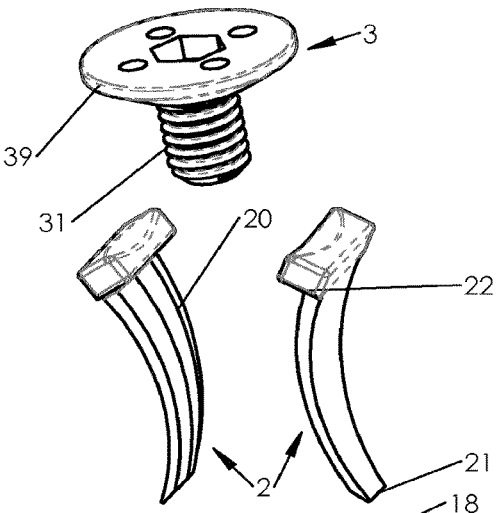
Figure 36C:
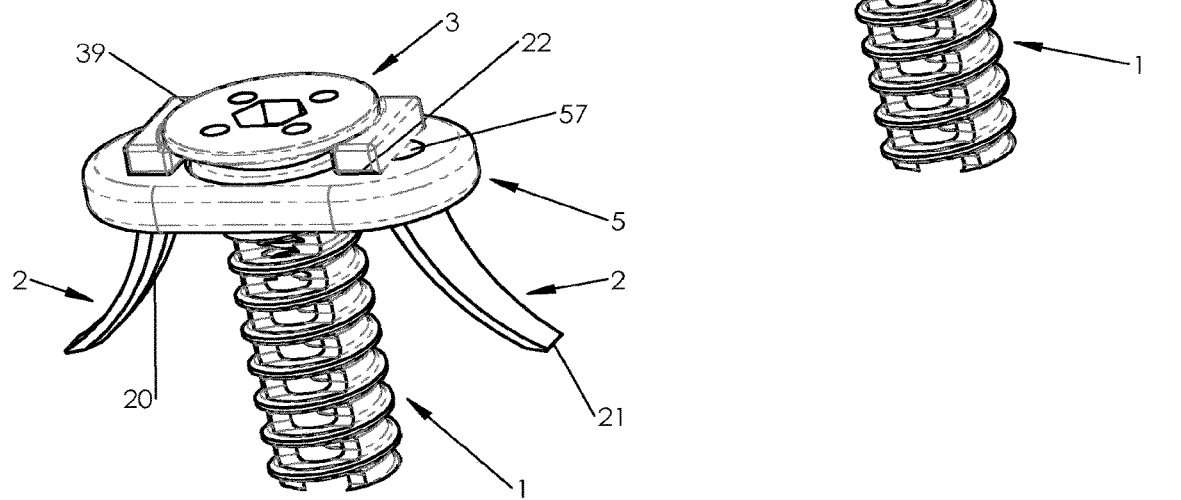

FIGS. 6A, 6B and 6C illustrate perspective, face and profile views respectively of an implant according to various embodiments, FIG. 6D illustrates a sectional view along the sectional plane 6D-6D of FIG. 6C, FIGS. 7A, 7B and 7C illustrate perspective views of a locking means, of a stabilization element and of an implant, respectively according to various embodiments, FIGS. 8A and 8B illustrate profile and sectional views respectively along the sectional plane 8B-8B of FIG. 8A, of an implant holder retaining an implant according to various embodiments and FIGS. 8C and 8D illustrate enlargements of the figures, FIGS. 8A and 8B respectively, FIGS. 9A and 9B illustrate perspective and profile views respectively of an implant according to various embodiments and FIG. 9C illustrate a sectional view along a sectional plane 9C-9C of FIG. 9B, FIG. 10A illustrates a perspective view of an implant-holder retaining an implant according to various embodiments and FIG. 10B illustrates an enlargement of this implant-holder at its portion retaining the implant, FIGS. 11A and 11B illustrate profile and sectional views respectively, along the sectional plane 11B-11B of FIG. 11A of an implant-holder retaining an implant according to various embodiments and FIG. 11C illustrates an enlargement of FIG. 11B, FIGS. 12A and 12B illustrate perspective and profile views respectively of an implant according to various embodiments and FIG. 12C illustrates a sectional view along the sectional plane 12C-12C of FIG. 12B, FIGS. 13A and 13B illustrate profile and sectional views, respectively, along the sectional plane 13B-13B of FIG. 13A, of an implant according to various embodiments, FIGS. 14A and 14B illustrate profile and sectional views, respectively, along the sectional plane 14B-14B of FIG. 14A of an implant according to various embodiments, FIGS. 15A and 15B illustrate profile and sectional views, respectively is along the sectional plane 15B-15B of FIG. 15A, of an implant according to various embodiments, FIGS. 16A and 16B illustrate profile and sectional views, respectively, along the sectional plane 16B-16B of FIG. 16A, of an implant according to various embodiments, FIG. 17A illustrate a perspective view of an implant-holder according to various embodiments and FIG. 17B illustrates an enlargement of this implant-holder at its portion indented to retain the implant, FIGS. 18A and 18B represent profile and sectional views, respectively, along the sectional plane 18B-18B of FIG. 18A, of an implant-holder retaining an implant according to various embodiments and FIG. 18C illustrates an enlargement of FIG. 18B, FIGS. 19A and 19B illustrate perspective views of stabilization means before and after assembling respectively, according to various embodiments and FIG. 19C illustrates a perspective view of an implant provided with such stabilization means, FIG. 20A, illustrates a perspective view of an implant and of a portion of stabilization means according to various embodiments and FIGS. 20B and 20C illustrate perspective views of an implant provided with stabilization means and locking means, before and after assembling respectively, according to various embodiments, FIGS. 21A and 21C illustrate perspective views of an implant and of stabilization and locking means, before and after assembling, respectively, according to various embodiments and FIG. 21B illustrates a perspective view of such stabilization means, FIGS. 22A, 22B and 22C illustrate front, profile and top views, respectively, of an implant according to various embodiments, FIG. 22D illustrates a sectional view along the sectional plane 22D-22D of FIG. 22B, FIGS. 22B, 22E, 22F and 22G illustrate front, profile and top views, respectively, of an implant according to various embodiments, FIG. 22H illustrates a sectional view along the sectional plane 22H-22H of FIG. 22F, FIGS. 23A, 23B, 23C and 23E illustrate front, profile, top and perspective views, respectively, of an implant according to various embodiments, FIG. 23D illustrates a sectional view along the sectional plane 23D-23D of FIG. 23A, FIGS. 24A and 24B illustrate profile and sectional views respectively along the sectional plane 24B-24B of FIG. 24A, of an implant according to various embodiments, FIGS. 25A and 25B illustrate profile and sectional views, respectively, along the sectional plane 25B-25B of FIG. 25A, of an implant according to various embodiments, FIGS. 26A, 26B and 26C illustrate top, profile and sectional views, respectively, along the sectional plane 26C-26C of FIG. 26B, of an implant according to various embodiments, FIGS. 27A, 27B and 27C illustrate top, profile and sectional views, respectively, along the sectional plane 27C-27C of FIG. 27B, of an implant according to various embodiments, FIGS. 28A and 28B illustrate profile and sectional views, respectively, along the sectional plane 28B-28B of FIG. 28A, of an implant according to various embodiments, FIGS. 29A and 29E illustrate profile views of an implant according to diverse embodiments, with a poly-axial locking in diverse positions, FIG. 29B represents a sectional view along the sectional plane 29B-29B of FIG. 29A, FIGS. 29C and 29D illustrate views, respectively profile and sectional views along the sectional plane 29D-29D of FIG. 29C of an implant according to diverse embodiments, FIGS. 30A and 30B illustrate views, respectively profile and sectional views along the sectional plane 30B-30B of FIG. 30A, of an implant according to diverse embodiments, FIGS. 30C and 30E illustrate profile views of an implant according to diverse embodiments, with poly-axial stabilization in diverse positions, FIG. 30D illustrates a sectional view along the sectional plane 30D-30D of FIG. 30C, FIGS. 31A, 31C and 31D illustrate profile views of an implant according to diverse embodiments, with diverse configurations of its stabilization means, FIGS. 31B and 31E illustrate sectional views, respectively along the sectional plane 31B-31B of FIG. 31A and along the sectional plane 31E-31E of FIG. 31D, FIGS. 32A and 32D illustrate views, respectively profile and front views, of an implant according to diverse embodiments, FIG. 32B illustrates a sectional view along the sectional plane 32B-32B of FIG. 32A and FIG. 32C illustrates an enlargement of the surrounded portion in FIG. 32B, FIGS. 33B and 33C represent views, respectively profile and front views, of an implant according to diverse embodiments, FIG. 33A illustrates a sectional view along the sectional plane 33A-33A of FIG. 33B, FIGS. 34B and 34C illustrate views, respectively profile and perspective views, of two implants according to diverse embodiments, FIG. 34A illustrates a sectional view along the sectional plane 34A-34A of FIG. 34B, FIG. 35A illustrates a profile view of an implant according to diverse embodiments and. FIG. 35B represents a sectional view along the sectional plane 35B-35B of FIG. 35A, FIGS. 36A, 36B and 36C illustrate perspective views of an implant according to diverse embodiments, respectively before, during and after assembling their locking means.

DESCRIPTION OF THE PREFERRED EMBODIMENTS OF THE INVENTION

The present invention relates to various embodiments of bone implants and of instruments for implanting such implants. As mentioned in the preamble of the present application, the invention may relate in particular to spinal implants, for example for arthrodesis of two vertebral structures. The present application more particularly details spinal implants, notably so-called "facet" implants, intended to be implanted between the articular facets of the vertebrae (so-called "intra-facet" implants) and/or implanted through these articular facets of the vertebrae (so-called "trans-facet" implants). Various embodiments of the present application are also adapted to an implantation in vertebral pedicles (so called "pedicular" implants) or at the level of the sacro-iliac joint or in various types of bone structures, either spinal or not, although the characteristics of the implants described in the present application make them particularly useful for their use in the rachis. Further, the implants of various embodiments are obtained by a manufacturing method with which it is possible to obtain particularly useful implants, for example for providing at least an answer to part of the problem discussed in the present applications. Thus, various embodiments may also relate to the method for manufacturing these implants.

Generally, the present invention preferably includes at least one bone implant (1), the technical characteristics of which are detailed hereafter in various embodiments. Generally, in the case of an implantation at articular facets, it is preferred to use two implants so as to secure the two (left and right) facets which joint two adjacent vertebrae, but this use is of course not limiting.

Generally, the bone implant (1) includes a body (10) elongated between a free end and a head (18) along a longitudinal axis on the one hand and, turns (12) of at least one threading, on at least one portion of said body (10) in proximity to the free end, along the longitudinal axis on the other hand. Further, the body (10) of the implant (1) preferably includes at least one longitudinal internal conduit (11) on at least one portion of a body (10) along the longitudinal axis and windows (15) in communication between said longitudinal internal conduit (11) and the outside of the body (10).

In certain embodiments, this longitudinal internal conduit (11) is obtained by at least one first central machining operation parallel to the longitudinal axis and at least one second machining operation in a so-called transverse plane, not parallel to the longitudinal axis and crossing the walls of the body (10) as far as the longitudinal internal conduit (11) by making windows (15) in communication between said longitudinal internal conduit (11) and the outside of the body (10), Thus, the implant includes an internal conduit (11) which preserves at least one portion of said turns (12) and the wall of the body behind the turns, and preserves non-machines portions thereof on the perimeter of said body (10). Indeed, the transverse machining makes windows on only certain portions of the perimeter (certain angular sectors, radially) and leaves non-machined portions between the windows. It will be noted that the transverse term is used here for referring to machining which preferably is only substantially transverse since it is achieved between the turns, it is not in a perpendicular plane to the longitudinal axis, but rather parallel to the turns of the threading, so that it makes windows along the same orientation as that of the turns. Nevertheless, in the case of a transverse machining over several turns, it is possible to use machining perpendicularly to the longitudinal axis. Radial, tangential or oblique machinings are therefore used according to the configurations but the present description groups them under the term of "transverse". Generally, regardless of how the internal conduit (11) is obtained, such non-machined portions on the perimeter of said body (10) are preserved so as to improve the solidity of the implant. It is understood that it is possible to preserve a variable number of non-machined portions depending on the number of transverse machining operations carried out. For example it is possible to provide two diametrically opposite portions or three gradually distributed portions around the longitudinal axis (either regularly distributed or not) or further a multitude of portions for example as visible in FIG. 1C, 22F or 2D. In other words, it is possible to provide a transverse machining every 90°, but a machining every 60° or every 180° may be preferred for leaving greater non-machined portions and thereby preserve the solidity of the implant.

The terms of "head" and "free end" are used in the present invention with reference to the fact that the implant generally appears in the form of a screw, with a generally cylindrical or conical or frusto-conical body (10), but these turns and these shapes of the implant should not be considered as limiting. Diverse portions of the implant are on the other hand designated in the present application by the terms of "proximal" meaning "in proximity to the head", or "distal" meaning "in proximity to the free end" or further "median" meaning "substantially in the middle between the two ends", but it is clear that these terms are not either limiting and that the person skilled in the art will appreciate that the position of these portions may vary along the longitudinal axis. Further, the term of "appreciably" or "substantially" is used with reference to various features in order to indicate that they may be exactly as defined or be approximately as defined. For example, the expression "a substantially planar shape" should be understood as designating a shape approximately planar since the person skilled in the art will be able to vary the exact shape insofar that it would keep a globally planar shape meeting the relevant technical requirements. Also, the present description may define features without this specifying of approximation with the terms of "appreciably" or "substantially" but it will be clear for the person skilled in the art that this notion applies even in the absence of such terms.

Further the term of "machining" is here used in a non-limiting way for referring to the manufacturing of the implants and it is clear that this term in facts covers any type of manufacturing techniques, such as for example, bores, drillings or milling operations, but also electro-erosion or any type of technique giving the possibility of making surfaces or accommodations on or in the implants. Further the term of "transverse" is used for indicating that the second machining operation is in a plane not parallel to the longitudinal axis and tends to indicate that it is perpendicular to the longitudinal axis, but the person skilled in the art will notably understand because of the oblique orientations of the turns of the threading, that this plane (which is therefore substantially transverse) is not necessarily perpendicular to the longitudinal axis and will generally be rather Obliquely oriented, preferably parallel to the turns.

In certain embodiments, said body (10) is substantially cylindrical, as for example visible in most of the figures, notably FIGS. 1C, 2D, 9C, etc. In other embodiments, said body (10) is substantially conical or frusto-conical, as illustrated for example in FIG. 22A, 22B, 22E, 22F or 23A, 23B and 23E. This shape facilitates implantation of the body since the free (distal) is thinner than the proximal end. In some of these embodiments with a conical or frusto-conical body, the perimeter of said threading is substantially cylindrical in spite of the conical or frusto-conical shape of the body (10), as for example illustrated in FIGS. 22A, 22B, 22E and 22F. This type of threading with a cylindrical perimeter on a frusto-conical body improves the stability of the implant since the turns of the distal end will penetrate more deeply into the bone tissue.

Regardless of how the windows are obtained (longitudinal or transverse machining operations), aligning them or shifting them relatively to each other may be preferred. Thus, in certain embodiment, said windows (15) are shifted relatively to each other along (or rather around) the longitudinal axis, for example as illustrated in FIG. 2D, while in other embodiments, said windows (15) are aligned with each other along the longitudinal axis, for example as illustrated in FIG. 1C. It will be noted that it is also possible to provide a combination of these arrangements, by providing aligned windows on one portion and shifted windows on another portion. When they are shifted relatively to each other, it is generally preferred that a more proximal window be shifted relatively to a more distal window on the side which corresponds to the direction of the screwing. Thus, for example with a threading oriented clockwise a proximal window will be shifted left relatively to a more distal window, so as to improve sharpening of the bone or cartilage which may be gradually obtained with successive windows during screwing.

In the embodiments comprising a longitudinal internal conduit (11) an windows (15) obtained by at least one first machining operation and at least one second machining operation respectively. In these embodiments, the second machining, giving the possibility of obtaining the windows (15), preferably preserves the material of the body (10) behind the turns (12), as for example illustrated in FIGS. 1C, 1D, 2D, 7C and more particularly visible in FIG. 12C, 26C or 27C. Thus, in particular in the embodiments wherein the windows are obtained by a second machining which is achieved along an orientation substantially transverse to the longitudinal axis, these windows preserve the material behind the turns (since the first longitudinal machining has a diameter smaller than that of the body at the turns). Thus, the person skilled in the art understands that the implant which results from this, is found to be improved by the fact that it has turns which penetrate more deeply into the tissue, as if they were larger, since the material around the turns has been removed by the machine operation (thus reducing the residual width of the body) and that the pressure present in the surrounding tissues, in particular in the case of an implantation at an articular level, will ensure that the turn will sink into the bone more deeply. Further, the solidity of the implant is improved by means of the material preserved by the machining, while in the prior art, notably when the windows are made by a machining achieved uniquely along the longitudinal axis of the implant, only the thread is preserved and the turns (12) are therefore alone in order to support the significant forces during and after the screwing. Thus, a stable and solid implant is obtained. Further, by making the windows by a second non-longitudinal machining, it is possible to obtain (or optimize) an effect of sharpening of the bone structures around the implant, during the screwing, generally accompanied by a filling effect of the implant through these sharpened bone structures during the screwing. Indeed, by making windows (15) aligned with each other over several successive turns (aligned along the longitudinal axis) and/or extending over several successive turns, a local reduction in the size of the perimeter of the implant is obtained (i.e., a local reduction in the diameter, if the implant is cylindrical or conical), like for example as visible by comparing FIGS. 6C and 6D, 9B and 9C, 12B and 12C, 13A and 13B, 14A and 14B or 24A and 24B, 25A and 25B, 26B and 26C, 27B and 27C, 28A and 28B, but also as it may be inferred from a configuration such as that of FIG. 35A, as detailed hereafter. Thus, during the screwing, the pressure of the surrounding bone structures leads to sinking of the turns into the bone tissue and the rotation of the implant causes sharpening of the bone against the edges of the windows (15), and often a "self-filling" of the implant by the thereby sharpened/cured tissues, In some of these embodiments, the second machining operation may for example be carried out tangentially to the perimeter of the body (10) resulting in windows (15) which are flared from the inside to the outside of the body (10), as (further) illustrated for example in FIGS. 1A, 2A, 3B, 2C, 6C, 6D, etc. However, alternatively, the second machining operation may be carried out substantially radially (or along an oblique axis between the radial orientation and the tangential orientation) so as to obtain windows having at least one sharpened outer edge as detailed hereafter. Thus, certain embodiments relate to a bone implant (1) including an elongated body (10) between a free end and a head (18) on the one hand along a longitudinal axis and turns (12) of at least one threading, over at least one portion of said body (10) in proximity to the free end on the other hand, along the longitudinal axis. This implant is characterized in that the body (10) includes a longitudinal internal conduit (11), over at least one portion along the longitudinal axis, obtained by at least one first machining (preferably central, but in all the embodiments, this longitudinal machining is not necessarily central) parallel to the longitudinal axis and at least one second machining in a plane, a so called transverse plane, not parallel to the longitudinal axis, and crossing the walls of the body (10) as far as the longitudinal internal conduit (11) by making windows (15) communicating between said longitudinal internal conduit (11) and the outside of the body (10). Advantageously, this implant has windows (15) aligned with each other along the longitudinal axis and made between several successive turns and/or extending over several turns, so that the size of the implant transversely to the longitudinal axis (optionally excluding the turns, i.e., by only taking into account the turns) is locally reduced, which promotes sharpening of the tissues into which the implant is screwed and optionally the automatic filling of the internal conduit (11) of the implant with these tissues.

In certain embodiments, non-exclusive but however eventually independent of those with two non-parallel machining operations as defined above, said windows (15) of the bone implant (1) advantageously have at least one sharpened outer edge. Indeed, regardless of how the conduit and the windows are obtained, it may be useful to provide at least one sharpened outer edge for the windows (15). In particular, it is generally preferred that the sharpened edge be the one which first attacks the bone during the screwing of the implant, so that this sharpened edge may gradually dig into the bone (for example by cutting out shavings) during the screwing. Thus, when the windows (15) are obtained by a second machining operation, the latter may for example be achieved along radial or oblique axis as explained above, so as to obtain one sharpened leading edge, as illustrated for example in FIGS. 23A and 23D (the right outer edge on the window of FIG. 23D has a cutting edge which allows cutting out of the bones or of the cartilage). Also, if the windows are obtained, as in the prior art, by longitudinal machining operations, it is possible to provide the latter so as to make such a cutting edge, as illustrated for example in FIGS. 22C, 22D, 22E and 22F, which show illustrative and non-limiting examples of such machining operations (and moreover shows the fact that a variable number of machining operations may be provided for making the windows). This type of layout with at least one edge (preferably the leading edge) gives a possibility of at least sharpening or scraping out the bone during the screwing, which stimulates bone growth and stabilizes the implant, this also gives the possibility, optionally, of automatically filling (at least partly) the longitudinal internal conduit (11) during the screwing, which gives the possibility of limiting the resorting to exogenous bone tissue or to a substitute or to a cement, even if the latter may be used (additionally or alternatively) in various embodiments. Indeed, diverse embodiments provide the use of exogenous bone tissue and/or of bone substitute and/or of cement in the implants, injected before or after (i.e., in situ) the setting into place of the implant, in order to facilitate bone growth.

On the other hand, in certain, non-exclusive embodiments but however independent of those having two machining operations and/or with a sharpened edge as defined above, said head (18) of the implant (1) is provided with stabilization means (2, 3, 5) (e.g. compression, locking, supporting means) of the implant, intended to bear upon the bone tissue around said head (18) (these stabilization means optionally comprising locking means for securing them on the implant). Various embodiments are described hereafter for the stabilization means but the person skilled in the art will understand from this functional definition that the implant is provided so that its head (which is generally the subsisting portion outside the bone tissue or the articular space) is stabilized on the bone tissue (on a bone surface or on the edges of the joints).

The various embodiments described in the present application generally relate to a bone implant (I) which is in particular useful for implantation at articular facets of two adjacent vertebrae, i.e., between two facets (intra-facet implant) or through both facets (trans-facet implants). The threading (12.) is therefore particularly adapted to screwing in bone or articular tissue.

In certain embodiments, the implant includes means for stabilization by bone attachment in proximity or at a distance from the first body (10) of the implant.

In certain of these embodiments, this stabilization by bone attachment is achieved in proximity to the first body (10), like for example the rods (21) or bells (2), rings, crowns, etc. detailed in the present application with reference to FIGS. 1 to 8 and 9 to 12. Other advantageous embodiments for stabilization by bone attachment in proximity to the implant are illustrated in FIGS. 29, 30, 32, 35 and 36. In certain embodiments, poly-axial locking means are provided, i.e., allowing locking of the stabilization means (generally also poly-axial) in diverse orientations. FIGS. 29 and 30 show examples of such poly-axial locking means (3, 26, 6). In 29A, 29B, 29C and 29D, the stabilization means again include a ring, a crown or a bell (2) the perimeter of which may be supported on the surrounding tissues for stabilizing the implant. This bell (2) is provided with holes (24) able to receive nails or anchors (6) having an elongated body (60) and provided with a spike (61) allowing anchoring in the bone tissue around the implant. Preferably, these nails or anchors are provided with a poly-axial head, for example by means of a shape as a sphere portion, able to cooperate with the mating shape of the holes (24) in the stabilization bell (2). Thus, it is possible to plant nails (6) along diverse orientations, once the bell (2) is positioned on the surrounding tissue. According to the shape of the holes (24) of the bell (2), it is possible to provide that the nails (6) are blocked all alone by pressing against an abutment. Nevertheless, it is generally preferred to provide an additional locking means (3), as for example illustrated in FIGS. 29C and 29D. In this example, the bell (2) is provided with an outer threading (229) on which is screwed a locking means (3) such as a tapped ring (39), able to immobilize the nails (6) or anchors in their housings (24) of the bell (2). A poly-axial stabilization element (2) is thereby obtained with additional stabilization by bone attachment, also poly-axial, and lockable in a poly-axial way also. The same type of advantage is shown in the example of FIGS. 30A, 30B, 30C, 30D and 30E. In these examples, the stabilization bell (2) is also provided with holes (24) for receiving bone attachment means (26), but the latter are formed with a crown (261) provided with teeth (265) able to be inserted through holes (24) of the bell (2) and to be planted in the bone around the implant. This crown (261) preferably has an inner diameter greater than the outer diameter of the bell (2), so that poly-axiality is preserved even after the locking. FIG. 32A shows another example of a stabilization means (2) comprising a preferably cartilaginous anchoring rather than bone anchoring. In this example, the ring (2) slipped onto the head of the implant includes at least one blade (276), preferably two blades, extending longitudinally and able to be anchored in the tissues around the implant. This type of embodiment is preferably intended for interfacet implantation, i.e., with the implant positioned between two cartilages, but the blades are also rather intended to be inserted between both of these cartilages. Such blades may include notches (277) opposing the withdrawal of the blades from the tissue in which they are planted or against which they rest. Thus, these blades will preferably be housed between two cartilages and their notches will stabilize them therein. In FIG. 32A, these blades are illustrated as running along the body of the implant at a small distance from the latter, but of course it is possible to provide diverse spacings, notably when these stabilization means are provided for being poly-axial as detailed in the present application and as illustrated in this FIG. 32A. It will be noted that such a cartilage stabilization may of course be achieved by means of other structures than simple blades and that it is possible to use more extended elements. On the other hand, in diverse embodiments, it is possible to provide locking means (3) by bone anchoring through the implant, as for example illustrated in FIGS. 32B, 32C and 32D. In these examples, the locking means (3) include coupling means (31) with the implant (for example coupling by screwing) but above all include at least one spike (390), preferably curved, mounted on a joint (395) of the locking means, so that during the introduction of the locking means (3) into the implant, the spike (390) pivots around its joint (395) and crosses a passage (159) made in the wall of the body (10) of the implant in order to penetrate the tissue around the implant. A kind of anchor substantially transverse to the longitudinal axis of the implant is thereby obtained and gives the possibility of locking the latter. It will be noted that in the case of coupling by screwing of the locking means (3) in the body (10) of the implant, the joint (395) of the spike or of the spikes (390) will preferably be decoupled from the rotation of the locking means, so that this joint is only move in translation inside the implant and that the spike (390) may penetrate the surrounding tissues without any hindrance.

In certain embodiments, double poly-axiality of the stabilization means is provided, which gives the possibility of increasing the possible tilt angle, but which also gives the possibility of either resorting or not to diverse stabilization elements combined with each other. An example is illustrated in FIG. 30D. For example, a first ring or crown (25), the inner wall of which at least its one portion of the sphere portion shape of the screw head gives the possibility of providing poly-axiality. This first ring may then be used alone as a stabilization means capable of being supported on the surrounding bone tissue. Further, by means of an outer wall with the shape of a sphere portion, this first ring (25) may receive a second ring or crown (23), the inner surface of which fits the shape of the first ring (25), thereby forming a wide stabilization means (2) than the first ring alone, allowing more extended support on the surrounding tissues, but also allowing a greater tilt if necessary, by means of the double poly-axiality. The second ring (23) illustrated in the examples of FIGS. 30C, 30D and 30E include apertures (24) for receiving bone attachment means (26) of the type of those of FIGS. 30A and 30B, but one skilled in the art will of course understand that any other type of locking means or bone attachment means may be used, notably from among those (3, 6, 26, etc.) detailed in the present application. In certain of these embodiments, this stabilization by bone attachment is achieved at a distance from the first body (10). In certain of these embodiments, as for example illustrated in the illustrative and non-limiting FIGS. 33A, 33B and 33C, particularly useful in the case of an implantation of the body (10) in the interfacet space, the implant includes a second body (8), also of an elongated shape along a longitudinal axis and substantially parallel to the first body (10). This second body (generally cylindrical or conical or frustoconical like the first body) is preferably provided with a threading (82) adapted for being screwed into the bone tissue. Screwing in the cartilage is thereby obtained by the first body and screwing in one of the facets (and no longer at the joint) or in one of the pedicles, the blades or at the base of the spinous process by means of the second body (8). It will be noted that it is possible, like in the illustrated example, to provide that the second body (8) be also poly-axial, i.e., with a head for which the perimeter (88) as a sphere portion cooperates with a mating housing (58) in the plate (5), in order to allow attachment according to diverse orientations of the second body (8). In certain embodiments, the second body may in fact be elongated but not include any threading, such as for example a sharpened nail or plate, nor even be rectilinear, like for example curved anchors (2), preferably sharp (21), for example of the type of those illustrated in FIGS. 19A, 19B, 19C, 20B, 20C or 36B and 36C. It will be noted that in FIGS. 36B and 36C, a use of curved anchors is provided with an orientation such that the curved anchoring moves away from the first body (10) in order to provide stabilization and more extended attachment and limiting the risks of failures of the bone structures around the first body (10). On the other hand, in certain cases, an attachment closer to the first body (10) is preferred and curved anchors are then used in the direction of the latter, like for example in FIGS. 19A, 19B, 19C, 20B and 20C. It will also be noted that it is possible to provide that the attachment at a distance by an anchor (either curved or straight) or a nail (curved or not) is achieved via a poly-axial insert positioned in the thickness of the plate (5) and able to receive this anchor or this nail, which gives the possibility of giving diverse orientations to the latter. This type of solutions with a second body allows good stabilization of the implant. Other embodiments of stabilization means by attachment at a distance may be contemplated, such as for example a hook or a plate forming a hook, as for example illustrated in FIG. 34A showing a stabilization plate (5) ending with a hook (273) capable of being planted in a neighboring bone structure or being hooked up with a neighboring protruding bone structure. The second body (8) is generally positioned at a distance from the first body which is provided for avoiding cracking or fracturing of the bone tissue by the screwing or the implantation of both bodies. The second body is thus maintained at a distance from the first body, preferably by stabilization means such as those described in the present application, like for example stabilization plates (5) giving the possibility of being supported on the surrounding bone tissue and possibly an attachment in proximity to the first body (10) or at a distance from this first body (10). Diverse illustrative and non-limiting examples of such plates are shown in FIGS. 19A, 19B, 19C, 20A, 20B, 20C, 31A, 31B, 31C, 31D, 31E, 33A, 33B, 33C or further 34A, 34B and 34C. In particular, in diverse embodiments, the present application describes stabilization means comprising rods or a bell or further plates and one skilled in the art will note that these stabilization means are mounted on the implant with portions which generally have a thickness provided for affording good solidity, unlike certain implants of the prior art provided with thin plates which risk being untimely twisted or broken, as illustrated for example in FIGS. 19.A, 19B, 19C, 20A, 20B and 20C showing thick plates. On the other hand, in certain embodiments, it is possible to benefit from thin plates capable of being twisted and thus fitting the anatomy of the implantation site. Thus, as for example illustrated in FIGS. 31A, 31B 31C, 31D, 31E, 33A, 33B 33C or further 34A, 34B and 34C, provision may be made for deformable plates, or with shape memory, in. a plastic way in order to conform them in situ with the surrounding anatomy of the implantation site. As suggested by these figures, such plasticity may be of course obtained by the material or by the thickness (57) of the plate (5), but also be obtained by local thinning, such as for example grooves (271) made in the plate (5) for facilitating its shaping by the surgeon during the implantation. In the illustrative and non-limiting example of FIG. 34C, one benefits both from a deformable plate (5) and a non-threaded bone anchoring means, like for example an anchor or a nail to be planted through an orifice (279) made in the plate (5).

In the examples of FIG. 31, the stabilization means (5) formed by a plate (57) provided with spikes or teeth (275) adapted for being anchored in the surrounding bone (or cartilage) tissue, once the definitive shape is given to the plate (57). It will be noted that in these examples, the screw head (further provided once more with notches (14) for receiving an implantation tool) is polyaxial, by means of a sphere portion with which cooperates a hole in the plate (57) which may therefore assume diverse orientations relatively to the implant. Further, the implant may provide, as illustrated in FIG. 31E, hooking-up means (13) capable of receiving attachment means (not shown) giving the possibility of locking the position of the diverse elements of the implant. Also, the head or the portion of the implant which is intended to remain outside the bone tissue is generally provided so as to have a restrictive height, so as to avoid a too large protrusion (or projection) which has the risk of damaging surrounding tissues or of loosening the implant by the contact with other structures. Thus, both of these types of layout are sometimes combined in certain embodiments so that a head with a small height is provided with stabilization means, notably those provided with a second body maintained at a distance from the first body (10), the thickness of which represents at least one third of the height of the protruding portion of the implants at the surface of the bone tissue. This type of combination gives the possibility of providing a particularly stable implant since it has a head which is little subject to aggressions (outer aggressions) and solidly retained by stabilization means which further protect this head from such aggressions. On the other hand it will be noted that in the case of a second body maintained at a distance from the first body (1), a body provided with a head of restricted dimensions, for example with a height not exceeding the thickness of the portion connecting both bodies together will be preferably selected but it is generally preferred that the second body have a length which is not less than 1 quarter of that of the first body, in order to provide efficient stabilization. Finally, it will be noted that such a second body may share with the first body or all part of the other technical features described in the present application.

The various independent but not exclusive embodiments detailed above represent solutions further having the advantage of being able to be used either as a trans-facet implant, or as an inter-facet implant, for example by the fact that the implants provides a wide space for bone grafting in its internal conduit and/or that the bone will be sharpened by the passage of the implant and/or that the stability of the implant is improved relatively to the known solutions.

Further, it is sometimes preferable, for better solidity, to keep a solid body at the portion on which the largest forces will be exerted, such as for is example the portion which will be finally positioned between the facets and/or the one where the forces transmitted through the stabilization means are exerted. Thus, said "at least one portion of the longitudinal axis" in which is made the internal conduit (11) will sometimes be a distal portion (on the side of the end opposite to the head) or median portion, notably in the case of an intra-facet implantation, but may also be more proximal. Nevertheless, the body may be hollow and solid on variable portions along the longitudinal axis, for example according to the intended uses for the implant. Further, it is generally preferred that the body (10) be hollow over the whole of its length, so that the implant may be more easily implanted by means of a pre-positioned broach like in the known techniques of the prior art and allowing that the implant, slipped onto the broach, may slide as far as its implantation site and may then be screwed into the bone tissue (or cartilage tissue, moreover it will be noted that the terms of "bone" or "osseous" designate in the present application both the bone and the cartilage). It is therefore preferable to provide at least one passage for such a broach, even if at least one portion not including any longitudinal internal conduit is used. Thus, for example, FIGS. 24A and 24B illustrate in an illustrative and non-limiting way an implant comprising a hollow proximal portion, a solid median portion and a hollow distal portion, while FIGS. 25A and 25B illustrate an implant of the same type, but in which the median side portion however includes a passage (110) for such a broach and/or for communication between the two grafting chambers provided by the two longitudinal internal conduits. The person skilled in the art will understand that various alternatives for positioning and dimensioning the various conduits and passages are possible. Indeed, the rigidity of the implant or of certain portions may vary depending on the internal conduit or passage which may be, along the longitudinal axis, big, and then small, and then big, etc., as illustrated for example in FIG. 16B where the two internal conduits (11) communicate through a larger passage than the one illustrated in FIG. 25B. Further, it will be noted that it is possible to make windows (15) at the portions having such a passage, as for example in FIG. 16B, or to prefer not making them as in FIG. 25B. This remains true regardless of the size of the passage and regardless of the method for making the windows (longitudinal or transverse machining operation), insofar that the diameter of the latter does not exceed a certain value beyond which it will necessarily open onto the outside of the body. Further, instead of providing a longitudinal internal conduit (11) providing a substantially cylindrical grafting chamber, as illustrated for example in FIGS. 13A and 13B, it is possible to provide conduits and/or passages (broach and/or communication passages in particular) with a conical shape, as for example illustrated in FIGS. 14B and 15B. Such a shape has the advantage of providing a grafting chamber size and a solidity of the implant which are variable along the longitudinal axis. Depending on the needs, it will therefore be possible to adjust the conduits and/or passages for obtaining more or less solid portions and/or intended to provide more or less wide grafting chambers. It will be noted that any combinations of conduits and/or passages with a conical or frusto-conical shape with solid portions or provided with a more or less wide passage, are possible and within the scope of the present description.

In certain embodiments, said free end of the body (10) is self-drilling. By the term of "self-drilling" is meant here that this end is capable of drilling the bone tissue by itself. Such a functional definition may simplify the application with a pointed shape of the end but may also be advantageously obtained with a split head or by the fact that a window (15) is present on an extreme distal portion and provides a cutting surface giving the possibility of drilling into the bone tissue. FIGS. 26B and 26C illustrate an example of a pointed free end. In this example, the end is solid and it is provided with a notch (112.) which provides a cutting edge allowing easy penetration into the bone. It will be noted that it is possible to provide that this free end is not solid, but rather hollow, as illustrated for example in FIG. 27C where it includes a passage (111) (narrower than the internal conduit) or for example, because the internal conduit (11) extends as far as this distal end. On the other hand, instead of a notch on a pointed end, it is possible to provide a notch on a cylindrical or conical or frusto-conical end, but it is also possible to provide that the drilling function be obtained through at least one window (15) at the distal end. Thus, for example, a window (15) may be made, which extends over several turns (12) and which provides a cutting edge with which the bone may be sharpened more easily.

Moreover, it will be noted that in many embodiments illustrated in the figures, the windows (15) are made between the turns (12) of the threading and generally between the totality (and the quasi-totality) of the turns. However, it is possible to make these windows only on one portion of the turns. Thus, at least one portion of said windows (15) are for example separated by at least two turns (12) without any window (15). Conversely (but not exclusively and in a way which may be combined with the embodiments detailed above), like for the free end, it is possible to provide on various portions (proximal, median or distal portions), windows which extend over several turns rather than being confined to the space between two turns. Thus, in certain embodiments, at least one portion of said windows (15) are made on several turns (12), as for example illustrated in FIG. 29B, 30B, 31B, 32B or 35B. It will be noted that it is possible to select diverse angular distributions (radially) of these apertures or windows around the longitudinal axis, in order to optimize the sharpening effect and/or self-filling effect during the screwing. indeed, when the windows are present on the areas which extend over several turns, these areas form portions where the diameter of the implant is locally reduced and optionally allows the sharpening of the bone structures to be improved and that the hollow implant is gradually filled with thereby sharpened bone during the screwing, at least at the areas with a reduced diameter, as explained earlier, notably (but not exclusively) during screwing between two bone structures which tend to come closer to each other (at least locally, for example on portions of a size similar to that of these areas with reduced diameter). Further, by distributing the windows radially pair wise (i.e., so that a window is always diametrically opposite to another), this effect is further increased. since the diameter is even more reduced locally. It will be noted that this filling of the implant with bone or cartilage may also advantageously limit the risk of spontaneous withdrawal of the implant, since the growth and bone fusion through the implant blocks the rotation and therefore the withdrawal of the implant (or an undesired advance)

Thus, it is understood from the foregoing that various combinations of the features discussed in the present applications may be contemplated, such as for example a conical implant body with cylindrical threads which may be provided so as to enhance the bone engagement at the end and facilitate the self-filling effect, and optionally with windows of variable dimensions, for example, mainly greater at the end for also promoting the self-drilling or self-tapping aspect in this case.

As regards the turns (12) of the threading of the body, it is understood that they may be provided on all or part of the body, whether this is along the longitudinal axis or around the latter. For example, portions (19) may be provided, wherein non-turn/thread portions (16) do not exceed the perimeter of the body, even if windows are all the same made on these portions, such as for example as illustrated in FIGS. 9A, 9B, 9C, 13A, 13B, 14A, 14B, 15A, 15B, 16A, 16B. Further, it will be noted that these illustrative examples of the figures show such portions (19) at a generally proximal level since it is there where it is less necessary to have turns deeply anchored in the bone tissue, but various alternatives are of course possible. On the other hand, in certain embodiments, the turns (12) of the threading are "retentive", i.e., they have a shape which promotes retention of the implant in the bone tissue. such a function may be fulfilled by the fact that the turns have a face (120) facing the proximal head (the head) which is opposed to the withdrawal of the implant, for example by the fact that this face is oriented in a plane substantially perpendicular to the longitudinal axis, or even slightly tilted toward this proximal end, as illustrated for example in FIG. 27C and especially 28B. Further, in order to facilitate implantation, the other face (121) of the turns (the one facing the distal end) may on the contrary be tilted in order to facilitate penetration, i.e., it is preferably not parallel to the longitudinal axis but rather tilted towards the distal end, as illustrated for example in FIG. 28B. Nevertheless, this useful layout is not limiting and the geometry of the thread may be diverse such as for example trapezoidal, triangular, etc.

As regards the pitch of the threading, i.e., the spacing of the turns along the longitudinal axis, the present application also provides various types of non-limiting layouts which may be useful depending on the conditions. In particular, in certain embodiments, the turns (12) of the thread (or by extension the thread (12) of the implant) have variable pitch which shortens in the direction of the head (18). Also, in certain embodiment, the body (10) is provided with several threads (12) with different pitches. Preferably, the pitch of a thread located on the side of the free end is of a larger size than the adjacent thread located on the side of the head (18), so that the pitch of the thread is gradually reduced upon advancing towards the head. This type of layouts with variable pitch gives the possibility of obtaining a compressional effect. Indeed, when such an implant with variable pitch or comprising several threads with decreasing pitches is screwed in, a compressional effect is obtained which is for example particularly useful in the case of screwing in a bone structure where it is desired to properly flatten the structures together, like for example a trans-facet implantation.

In a general way, the implant will be inserted so that the majority of the body (10) penetrates into bone or cartilage tissue or between two bone structures and so that the head remains on the outside, but it is possible to provide that the head is at least partly intended to be also inserted inside the treated structures. Preferably, it is provided that the head remains on the outside and various embodiments of the present application provide in a useful way that the head bears upon (and is therefore on the outside) the surfaces. As various embodiments provide at least one internal conduit (11), it may be useful to block the latter so as to avoid bone growth risks at the surface of the treated portions and/or invasion risks of the interior of the implant by other tissues or undesirable organisms. Thus, in certain embodiment, the said head (18) of the implant (1) closes the longitudinal internal conduit (11) or includes means (3) for closing the longitudinal internal conduit (11). Such closing means give the possibility of providing an implant capable of being slipped onto a broach assisting the implantation like in the prior art and nevertheless allows the implant to be blocked after implantation. However it will be noted that various embodiments in fact include means for stabilizing the implant, as detailed hereafter, which generally include locking means which may, according to various embodiments, fulfill this function for closing the implant. Nevertheless, in various embodiments, the locking means will be laid out so as not to block the implant so that the locking of the stabilization means may be achieved in the presence of an optional broach; it will then be possible to either provide or not closing means for blocking, according to various embodiments. Such closing or blocking means may for example include at least one screw or a bolt mating a tapped hole in the head, but may also include a plug provided with lugs intended to be fastened with clips in an accommodation of the head, or any other means within the reach of the person skilled in the art.

Figure 7A:
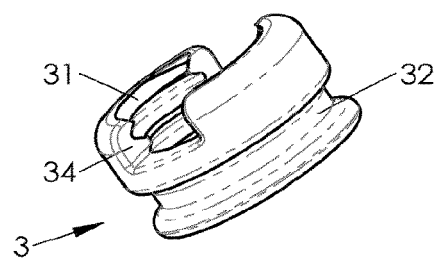
Figure 7B:
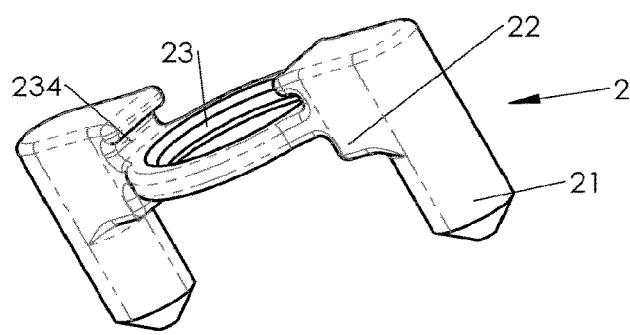
Figure 7C:
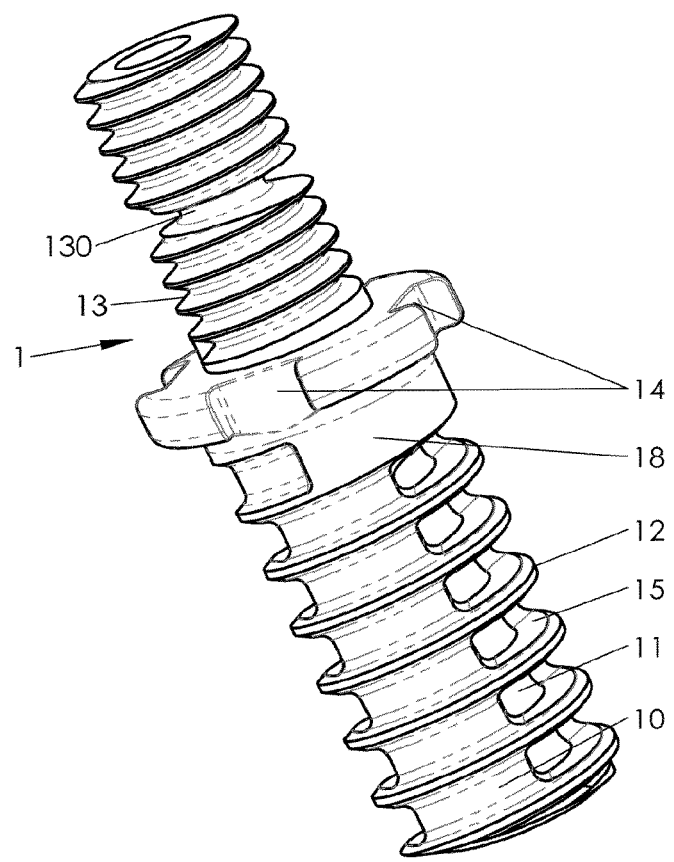

In certain embodiments, said head (18) of the implant (1) is provided with means (2, 3, and 5) for stabilizing the implant, which are preferably intended to bear upon the bone tissue around said head (18). In certain of these embodiments, said stabilization means (2, 3, 5, 6) include at least one stabilization element (2) comprising pointed structures (21, 61, 265, 275, 276, 390), such as notches or teeth, spikes, rods or nails or anchors or further hooks, adapted for penetrating into the bone tissue. Such stabilization means give the possibility of an additional bone anchoring in proximity to the implant, which stabilizes the latter. For example, certain of these embodiments comprise a stabilization element (2) forming a sort of staple comprising at least two rods (21) substantially parallel to the longitudinal axis and able to penetrate the tissue around the head (18) and optionally a portion of said body (10) in proximity to said head (18). Examples of such stabilization means (2) are for example illustrated in FIGS. 2C, 3D, 7B showing elements comprising a ring intended to be slipped onto a portion of the head and at least one tip intended to be planted into surrounding tissues, In certain of these embodiments, said rods (21) of the stabilization element (2) have a pointed free end. The term of "pointed" in said description in fact more widely designates the fact that a structure is able to penetrate the bone tissue, by therefore covering, in a non-limiting way, beveled structures as well as pointed structures. Further, in certain embodiments, said rods (21) are connected together through a ring (23) making the stabilization element (2) able to be mounted on said head (18), as illustrated for example in FIGS. 2C, 3D, 7B, but the person skilled in the art will appreciate that this type of mounting on the head is only an illustrative and non-limiting example since various layouts will give the possibility of mounting means for the stabilization means on the head (or on any other portion of the implants optionally). According to various alternatives, the ring (23) is slipped or screwed onto a high portion (13) which juts out from the head (18), as illustrated for example in FIGS. 6A, 6B, 6C and 6D, whereas, in other alternatives, the ring rests on the head and its aperture is able to receive a low portion (13) of locking means (3) which are attached in the head of the implants as illustrated for example in FIG. 1D or 3A, It will be noted that the figures show threadings and tappings for attaching locking means on the head but that various types of layouts are possible as detailed above with reference to the means for closing the implant.

In certain embodiments, in particular those comprising a stabilization element (2) provided with two rods (21) intended to penetrate the bone tissue around said head (18), the latter includes at least two notches (14) able to receive said rods (21) or shoulders (22) positioned along said rods (21) as illustrated for example in FIG. 1A, 1B, 1C, 1D, 2A, 2C, 2D, 3A, 3B, 3D, 3F or 6A, 6B, 6C, 6D, 7B and 7C. Such notches (14) give the possibility of imposing the positions of the rods (21) around the implant, so that it is possible to provide that they be ideally positioned relatively to the treated bone structures (notably so that they are each planted in one of the adjacent vertebrae during an intra-facet implantation). Further, the presence of a shoulder (22) (and of material between the center of the stabilization element and said rods) allows said rods to be maintained at a distance from the body (10), so that these rods may be planted at a distance ensuring better stabilization than if they had been closer to the body of the implant.

Further, in certain embodiments, an instrument (4) is provided for the implantation of various embodiments of the implant (1). Such an instrument (4) generally includes an elongated body between an end which may be handled by means of a handle (41) for example and an end holding the implant and preferably includes an internal conduit (46), as illustrated for example in FIGS. 5B and 8B, so as to be able to be slipped on around a guiding broach as detailed above. Further, in order to facilitate implantation, such an instrument (4) may include at its end intended to hold the implant at least one lug or protrusion (44) mating at least one notch (14) of the instrument as detailed above. The cooperation between this lug (44) and the notch (14) allows actuation of the implant in rotation by the instrument so as to screw the implant into the structures to be treated. Further, the instrument (4) sometimes includes on the perimeter of its tubular body at least one groove (43) able to receive a piercing tool allowing the bone tissue to be pierced, into which the rods (21) of the stabilization element will be inserted. In such embodiments, the implant preferably includes a number of notches (14), double the number of rods (21) present on the stabilization means, in order to facilitate the implantation as detailed hereafter, In such embodiments, the implants for example includes 4 notches regularly positioned around the longitudinal axis of the implant and so that the instrument allows the implant to be gripped with its diametrically opposite lugs (44), while the rods (21) of the stabilization element (2) are held by the instrument and engaged into the other notches, for example in a radial position shifted by 90° relatively to the lugs (44). Thus, it is possible by moving the instruments backward, to perform a rotation by a quarter of a turn in order to bring the rods so that they face the notches (14) via which a perforation was made in the bone tissue and to thus introduce these rods into the holes. This type of layout facilitates the implantation by allowing preliminary piercing and by avoiding that the rods (21) interfere with the screwing of the body, for example as in the case when they would be provided to be interdependent with the body (10) in rotation. It will be noted that the term of "rod" is used here for designating the structures intended to penetrate into the bone tissue around the body, but it is clear that the shape of such stabilization means may vary and provision is made for rather using plates, with a. variable section and optionally T, V, H or U sections in order to provide better strengths in several dimensions. In the case of plates, it will be noted that they may be pointed or sharpened, optionally to the point of not requiring any preliminary perforation. The instrument preferably includes means for retaining the implants and generally a retaining element (45) for the locking means, as illustrated for example in FIGS. 5D and 8D. In these examples, the implants include a tapped hole (31) able to receive threaded rods (13) of the locking means (3) as illustrated for example in FIGS. 1D, 2D, 3B, 3C, 3F, or includes a threaded rod (13) able to receive a tapped hole (31) of the locking means (3) as illustrated for example in FIGS. 6D, 7C, 8D. such a retaining means (45) may then for example include a rod intended to be flattened against the threaded rod (13) and thereby retain the assembly as illustrated in these examples of figures or include a threaded rod (46) (preferably tubular for the guiding broach) cooperating with a tapped hole (31) of the implant, as illustrated for example in FIG. 18C. Further, the instrument may include, at its end retaining the implant, means for transmitting the rotation, such as for example planar surfaces not tangent to the perimeter of the implant and cooperating with substantially identical orientation surfaces of the implant, such as for example a nut-shaped end intended to penetrate into a six-sided accommodation of the implant, as shown in the illustrative example of FIG. 17B for example. In the examples of FIGS. 6A, 6B, 6C, 6D, 7A, 7, 7C, 8A and 8B, it will be noted that the implant in fact includes a threaded rod (13) jutting out from the head (18) and provided with a self-breakable portion, for example obtained by means of a notch (130) as for example visible in FIG. 7C. In this type of layout, the stabilization means (2) preferably include a ring (23) provided with spikes (21) as detailed earlier, but are associated with locking means (3) which may for example include a ring provided with tapping (31) able to be screwed onto the threaded rod (13). This ring preferably also includes notches (34) able to cooperate with the end of a screwing tool. On the other hand, a groove (32) may be provided on this locking means (3) in order to allow it to be fastened with clips on a lip (234) of the stabilization means, as for example visible in FIGS. 6 and 7. The person skilled in the art will understand from the various technical considerations above that various layouts are possible for retaining the implant and that the means and elements above are illustrative and non-limiting. In certain embodiments, said stabilization means include at least one stabilization element (2) with the shape of a bell, a crown, a ring, an annulus, or any shape suitable for being mounted on (or secured to) the head (18), preferably around at least one portion of the head. The term of "bell" is used here for referring to the mounting around the head and for indicating that the perimeter (210) of this stabilization element is intended to be supported on the bone tissue surrounding the head (18), as for example illustrated in FIGS. 9A, 9B, 9C, 10A, 10B, 11A, 11B, etc.

It is understood that the whole of the perimeter (210) of the bell is not necessarily supported on the bone tissues all around the screw, according to the configurations, but that a support is obtained and gives the possibility of stabilizing the screw and the articular elements. In particular, diverse embodiments aim that the perimeter of the bell surrounds and covers a portion of the protruding bone structures, in order to stabilize them among each other. Further, such a perimeter (210) may include teeth or notches (21) contributing to the stabilization, such as for example in FIGS. 12A, 12B and 12C. In various embodiments, the bell secured to the head is formed in a single piece with the head or is attached above. In other embodiments, the bell is movably mounted around the head. Further, the bell may be of the same material as the body of the implant (generally a solid metal material, such as for example titanium), but it is possible to provide a bell in another notably more flexible material, so that it is crushed during the final screwing of the locking means and thus ensures efficient compression. A possible and useful material for this type of alternative embodiments is PEEK well-known in the field. Preferably, the body of the implant is in a resistant material or at least coated with such a material, such as for example titanium. It will be noted that even if a resistant and durable material is generally preferred for the implant, like titanium, for example certain embodiments on the contrary provide the use of a resorbable material, for example like bone or bone substitute. Indeed, the use of such a resorbable material, preferably sufficiently resistant before its resorption for maintaining the targeted attachment function, gives the possibility of obtaining finally complete bone fusion without any foreign body, which naturally has many advantages, notably for the patient.

In certain embodiments, the bell is mobile and allows a support of the "poly-axial" type, i.e., that it may be positioned against the surrounding bone tissue, or even locked, in diverse positions relatively to the longitudinal axis of the implant. For example, in certain of these embodiments, said head (18) has a peripheral lower surface (180) with the shape of a sphere portion, as illustrated for example in FIGS. 18C, 22A, 22B, 22E, 22F, 23A, 23B, 23E, 28A and 28B. Such a surface is generally provided so as to be complementary to an internal upper surface of said bell (2) thus jointed on the head (18) of the implant, as illustrated for example in FIG. 12C, so as to allow an adjustment of the orientation of the bell relatively to the axis of the head. Further, it will be noted that in such embodiments, it is preferred to use a limited sphere portion instead of a complete sphere or with too large dimensions, so that the portion of the implant which subsists at the surface of the bone tissue is not too exposed to aggressions (notably outer aggressions), as already detailed in the present application. Indeed, even if the range of possible orientations of the bell is thereby restricted, it remains generally sufficient and the implant will be clearly more stable than with a large angle and especially a larger protrusion at the surface of the bone tissue.

In certain embodiments, said bell (2) includes at least one tip or tooth (21) on its perimeter (210) for facilitating bone anchoring as illustrated for example in FIGS. 12A, 12B and 12C. This type of layout of the low portion of the bell, intended to bear upon the bone tissue, gives the possibility of improving the adhesion of the bell on the latter and thus improves the stability of the implant. In certain embodiments, the bell (2), in particular when it is secured to the body (10) of the implant, includes coupling means (29) with a tool for screwing the implant, such as for example illustrated in FIGS. 9A, 9B, 9C, 10A, 10B and 11C. In these examples, these coupling means (29) are advantageously holes capable of receiving lugs of a screwing instrument but the reverse configuration may be contemplated or diverse coupling means may be used. When the stabilization means are mobile around the implant, direct coupling on the implant will of course be preferred, like the coupling means (14) detailed in the present application for example. It will be noted that these coupling means (14) of the implant may also assume diverse shapes, as specified here for the coupling means of the bell (2). In certain embodiments, said stabilization means include at least one plate (5) mounted around the head (18) and provided with at least one passage (57) able to receive a stabilization element (2), a so-called anchor, in the form of a plate (20) able to be anchored in the bone tissue around the head (18), as illustrated for example in FIGS. 19A, 19B, 19C, 20A, 20B and 20C. Like for the rods (21) described in the present application, the plates (20) may have diverse shapes and this term is not limiting, although plates are preferred to rods for the stability which they provide. Also, the plates illustrated in the figures are not limiting and as explained for the rods, it is possible to provide T, V, H, U plates etc. in order to provide better stabilization (by the fact that one in fact has several plates not parallel with each other which oppose the movements in several directions). In certain of these embodiments, said anchor (2) includes a pointed end (21) and/or sharpened edges intended to penetrate the bone tissue (pointed or sharpened designating here means for penetrating the bone). Preferably, said anchor (2) includes an end provided with at least one abutment (22) intended to come into contact with said plate (5) and limit the penetration of the anchor (2) into the bone tissue. The anchor may generally be provided with retaining means in the bone tissue. Thus, as an addition or an alternative to such an abutment, the anchor may include catches avoiding its withdrawal out of the bone or be associated with another locking means such as for example an additional screw, for which at least one portion retains the anchor. Further, according to the provided approach routes and invasivity for the implant, it is possible to provide various shapes for such an anchor. Thus, in certain embodiments, said anchor (2) is formed with a substantially planar plate (20), while in other embodiments, said anchor (2) is formed with a substantially curved plate (20). A combination of a flat anchor and of a curved anchor may of course be contemplated. For better stability of the anchor, certain embodiments provide that said anchor (2) and said passage (57) are laid out for inserting the anchor along an oblique axis relatively to the longitudinal axis, so that the anchor is oriented from the center to the periphery of the implant during the insertion, as illustrated for example in FIGS. 19A, 19B, 19C, 20A, 20B and 20C. It will be noted that the illustrative examples of these last figures show alternatives which notably differ in that said plate (5) is provided so as to be mounted on (or optionally secured to) the implant and for receiving the anchors which are locked by a locking means (3) such as a screw or a bolt, as illustrated for example in FIGS. 20A, 20B and 20C. Such a locking means added after insertion of the anchors gives the possibility of locking the assembly. On the other hand, in the examples of FIGS. 19A, 19B and 19C, said plate (5) is separated from the implant which is then screwed through the plate (5) receiving the anchors (2). In these examples, the locking may be obtained with the head of the implant which bears upon the anchors as illustrated for example in FIG. 19C or with an additional pin (screw or bolt) of the type of that of FIG. 20B for example.

Finally, in other embodiments illustrating the possible diversity of the stabilization means, it is possible to provide at least one stabilization element (2) in the form of a jaw comprising two curved bits (20) each comprising a free end (21) and jointed with each other through two joints (28) separated from each other by a space with a size substantially equal to the size of the head (18), as illustrated for example in FIGS. 21A, 21B and 21C. In this type of layout, the jaw may be mounted around the head and the bits may come into contact with the bone tissues around the body (10) of the implants in order to stabilize the assembly; in these embodiments, said stabilization means preferably include locking means (3) bearing upon the stabilization element (2) for maintaining it pressed against the bone tissue. In certain of these embodiments, the bits (20) of said jaw (2) include on their concave face, at least one catch (211) for stabilizing them against the bone tissue. Further, in certain embodiments, the free end (21) of the bits (20) includes at least one chamfer (218) facilitating the opening of the jaw (2) upon inserting the implant into the bone tissue.

The present application describes various technical features and advantages with reference to the figures and/to diverse embodiments. The person skilled in the art will understand that the technical features of a given embodiment may in fact be combined with features of another embodiments unless the opposite is explicitly mentioned or if it is only obvious that these features are incompatible or if the combination does not operate or does not provide solution to at least one of the technical problems of the field, in particular those mentioned in the present application. Further, the technical features described in a given embodiment may be isolated from the other features of this embodiment unless the opposite is explicitly mentioned, notably by the functional considerations provided in the present application and the detailed structural specificities in the description and the figures of the present application.

It should be obvious for skilled practitioners that the present invention allows embodiments under many other specific forms without departing from the field of application of the invention as claimed. Therefore, the present embodiment should not be considered as an illustration but may be modified within the field defined by the scope of the appended claims and the invention should not be limited to the details given above.

What is claimed is:

1. A bone implant comprising:
a body elongated along a longitudinal axis between a proximal end of the body and a distal end of the body, the body comprising a rounded exterior surface portion disposed proximal to a first end of the body and having a rounded cross-section transverse to the longitudinal axis;
a head integrally formed on the proximal end of the body, the head including a major diameter larger than the rounded cross-section;
a self-drilling end integrally formed on the distal end of the body;
a bore extending through at least a portion of the body along the longitudinal axis and opening through the distal end of the body;
a thread winding in a direction around at least a portion of the rounded exterior surface portion of the body, wherein a portion of the thread has a peak that defines a thread diameter for the portion of the thread which is no greater than a diameter of the rounded exterior surface portion of the body; and
a plurality of windows disposed along a portion of the body and forming openings between adjacent portions of the thread winding extending from the bore through the rounded exterior surface portion, wherein the plurality of windows each comprise a first side that is aligned with the thread in the direction of winding and a second side that is transverse to the direction of winding, wherein the first side is longer than the second side.

2. The bone implant of claim 1, wherein the plurality of windows incrementally increases in size from the proximal end to the distal end of the portion of the body.

3. The bone implant of claim 1, wherein the plurality of windows incrementally decreases in size from the proximal end to the distal end of the portion of the body.

4. The bone implant of claim 1, further comprising a second portion of the body including a second plurality of windows.

5. The bone implant of claim 4, wherein the second plurality of windows increase in size from a proximal end of the second portion to a distal end of the second portion.

6. The bone implant of claim 5, wherein the portion of the body with the plurality of windows is a first portion of the body, and wherein the second portion is distal to the first portion.

7. The bone implant of claim 1, wherein each window of the plurality of windows is flared to create at least one sharpened outer edge.

8. The bone implant of claim 7, wherein each window of the plurality of windows includes a first opening on an outside of the body connected to a second opening on an inside of the body, and wherein each window of the plurality of windows is flared from the inside of the body to the outside of the body such that the second opening is smaller than the first opening.

9. The bone implant of claim 1, wherein the body has a substantially frustoconical shape.

10. The bone implant of claim 1, wherein the thread has a perimeter that is substantially cylindrical.

11. The bone implant of claim 1, wherein the plurality of windows is aligned along an axis substantially parallel to the longitudinal axis.

12. A bone anchor comprising:
a body with a sidewall, the body including a longitudinal axis extending from a proximal end and a distal end;
a head disposed on the proximal end of the body, the head including a major diameter larger than a cross-section of the body;
a self-drilling end integrally formed on the distal end of the body;
a bore extending through at least a portion of the body along the longitudinal axis and opening through the distal end of the body;
a thread winding around a circumference of the body and extending from adjacent the head to the distal end;
a first plurality of windows extending through a first more-proximal portion of the sidewall of the body having a first diameter and into the bore, wherein a first portion of the thread in the first more-proximal portion of the sidewall of the body has a peak that defines a thread diameter for the first portion of the thread which is no greater than the first diameter of the body; and
a second plurality of windows extending through a second more-distal portion of the sidewall of the body having a second diameter and into the bore,
wherein the first diameter is greater than the second diameter.

13. The bone anchor of claim 12, wherein the first plurality of windows and the second plurality of windows incrementally increase in size from the proximal end to the distal end of the sidewall of the body.

14. The bone anchor of claim 12, wherein the first plurality of windows and the second plurality of windows incrementally decrease in size from the proximal end to the distal end of the sidewall of the body.

15. The bone anchor of claim 12, wherein the first plurality of windows and a first subset of the second plurality of windows incrementally decrease in size from the proximal end towards the distal end to a mid-point in the body, and the remaining windows of the second plurality of windows incrementally increase in size to the distal end.

16. The bone anchor of claim 12, wherein at least some windows of the first plurality of windows and the second plurality of windows are flared to create at least one sharpened outer edge.

17. The bone anchor of claim 16, wherein the at least some windows of the first plurality of windows and the second plurality of windows includes a first opening on an outside of the body connected to a second opening on an inside of the body, and wherein the at least some windows of the first plurality of windows and the second plurality of windows is flared from the inside of the body to the outside of the body such that the second opening is smaller than the first opening.

18. The bone anchor of claim 12, wherein the body has a substantially frustoconical shape.

19. The bone anchor of claim 12, wherein the thread has a perimeter that is substantially cylindrical.

20. The bone anchor of claim 12, wherein each window of the first plurality of windows and the second plurality of windows includes at least one sharpened outer edge configured to penetrate bone tissue.

* * * * *